(12) United States Patent
McMahon et al.

(10) Patent No.: US 7,803,786 B2
(45) Date of Patent: Sep. 28, 2010

(54) PHARMACEUTICAL CO-CRYSTAL COMPOSITIONS AND RELATED METHODS OF USE

(75) Inventors: Jennifer McMahon, Tampa, FL (US); Matthew Peterson, Hopkinton, MA (US); Michael J. Zaworotko, Tampa, FL (US); Tanise Shattock, Sunrise, FL (US); Magali Bourghol Hickey, Medford, MA (US)

(73) Assignees: Transform Pharmaceuticals, Inc., Lexington, MA (US); University of South Florida, Tampa, FL (US)

( * ) Notice: Subject to any disclaimer, the term of this patent is extended or adjusted under 35 U.S.C. 154(b) by 610 days.

(21) Appl. No.: 11/629,807

(22) PCT Filed: Jun. 16, 2005

(86) PCT No.: PCT/US2005/021662

§ 371 (c)(1),
(2), (4) Date: Jul. 9, 2007

(87) PCT Pub. No.: WO2006/007448

PCT Pub. Date: Jan. 19, 2006

(65) Prior Publication Data

US 2007/0299033 A1    Dec. 27, 2007

Related U.S. Application Data

(60) Provisional application No. 60/580,661, filed on Jun. 17, 2004, provisional application No. 60/585,808, filed on Jul. 6, 2004, provisional application No. 60/621,485, filed on Oct. 22, 2004, provisional application No. 60/628,701, filed on Nov. 17, 2004.

(51) Int. Cl.
| | |
|---|---|
| *A61K 31/7028* | (2006.01) |
| *A61K 31/55* | (2006.01) |
| *A61K 31/175* | (2006.01) |
| *A61K 31/4196* | (2006.01) |
| *C07D 223/18* | (2006.01) |
| *C07H 19/048* | (2006.01) |
| *C07C 275/00* | (2006.01) |

(52) U.S. Cl. .......... 514/50; 514/217; 514/383; 514/424; 514/592; 536/28.53; 540/588; 548/266.6; 548/550; 564/39

(58) Field of Classification Search ............ 514/50, 514/217, 383, 424, 592; 536/28.53; 540/588; 548/266.6, 550; 564/39
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,366,738 A | 11/1994 | Rork et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 6,132,420 A | 10/2000 | Dionne et al. | |
| 6,245,357 B1 | 6/2001 | Edgren et al. | |
| 6,270,787 B1 | 8/2001 | Ayer | |
| 6,283,953 B1 | 9/2001 | Ayer et al. | |
| 6,287,295 B1 | 9/2001 | Chen et al. | |
| 6,333,050 B2 | 12/2001 | Wong et al. | |
| 6,342,249 B1 | 1/2002 | Wong et al. | |
| 6,365,185 B1 | 4/2002 | Ritschel et al. | |
| 6,368,626 B1 | 4/2002 | Bhatt et al. | |
| 6,375,978 B1 | 4/2002 | Kleiner et al. | |
| 6,635,753 B1 | 10/2003 | Radatus et al. | |
| 7,078,526 B2 | 7/2006 | Remenar et al. | |

FOREIGN PATENT DOCUMENTS

WO    WO 03/074474    9/2003

OTHER PUBLICATIONS

Brader, M.L. et al. "Hybrid insulin cocrystals for controlled release delivery" *Nature Biotechnology*, 2002, pp. 800-804, vol. 20.

Drug Facts & Comparisons, 2004 Edition, p. 368, 1173, 1177, and 1702, Wolters Kluwer Health, St. Louis, Missouri.

McMahon, J.A. et al. "Crystal Engineering of the composition of pharmaceutical phases 3. Primary amide supramolecuar heterosynthons and their role in the design of pharmaceutical co-crystals" *Z. Kristallographie*, 2005, pp. 340-350, vol. 220, XP-008104807.

Database Chemical Abstracts Service, Accession No. 1974:463365, Aumueller, W. et al. "(Phenylsulfonyl)ureas", May 30, 1974, XP-002522688, pp. 1-2.

Scott, E.M. et al. "Demonstration of Synergy with Fluconazole and Either Ibuprofen, Sodium Salicylate, or Propylparaben against *Candida albicans* in Vitro", *Antimicrobial Agents and Chemotherapy*, Dec. 1995, pp. 2610-2614, vol. 39, No. 12, XP-002196358.

Callahan, J. C. et al. "Equilibrium Moisture Content of Pharmaceutical Excipients" *Drug Development and Industrial Pharmacy*, 1982, pp. 355-369, vol. 8, No. 3.

*Primary Examiner*—Raymond J Henley, III
(74) *Attorney, Agent, or Firm*—Saliwanchik, Lloyd & Saliwanchik

(57) ABSTRACT

The present invention comprises pharmaceutical compositions comprising a co-crystal of an API and a co-crystal former, and methods of making and using the same.

15 Claims, 13 Drawing Sheets

PHARMACEUTICAL CO-CRYSTAL COMPOSITIONS AND RELATED METHODS OF USE

CROSS-REFERENCE TO RELATED APPLICATIONS

The present application is the U.S. national stage application of International Patent Application No. PCT/US2005/021662, filed Jun. 16, 2005, which claims the benefit of priority of U.S. Provisional Application Ser. No. 60/580,661, filed Jun. 17, 2004, U.S. Provisional Application Ser. No. 60/585,808, filed Jul. 6, 2004, U.S. Provisional Application Ser. No. 60/621,485, filed Oct. 22, 2004, and U.S. Provisional Application Ser. No. 60/628,701, filed Nov. 17, 2004, the contents of which are incorporated herein by reference in their entireties.

FIELD OF THE INVENTION

The present invention relates to co-crystal API-containing compositions, pharmaceutical compositions comprising such APIs, and methods for preparing the same.

BACKGROUND OF THE INVENTION

Active pharmaceutical ingredients (API or APIs (plural)) in pharmaceutical compositions can be prepared in a variety of different forms. Such APIs can be prepared so as to have a variety of different chemical forms including chemical derivatives or salts. Such APIs can also be prepared to have different physical forms. For example, the APIs may be amorphous, may have different crystalline polymorphs, or may exist in different solvation or hydration states. By varying the form of an API, it is possible to vary the physical properties thereof. For example, crystalline polymorphs typically have different solubilities from one another, such that a more thermodynamically stable polymorph is less soluble than a less thermodynamically stable polymorph. Pharmaceutical polymorphs can also differ in properties such as shelf-life, bioavailability, morphology, vapour pressure, density, colour, and compressibility. Accordingly, variation of the crystalline state of an API is one of many ways in which to modulate the physical properties thereof.

It would be advantageous to have new forms of these APIs that have improved properties, in particular, as oral formulations. Specifically, it is desirable to identify improved forms of APIs that exhibit significantly improved properties including increased aqueous solubility and stability. Further, it is desirable to improve the processability, or preparation of pharmaceutical formulations. For example, needle-like crystal forms or habits of APIs can cause aggregation, even in compositions where the API is mixed with other substances, such that a non-uniform mixture is obtained. It is also desirable to increase or decrease the dissolution rate of API-containing pharmaceutical compositions in water, increase or decrease the bioavailability of orally-administered compositions, and provide a more rapid or more delayed onset to therapeutic effect. It is also desirable to have a form of the API which, when administered to a subject, reaches a peak plasma level faster or slower, has a longer lasting therapeutic plasma concentration, and higher or lower overall exposure when compared to equivalent amounts of the API in its presently-known form. The improved properties discussed above can be altered in a way which is most beneficial to a specific API for a specific therapeutic effect.

SUMMARY OF THE INVENTION

It has now been found that new co-crystalline forms of APIs can be obtained which often improve the properties of APIs as compared to such APIs in a non-co-crystalline state (free acid, free base, zwitter ions, salts, etc.).

Accordingly, in a first aspect, the present invention provides a co-crystal pharmaceutical composition comprising an API compound and a co-crystal former, such that the API and co-crystal former are capable of co-crystallizing from a solid or solution phase under crystallization conditions.

In another aspect, the present invention provides a pharmaceutical co-crystal composition, comprising: an API and a co-crystal former, wherein the API is a liquid or a solid at room temperature and the co-crystal former is a solid at room temperature, and wherein the API and co-crystal former are hydrogen bonded to each other.

In a first embodiment, the present invention provides a co-crystal comprising carbamazepine and 4-aminobenzoic acid. In another embodiment, the present invention provides a co-crystal comprising carbamazepine, 4-aminobenzoic acid, and water.

In another embodiment, the present invention provides a co-crystal comprising glyburide and TRIS. In another embodiment, the present invention provides a co-crystal comprising fluconazole maleate and maleic acid. In another embodiment, the present invention provides a co-crystal comprising piracetam. In another embodiment, the present invention provides a co-crystal comprising piracetam and gentisic acid. In another embodiment, the present invention provides a co-crystal comprising piracetam and 4-hydroxybenzoic acid. In another embodiment, the present invention provides a co-crystal comprising carbamazepine and acetylsalicylic acid. In another embodiment, the present invention provides a co-crystal comprising carbamazepine and cinnamic acid. In another embodiment, the present invention provides a co-crystal comprising stavudine. In another embodiment, the present invention provides a co-crystal comprising stavudine and melamine. In another embodiment, the present invention provides a co-crystal comprising stavudine and 2-aminopyridine. In another embodiment, the present invention further comprises a formic acid solvate of oxcarbazepine.

In another embodiment, a co-crystal is prepared via milling or grinding an API, a co-crystal former, and a small amount of solvent.

In another embodiment, a process is provided for preparing a pharmaceutical co-crystal composition comprising an API and a co-crystal former, comprising:
  (a) providing an appropriate solvent and the API and the co-crystal former, wherein the co-crystal former is a solid at room temperature;
  (b) grinding the API, the co-crystal former, and a small amount of the appropriate solvent, so as to form a solid phase, wherein the API and co-crystal former are hydrogen bonded to each other; and
  (c) isolating co-crystals formed thereby.

In another embodiment, the above process further comprises incorporating the co-crystals into a pharmaceutical composition or a medicament.

In another aspect, the present invention provides a medicament comprising an API compound and a co-crystal former, such that the API and co-crystal former are capable of co-crystallizing from a solid or solution phase under crystallization conditions.

In another aspect, the present invention provides a medicament, comprising: an API and a co-crystal former, wherein the API is a liquid or a solid at room temperature and the co-crystal former is a solid at room temperature, and wherein the API and co-crystal former are hydrogen bonded to each other.

In a still further aspect of the invention, a method is provided for treating a subject, preferably a human subject, with epilepsy, trigeminal neuralgia or another condition where carbamazepine or oxcarbazepine is an effective active pharmaceutical for said condition. The method comprises administering to the subject a therapeutically-effective amount of a co-crystal or a solvate of carbamazepine or oxcarbazepine.

In a still further aspect of the invention, a method is provided for treating a subject, preferably a human subject, with a condition able to be treated with an API where the API is an effective active pharmaceutical for said condition. The method comprises administering to the subject a therapeutically-effective amount of a co-crystal of an API, such as glyburide, fluconazole, gentisic acid, stavudine, or piracetam.

DETAILED DESCRIPTION OF THE INVENTION

Figure 1:
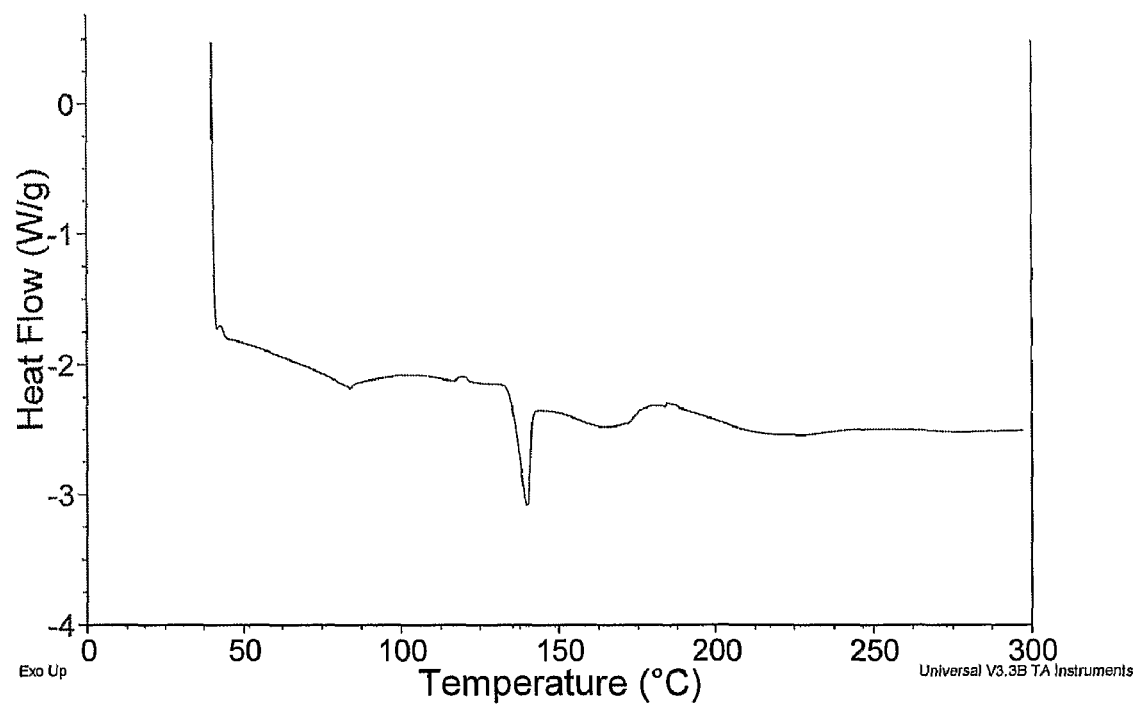
FIG. 1—DSC thermogram for glyburide:TRIS co-crystal.

The term "co-crystal" as used herein means a crystalline material comprised of two or more unique solids at room temperature (22 degrees C.), each containing distinctive physical characteristics, such as structure, melting point and heats of fusion, with the exception that, if specifically stated, the API may be a liquid at room temperature. The co-crystals of the present invention comprise a co-crystal former H-bonded to an API. The co-crystal former may be H-bonded directly to the API or may be H-bonded to an additional molecule which is bound to the API. The additional molecule may be H-bonded to the API or bound ionically or covalently to the API. The additional molecule could also be a different API. Solvates of API compounds that do not further comprise a co-crystal former are not co-crystals according to the present invention. The co-crystals may however, include one or more solvate molecules in the crystalline lattice. That is, a solvate of a co-crystal, or a co-crystal further comprising a solvent or compound that is a liquid at room temperature, is a co-crystal according to the present invention, but crystalline material comprised of only one solid and one or more liquids (at room temperature) are not co-crystals for purposes of the present invention, with the previously noted exception of specifically stated liquid APIs. The co-crystals may also be a co-crystal between a co-crystal former and a salt of an API, but the API and the co-crystal former of the present invention are constructed or bonded together through hydrogen bonds. Other modes of molecular recognition may also be present including, pi-stacking, guest-host complexation and van der Waals interactions. Of the interactions listed above, hydrogen-bonding is the dominant interaction in the formation of the co-crystal, (and a required interaction according to the present invention) whereby a non-covalent bond is formed between a hydrogen bond donor of one of the moieties and a hydrogen bond acceptor of the other. Hydrogen bonding can result in several different intermolecular configurations. For example, hydrogen bonds can result in the formation of dimers, linear chains, or cyclic structures. These configurations can further include extended (two-dimensional) hydrogen bond networks and isolated triads. An alternative embodiment provides for a co-crystal wherein the co-crystal former is a second API. In another embodiment, the co-crystal former is not an API. In another embodiment the co-crystal comprises two co-crystal formers.

For purposes of the present invention, the chemical and physical properties of an API in the form of a co-crystal may be compared to a reference compound that is the same API in a different form. The reference compound may be specified as a free form, or more specifically, a free acid, free base, or zwitterion; a salt, or more specifically for example, an inorganic base addition salt such as sodium, potassium, lithium, calcium, magnesium, ammonium, aluminum salts or organic base addition salts, or an inorganic acid addition salts such as HBr, HCl, sulfuric, nitric, or phosphoric acid addition salts or an organic acid addition salt such as acetic, propionic, pyruvic, malanic, succinic, malic, maleic, fumaric, tartaric, citric, benzoic, methanesulfonic, ethanesulforic, stearic or lactic acid addition salt; an anhydrate or hydrate of a free form or salt, or more specifically, for example, a hemihydrate, monohydrate, dihydrate, trihydrate, quadrahydrate, pentahydrate, sesquihydrate; or a solvate of a free form or salt. For example, the reference compound for an API in salt form co-crystallized with a co-crystal former can be the API salt form. Similarly, the reference compound for a free acid API co-crystallized with a co-crystal former can be the free acid API. The reference compound may also be specified as crystalline or amorphous. The reference compound may also be specified as the most stable polymorph known of the specified form of the reference compound.

According to the present invention, the co-crystals can include an acid addition salt or base addition salt of an API. Acid addition salts include, but are not limited to, inorganic acids such as hydrochloric acid, hydrobromic acid, sulfuric acid, nitric acid, and phosphoric acid, and organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutaric acid, hydroxynaphthoic acid, salicylic acid, stearic acid, and muconic acid. Base addition salts include, but are not limited to, inorganic bases such as sodium, potassium, lithium, ammonium, calcium and magnesium salts, and organic bases such as primary, secondary and tertiary amines (e.g. isopropylamine, trimethyl amine, diethyl amine, tri(iso-propyl) amine, tri(n-propyl)amine, ethanolamine, 2-dimethylaminoethanol, tromethamine, lysine, arginine, histidine, procaine, hydrabamine, choline, betaine, ethylenediamine, glucosamine, N-alkylglucamines, theobromine, purines, piperazine, piperidine, morpholine, and N-ethylpiperidine).

The ratio of API to co-crystal former may be stoichiometric or non-stoichiometric according to the present invention. Non-limiting examples such as, 1:1, 1.5:1, 1:1.5, 2:1 and 1:2 ratios of API:co-crystal former are acceptable. In addition, co-crystals with vacancies within the crystalline lattice are included in the present invention. For example, a co-crystal with less than or about 0.01. 0.1, 1, 2, 3, 4, 5, 6, 7, 8, 9, 10, 11, 12, 13, 14, 15, 16, 17, 18, 19, or 20 percent vacancies within the crystalline lattice are included in the present invention. The vacancies can be due to missing API molecules or missing co-crystal former molecules from the crystalline lattice, or both.

It has surprisingly been found that when an API and a selected co-crystal former are allowed to form co-crystals, the resulting co-crystals often give rise to improved properties of the API, as compared to the API in a free form (including free acids, free bases, and zwitterions, hydrates, solvates, etc.), or an acid or base salt thereof particularly with respect to: solubility, dissolution, bioavailability, stability, Cmax, Tmax, processability (including compressibility), longer lasting therapeutic plasma concentration, hygroscopicity, crystallization of amorphous compounds, decrease in form diversity (including polymorphism and crystal habit), change in morphology or crystal habit, etc. For example, a co-crystal form of an API is particularly advantageous where the original API is insoluble or sparingly soluble in water. Additionally, the co-crystal properties conferred upon the API are also useful because the bioavailability of the API can be improved and the plasma concentration and/or serum concentration of the API can be improved. This is particularly advantageous for orally-administrable formulations. Moreover, the dose response of the API can be improved, for example by increasing the maximum attainable response and/or increasing the potency of the API by increasing the biological activity per dosing equivalent.

Accordingly, in a first aspect, the present invention provides a pharmaceutical composition comprising a co-crystal of an API and a co-crystal former, such that the API and co-crystal former are capable of co-crystallizing from a solution phase under crystallization conditions or from the solid-state, for example, through grinding, heating, or through vapor transfer (e.g., co-sublimation). In another aspect, the API has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, imine, thiocyanate, cyanamide, oxime, nitrile, diazo, organohalide, nitro, S-heterocyclic ring, thiophene, N-heterocyclic ring, pyrrole, O-heterocyclic ring, furan, epoxide, peroxide, hydroxamic acid, imidazole, and pyridine and a co-crystal former which has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, imine, thiocyanate, cyanamide, oxime, nitrile, diazo, organohalide, nitro, S-heterocyclic ring, thiophene, N-heterocyclic ring, pyrrole, O-heterocyclic ring, furan, epoxide, peroxide, hydroxamic acid, imidazole, and pyridine, or a functional group in a Table herein, such that the API and co-crystal former are capable of co-crystallizing from a solution phase under crystallization conditions.

The co-crystals of the present invention are formed where the API and co-crystal former are bonded together through hydrogen bonds. Other non-covalent interactions, including pi-stacking and van der Waals interactions, may also be present.

In one embodiment, the co-crystal former is selected from the co-crystal formers of Table I and Table II. In other embodiments, the co-crystal former of Table I is specified as a Class 1, Class 2, or Class 3 co-crystal former (see column labeled "class" Table I). In another embodiment, the difference in $pK_a$ value of the co-crystal former and the API is less than 2. In other embodiments, the difference in $pK_a$ values of the co-crystal former and API is less than 3, less than 4, less than 5, between 2 and 3, between 3 and 4, or between 4 and 5. Table I lists multiple $pK_a$ values for co-crystal formers having multiple functionalities. It is readily apparent to one skilled in the art the particular functional group corresponding to a particular $pK_a$ value.

In another embodiment the particular functional group of a co-crystal former interacting with the API is specified (see for example Table I, columns labeled "Functionality" and "Molecular Structure" and the column of Table II labeled "Co-Crystal Former Functional Group"). In a further embodiment the functional group of the API interacting with the co-crystal former functional group is specified (see, for example, Tables II and III).

In another embodiment, the co-crystal comprises more than one co-crystal former. For example, two, three, four, five, or more co-crystal formers can be incorporated in a co-crystal with an API. Co-crystals which comprise two or more co-crystal formers and an API are bound together via hydrogen bonds. In one embodiment, incorporated co-crystal formers are hydrogen bonded to the API molecules. In another embodiment, co-crystal formers are hydrogen bonded to either the API molecules or the incorporated co-crystal formers.

In a further embodiment, several co-crystal formers can be contained in a single compartment, or kit, for ease in screening an API for potential co-crystal species. The co-crystal kit can comprise 5, 10, 15, 20, 25, 30, 40, 50, 60, 70, 80, 90, 100, or more of the co-crystal formers in Tables I and II. The co-crystal formers are in solid form or in solution and in an array of individual reaction vials such that individual co-crystal formers can be tested with one or more APIs by one or more crystallization methods or multiple co-crystal formers can be easily tested against one or more compounds by one or more crystallization methods. The crystallization methods include, but are not limited to, melt recrystallization, grinding, milling, standing, co-crystal formation from solution by evaporation, thermally driven crystallization from solution, co-crystal formation from solution by addition of anti-solvent, co-crystal formation from solution by vapor-diffusion, co-crystal formation from solution by drown-out, co-crystal formation from solution by any combination of the above mentioned techniques, co-crystal formation by co-sublimation, co-crystal formation by sublimation using a Knudsen cell apparatus, co-crystal formation by standing the desired components of the co-crystal in the presence of solvent vapor, co-crystal formation by slurry conversion of the desired components of the co-crystal in a solvent or mixtures of solvents, or co-crystal formation by any combination of the above techniques in the presence of additives, nucleates, crystallization enhancers, precipitants, chemical stabilizers, or antioxidants. The co-crystallization kits can be used alone or as part of larger crystallization experiments. For example, kits can be constructed as single co-crystal former single well kits, single co-crystal former multi-well kits, multi-co-crystal former single well kits, or multi-co-crystal former multi-well kits. High-throughput crystallization (e.g., the CrystalMax™ platform) can be used to construct and customize co-crystal former kits. Multi-well plates (e.g., 96 wells, 384 wells, 1536 wells, etc.), for example, can be used to store or employ an array of co-crystal formers.

In one aspect, the present invention provides a pharmaceutical co-crystal composition, comprising: an API and a co-crystal former, wherein the API is a liquid or a solid at room temperature and the co-crystal former is a solid at room temperature, and wherein the API and co-crystal former are hydrogen bonded to each other.

In a further embodiment, the API is selected from an API of Table IV of U.S. patent application Ser. No. 10/660,202, filed Sep. 11, 2003, or elsewhere herein. U.S. application Ser. No. 10/660,202, filed Sep. 11, 2003 is herein incorporated by reference in its entirety. For pharmaceuticals listed in said Table, co-crystals can comprise such APIs in free form (i.e. free acid, free base, zwitter ion), salts, solvates, hydrates, or the like. For APIs listed as salts, solvates, hydrates, and the like, the API can either be of the form listed or its corresponding free form, or of another form that is not listed. In further embodiments, the functional group of the particular API interacting with the co-crystal former is specified. A specific functional group of a co-crystal former, a specific co-crystal former, or a specified functional group or a specific co-crystal former interacting with the particular API may also be specified. It is noted that for Table II, the co-crystal former, and optionally the specific functionality, and each of the listed corresponding interacting groups are included as individual species of the present invention. Thus, each specific combination of a co-crystal former and one of the interacting groups in the same row may be specified as a species of the present invention. The same is true for other combinations as discussed in the Tables and elsewhere herein.

In another embodiment of the present invention, the co-crystal comprises an API wherein the API forms a dimeric primary amide structure via hydrogen bonds with an $R^2_2$ (8) motif. In such a structure, the $NH_2$ moiety can also participate in a hydrogen bond with a donor or an acceptor moiety from, for example, a co-crystal former or an additional (third) molecule, and the C=O moiety can participate in a hydrogen bond with a donor moiety from the co-crystal former or the additional molecule. In a further embodiment, the dimeric primary amide structure further comprises one, two, three, or four hydrogen bond donors. In a further embodiment, the dimeric primary amide structure further comprises one or two hydrogen bond acceptors. In a further embodiment, the dimeric primary amide structure further comprises a combination of hydrogen bond donors and acceptors. For example, the dimeric primary amide structure can further comprise one hydrogen bond donor and one hydrogen bond acceptor, one hydrogen bond donor and two hydrogen bond acceptors, two hydrogen bond donors and one hydrogen bond acceptor, two hydrogen bond donors and two hydrogen bond acceptors, or three hydrogen bond donors and one hydrogen bond acceptor. Two non-limiting examples of APIs which form a dimeric primary amide co-crystal structure include modafinil and carbamazepine. Some examples of APIs which include a primary amide functional group include, but are not limited to, arotinolol, atenolol, carpipramine, cefotetan, cefsulodin, docapromine, darifenacin, exalamide, fidarestat, frovatriptan, silodosin, levetiracetam, MEN-10700, mizoribine, oxcarbazepine, oxiracetam, piracetam, protirelin, TRH, ribavirin, valrecemide, temozolomide, tiazofurin, antiPARP-2, levovirin, N-benzyloxycarbonyl glycinamide, and UCB-34714.

In each process according to the invention, there is a need to contact the API with the co-crystal former. This may involve grinding or milling the two solids together or melting one or both components and allowing them to recrystallize. The use of a granulating liquid may improve or may impede co-crystal formation. Non-limiting examples of tools useful for the formation of co-crystals may include, for example, an extruder or a mortar and pestle. Further, contacting the API with the co-crystal former may also involve either solubilizing the API and adding the co-crystal former, or solubilizing the co-crystal former and adding the API. Crystallization conditions are applied to the API and co-crystal former. This may entail altering a property of the solution, such as pH or temperature and may require concentration of the solute, usually by removal of the solvent, typically by drying the solution. Solvent removal results in the concentration of both API and co-crystal former increasing over time so as to facilitate crystallization. For example, evaporation, cooling, co-sublimation, or the addition of an antisolvent may be used to crystallize co-crystals. In another embodiment, a slurry comprising an API and a co-crystal former is used to form co-crystals. Once the solid phase comprising any crystals is formed, this may be tested as described herein.

The manufacture of co-crystals on a large and/or commercial scale may be successfully completed using one or more of the processes and techniques described herein. For example, crystallization of co-crystals from a solvent and grinding or milling are conceivable non-limiting processes.

In another embodiment, the use of an excess (more than 1 molar equivalent for a 1:1 co-crystal) of a co-crystal former has been shown to drive the formation of stoichiometric co-crystals. For example, co-crystals with stoichiometries of 1:1, 2:1, or 1:2 can be produced by adding co-crystal former in an amount that is 2, 3, 4, 5, 6, 7, 8, 9, 10, 15, 20, 25, 50, 75, 100 times or more than the stoichiometric amount for a given co-crystal. Such an excessive use of a co-crystal former to form a co-crystal can be employed in solution or when grinding an API and a co-crystal former to drive co-crystal formation.

In another embodiment, the present invention provides for the use of an ionic liquid as a medium for the formation of a co-crystal, and can also be used to crystallize other forms in addition to co-crystals (e.g., salts, solvates, free acid, free base, zwitterions, etc.). This medium is useful, for example, where the above methods do not work or are difficult or impossible to control. Several non-limiting examples of ionic liquids useful in co-crystal formation are: 1-butyl-3-methylimidazolium lactate, 1-ethyl-3-methylimidazolium lactate, and 1-butylpyridinium hexafluorophosphate. The co-crystals obtained as a result of one or more of the above processes or techniques may be readily incorporated into a pharmaceutical composition by conventional means. Pharmaceutical compositions in general are discussed in further detail below and may further comprise a pharmaceutically-acceptable diluent, excipient or carrier.

In a further aspect, the present invention provides a process for the production of a pharmaceutical co-crystal, which process comprises:
  (1) providing an API which has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, imine, thiocyanate, cyanamide, oxime, nitrile diazo, organohalide, nitro, S-heterocyclic ring, thiophene, N-heterocyclic ring, pyrrole, O-heterocyclic ring, furan, epoxide, peroxide, hydroxamic acid, imidazole, and pyridine or of Table II or III;
  (2) providing a co-crystal former which has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, imine, thiocyanate, cyanamide, oxime, nitrile, diazo, organohalide, nitro, S-heterocyclic ring, thiophene, N-heterocyclic ring, pyrrole, O-heterocyclic ring, furan, epoxide, peroxide, hydroxamic acid, imidazole, and pyridine or of Table I, II, or III;
  (3) grinding, heating or contacting in solution the API with the co-crystal former under crystallization conditions; and
  (4) isolating co-crystals formed thereby.

In a specific embodiment, the API is selected from the group consisting of: carbamazepine, oxcarbazepine, glyburide, fluconazole, piracetam, stavudine, and gentisic acid. In another specific embodiment, the co-crystal former is selected from the group consisting of: 4-aminobenzoic acid, TRIS, maleic acid, gentisic acid, 4-hydroxybenzoic acid, cinnamic acid, acetylsalicylic acid, melamine, and 2-aminopyridine.

In a further aspect, the present invention provides a process for the production of a pharmaceutical composition, which process comprises:
  (1) providing an API which has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, imine, thiocyanate, cyanamide, oxime, nitrile diazo, organohalide, nitro, S-heterocyclic ring, thiophene, N-heterocyclic ring, pyrrole, O-heterocyclic ring, furan, epoxide, peroxide, hydroxamic acid, imidazole, and pyridine or of Table II or III;
  (2) providing a co-crystal former which has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, imine, thiocyanate, cyanamide, oxime, nitrile, diazo, organohalide, nitro, S-heterocyclic ring, thiophene, N-heterocyclic ring, pyrrole, O-heterocyclic ring, furan, epoxide, peroxide, hydroxamic acid, imidazole, and pyridine or of Table I, II, or III;
  (3) grinding, heating or contacting in solution the API with the co-crystal former under crystallization conditions;
  (4) isolating co-crystals formed thereby; and
  (5) incorporating the co-crystals into a pharmaceutical composition.

In a still further aspect the present invention provides a process for the production of a pharmaceutical composition, which comprises:
  (1) grinding, heating or contacting in solution an API with a co-crystal former, under crystallization conditions, so as to form a solid phase;
  (2) isolating co-crystals comprising the API and the co-crystal former; and
  (3) incorporating the co-crystals into a pharmaceutical composition.

Assaying the solid phase for the presence of co-crystals of the API and the co-crystal former may be carried out by conventional methods known in the art. For example, it is convenient and routine to use powder X-ray diffraction techniques to assess the presence of co-crystals. This may be affected by comparing the diffractograms of the API, the crystal former and putative co-crystals in order to establish whether or not true co-crystals have been formed. Other techniques, used in an analogous fashion, include differential scanning calorimetry (DSC), thermogravimetric analysis (TGA), solid state NMR spectroscopy, and Raman spectroscopy. Single crystal X-ray diffraction is especially useful in identifying co-crystal structures.

Some of the APIs and co-crystal formers of the present invention have one or more chiral centers and may exist in a variety of stereoisomeric configurations. As a consequence of these chiral centers, several APIs and co-crystal formers of the present invention occur as racemates, mixtures of enantiomers and as individual enantiomers, as well as diastereomers and mixtures of diastereomers. All such racemates, enantiomers, and diastereomers are within the scope of the present invention including, for example, cis- and trans-isomers, R- and S-enantiomers, and (D)- and (L)-isomers. Co-crystals of the present invention can include isomeric forms of either the API or the co-crystal former or both. Isomeric forms of APIs and co-crystal formers include, but are not limited to, stereoisomers such as enantiomers and diastereomers. In one embodiment, a co-crystal can comprise a racemic API and/or co-crystal former. In another embodiment, a co-crystal can comprise an enantiomerically pure API and/or co-crystal former. In another embodiment, a co-crystal can comprise an API or a co-crystal former with an enantiomeric excess of about 50 percent, 55 percent, 60 percent, 65 percent, 70 percent, 75 percent, 80 percent, 85 percent, 90 percent, 95 percent, 96 percent, 97 percent, 98 percent, 99 percent, greater than 99 percent, or any intermediate value. Several non-limiting examples of stereoisomeric APIs include modafinil, cis-itraconazole, ibuprofen, and flurbiprofen. Several non-limiting examples of stereoisomeric co-crystal formers include tartaric acid and malic acid.

Co-crystals comprising enantiomerically pure components (e.g., API or co-crystal former) can give rise to chemical and/or physical properties which are modulated with respect to those of the corresponding co-crystal comprising a racemic component. A co-crystal comprising an enantiomerically pure component can give rise to a modulation of, for example, activity, bioavailability, or solubility, with respect to the corresponding co-crystal comprising a racemic component.

As used herein and unless otherwise noted, the term "racemic co-crystal" refers to a co-crystal which is comprised of an equimolar mixture of two enantiomers of the API, the co-crystal former, or both. For example, a co-crystal comprising a stereoisomeric API and a non-stereoisomeric co-crystal former is a "racemic co-crystal" when there is present an equimolar mixture of the API enantiomers. Similarly, a co-crystal comprising a non-stereoisomeric API and a stereoisomeric co-crystal former is a "racemic co-crystal" when there is present an equimolar mixture of the co-crystal former enantiomers. In addition, a co-crystal comprising a stereoisomeric API and a stereoisomeric co-crystal former is a "racemic co-crystal" when there is present an equimolar mixture of the API enantiomers and of the co-crystal former enantiomers.

As used herein and unless otherwise noted, the term "enantiomerically pure co-crystal" refers to a co-crystal which is comprised of a stereoisomeric API or a stereoisomeric co-crystal former or both where the enantiomeric excess of the stereoisomeric species is greater than or equal to about 90 percent ee.

In another embodiment, the present invention includes a pharmaceutical composition comprising a co-crystal with an enantiomerically pure API or co-crystal former wherein the bioavailability is modulated with respect to the racemic co-crystal.

In another embodiment, the present invention includes a pharmaceutical composition comprising a co-crystal with an enantiomerically pure API or co-crystal former wherein the activity is modulated with respect to the racemic co-crystal. In another embodiment, the present invention includes a pharmaceutical composition comprising a co-crystal with an enantiomerically pure API or co-crystal former wherein the solubility is modulated with respect to the racemic co-crystal.

As used herein, the term "enantiomerically pure" includes a composition which is substantially enantiomerically pure and includes, for example, a composition with greater than or equal to about 90, 91, 92, 93, 94, 95, 96, 97, 98, or 99 percent enantiomeric excess.

In one embodiment, the present invention provides a co-crystal comprising carbamazepine and 4-aminobenzoic acid. In another embodiment, the present invention provides a co-crystal comprising carbamazepine, 4-aminobenzoic acid, and water.

In another embodiment, the present invention provides a co-crystal comprising glyburide and TRIS. In another embodiment, the present invention provides a co-crystal comprising fluconazole maleate and maleic acid. In another embodiment, the present invention provides a co-crystal comprising piracetam. In another embodiment, the present invention provides a co-crystal comprising piracetam and gentisic acid. In another embodiment, the present invention provides a co-crystal comprising piracetam and 4-hydroxybenzoic acid. In another embodiment, the present invention provides a co-crystal comprising carbamazepine and acetylsalicylic acid. In another embodiment, the present invention provides a co-crystal comprising carbamazepine and cinnamic acid. In another embodiment, the present invention provides a co-crystal comprising stavudine. In another embodiment, the present invention provides a co-crystal comprising stavudine and melamine. In another embodiment, the present invention provides a co-crystal comprising stavudine and 2-aminopyridine. In another embodiment, the present invention further comprises a formic acid solvate of oxcarbazepine.

Solubility Modulation

In a further aspect, the present invention provides a process for modulating the solubility of an API, which process comprises:
(1) grinding, heating, co-subliming, co-melting, or contacting in solution the API with a co-crystal former under crystallization conditions, so as to form a co-crystal of the API and the co-crystal former; and
(2) isolating co-crystals comprising the API and the co-crystal former.

In one embodiment, the solubility of the API is modulated such that the aqueous solubility is increased. Solubility of APIs may be measured by any conventional means such as chromatography (e.g., HPLC) or spectroscopic determination of the amount of API in a saturated solution of the API, such as UV-spectroscopy, IR-spectroscopy, Raman spectroscopy, quantitative mass spectroscopy, or gas chromatography.

In another aspect of the invention, the API may have low aqueous solubility. Typically, low aqueous solubility in the present application refers to a compound having a solubility in water which is less than or equal to 10 mg/mL, when measured at 37 degrees C., and preferably less than or equal to 5 mg/mL or 1 mg/mL. Low aqueous solubility can further be specifically defined as less than or equal to 900, 800, 700, 600, 500, 400, 300, 200 150 100, 90, 80, 70, 60, 50, 40, 30, 20 micrograms/mL, or further 10, 5 or 1 micrograms/mL, or further 900, 800, 700, 600, 500, 400, 300, 200 150, 100 90, 80, 70, 60, 50, 40, 30, 20, or 10 ng/mL, or less than 10 ng/mL when measured at 37 degrees C. Aqueous solubility can also be specified as less than 500, 400, 300, 200, 150, 100, 75, 50 or 25 mg/mL. As embodiments of the present invention, solubility can be increased 2, 3, 4, 5, 7, 10, 15, 20, 25, 50, 75, 100, 200, 300, 500, 750, 1000, 5000, or 10,000 times by making a co-crystal of the reference form (e.g., crystalline or amorphous free acid, free base or zwitter ion, hydrate or solvate), or a salt thereof. Further aqueous solubility can be measured in simulated gastric fluid (SGF) or simulated intestinal fluid (SIF) rather than water. SGF (non-diluted) of the present invention is made by combining 1 g/L Triton X-100 and 2 g/L NaCl in water and adjusting the pH with 20 mM HCl to obtain a solution with a final pH=1.7 (SIF is 0.68% monobasic potassium phosphate, 1% pancreatin, and sodium hydroxide where the pH of the final solution is 7.5). The pH of the solvent used may also be specified as 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 11.5, 12, 12.5, 13, 13.5, or 14 or any pH in between successive values.

Examples of embodiments includes: co-crystal compositions with an aqueous solubility, at 37 degrees C. and a pH of 7.0, that is increased at least 5 fold over the reference form, co-crystal compositions with a solubility in SGF that is increased at least 5 fold over the reference form, co-crystal compositions with a solubility in SIF that is increased at least 5 fold over the reference form.

Dissolution Modulation

In another aspect of the present invention, the dissolution profile of the API is modulated whereby the aqueous dissolution rate or the dissolution rate in simulated gastric fluid or in simulated intestinal fluid, or in a solvent or plurality of solvents is increased. Dissolution rate is the rate at which API solids dissolve in a dissolution medium. For APIs whose absorption rates are faster than the dissolution rates (e.g., steroids), the rate-limiting step in the absorption process is often the dissolution rate. Because of a limited residence time at the absorption site, APIs that are not dissolved before they are removed from intestinal absorption site are considered useless. Therefore, the rate of dissolution has a major impact on the performance of APIs that are poorly soluble. Because of this factor, the dissolution rate of APIs in solid dosage forms is an important, routine, quality control parameter used in the API manufacturing process.

Dissolution rate=$K \, S(C_S-C)$ where K is dissolution rate constant, S is the surface area, $C_S$ is the apparent solubility, and C is the concentration of API in the dissolution medium. For rapid API absorption, $C_S-C$ is approximately equal to $C_S$. The dissolution rate of APIs may be measured by conventional means known in the art.

The increase in the dissolution rate of a co-crystal, as compared to the reference form (e.g., free form or salt), may be specified, such as by 10, 20, 30, 40, 50, 60, 70, 80, 90, or 100%, or by 2, 3, 4, 5, 6, 7, 8, 9, 10, 15, 20, 25, 30, 40, 50, 75, 100, 125, 150, 175, 200, 250, 300, 350, 400, 500, 1000, 10,000, or 100,000 fold greater than the reference form (e.g., free form or salt form) in the same solution. Conditions under which the dissolution rate is measured is the same as discussed above The increase in dissolution may be further specified by the time the composition remains supersaturated before reaching equilibrium solubility.

Examples of above embodiments include: co-crystal compositions with a dissolution rate in aqueous solution, at 37 degrees C. and a pH of 7.0, that is increased at least 5 fold over the reference form, co-crystal compositions with a dissolution rate in SGF that is increased at least 5 fold over the reference form, co-crystal compositions with a dissolution rate in SIF that is increased at least 5 fold over the reference form.

Bioavailability Modulation

The methods of the present invention are used to make a pharmaceutical API formulation with greater solubility, dissolution, and bioavailability. Bioavailability can be improved via an increase in AUC, reduced time to $T_{max}$, (the time to reach peak blood serum levels), or increased $C_{max}$. The present invention can result in higher plasma concentrations of API when compared to the neutral form or salt alone (reference form).

AUC is the area under the plot of plasma concentration of API (not logarithm of the concentration) against time after API administration. The area is conveniently determined by the "trapezoidal rule": The data points are connected by straight line segments, perpendiculars are erected from the abscissa to each data point, and the sum of the areas of the triangles and trapezoids so constructed is computed. When the last measured concentration ($C_n$, at time $t_n$) is not zero, the AUC from $t_n$ to infinite time is estimated by $C_n/k_{el}$.

The AUC is of particular use in estimating bioavailability of APIs, and in estimating total clearance of APIs ($Cl_T$). Following single intravenous doses, $AUC=D/Cl_T$, for single compartment systems obeying first-order elimination kinetics, where D is the dose; alternatively, $AUC=C_0/k_{el}$, where $k_{el}$ is the API elimination rate constant. With routes other than the intravenous, for such systems, $AUC=F \cdot D/Cl_T$, where F is the absolute bioavailability of the API.

Thus, in a further aspect, the present invention provides a process for modulating the bioavailability of an API when administered in its normal and effective dose range as a co-crystal, whereby the AUC is increased, the time to $T_{max}$ is reduced, or $C_{max}$ is increased, as compared to a reference form, which process comprises:

(1) grinding, heating, co-subliming, co-melting, or contacting in solution the API with a co-crystal former under crystallization conditions, so as to form a co-crystal of the API and the co-crystal former; and (2) isolating co-crystals comprising the API and the co-crystal former.

Examples of the above embodiments include: co-crystal compositions with a time to $T_{max}$ that is reduced by at least 10% as compared to the reference form, co-crystal compositions with a time to $T_{max}$ that is reduced by at least 20% over the reference form, co-crystal compositions with a time to $T_{max}$ that is reduced by at least 40% over the reference form, co-crystal compositions with a time to $T_{max}$ that is reduced by at least 50% over the reference form, co-crystal compositions with a $T_{max}$ that is reduced by at least 60% over the reference form, co-crystal compositions with a $T_{max}$ that is reduced by at least 70% over the reference form, co-crystal compositions with a $T_{max}$ that is reduced by at least 80% over the reference form, co-crystal compositions with a $T_{max}$ that is reduced by at least 90% over the reference form, co-crystal compositions with a $C_{max}$ that is increased by at least 20% over the reference form, co-crystal compositions with a $C_{max}$ that is increased by at least 30% over the reference form, co-crystal compositions with a $C_{max}$ that is increased by at least 40% over the reference form, co-crystal compositions with a $C_{max}$ that is increased by at least 50% over the reference form, co-crystal compositions with a $C_{max}$ that is increased by at least 60% over the reference form, co-crystal compositions with a $C_{max}$ that is increased by at least 70% over the reference form, co-crystal compositions with a $C_{max}$ that is increased by at least 80% over the reference form, co-crystal compositions with a Cmax that is increased by at least 2 fold, 3 fold, 5 fold, 7.5 fold, 10 fold, 25 fold, 50 fold or 100 fold, co-crystal compositions with an AUC that is increased by at least 10% over the reference form, co-crystal compositions with an AUC that is increased by at least 20% over the reference form, co-crystal compositions with an AUC that is increased by at least 30% over the reference form, co-crystal compositions with an AUC that is increased by at least 40% over the reference form, co-crystal compositions with an AUC that is increased by at least 50% over the reference form, co-crystal compositions with an AUC that is increased by at least 60% over the reference form, co-crystal compositions with an AUC that is increased by at least 70% over the reference form, co-crystal compositions with an AUC that is increased by at least 80% over the reference form or co-crystal compositions with an AUC that is increased by at least 2 fold, 3 fold, 4 fold, 5 fold, 6 fold, 7 fold, 8 fold, 9 fold, or 10 fold. Other examples include wherein the reference form is crystalline, wherein the reference form is amorphous, wherein the reference form is an anhydrous crystalline sodium salt, or wherein the reference form is an anhydrous crystalline HCl salt.

Dose Response Modulation

In a further aspect the present invention provides a process for improving the dose response of an API, which process comprises:

(1) grinding, heating, co-subliming, co-melting, or contacting in solution an API with a co-crystal former under crystallization conditions, so as to form a co-crystal of the API and the co-crystal former; and (2) isolating co-crystals comprising the API and the co-crystal former.

Dose response is the quantitative relationship between the magnitude of response and the dose inducing the response and may be measured by conventional means known in the art. The curve relating effect (as the dependent variable) to dose (as the independent variable) for an API-cell system is the "dose-response curve". Typically, the dose-response curve is the measured response to an API plotted against the dose of the API (mg/kg) given. The dose response curve can also be a curve of AUC against the dose of the API given.

In an embodiment of the present invention, a co-crystal of the present invention has an increased dose response curve or a more linear dose response curve than the corresponding reference compound.

Increased Stability

In a still further aspect the present invention provides a process for improving the stability of an API (as compared to a reference form such as its free form or a salt thereof), which process comprises:
(1) grinding, heating, co-subliming, co-melting, or contacting in solution the pharmaceutical salt with a co-crystal former under crystallization conditions, so as to form a co-crystal of the API and the co-crystal former; and
(2) isolating co-crystals comprising the API and the co-crystal former.

In a preferred embodiment, the compositions of the present invention, including the API or active pharmaceutical ingredient (API) and formulations comprising the API, are suitably stable for pharmaceutical use. Preferably, the API or formulations thereof of the present invention are stable such that when stored at 30 degrees C. for 2 years, less than 0.2% of any one degradant is formed. The term degradant refers herein to product(s) of a single type of chemical reaction. For example, if a hydrolysis event occurs that cleaves a molecule into two products, for the purpose of the present invention, it would be considered a single degradant. More preferably, when stored at 40 degrees C. for 2 years, less than 0.2% of any one degradant is formed. Alternatively, when stored at 30 degrees C. for 3 months, less than 0.2% or 0.15%, or 0.1% of any one degradant is formed, or when stored at 40 degrees C. for 3 months, less than 0.2% or 0.15%, or 0.1% of any one degradant is formed. Further alternatively, when stored at 60 degrees C. for 4 weeks, less than 0.2% or 0.15%, or 0.1% of any one degradant is formed. The relative humidity (RH) may be specified as ambient (RH), 75% (RH), or as any single integer between 1 to 99%.

Difficult to Salt or Unsaltable Compounds

In a still further aspect the present invention provides a process for making co-crystals of unsaltable or difficult to salt APIs which process comprises:
(1) grinding, heating, co-subliming, co-melting, or contacting in solution an API with a co-crystal former under crystallization conditions, so as to form a co-crystal of the API and the co-crystal former; and
(2) isolating co-crystals comprising the API and the co-crystal former.

Difficult to salt compounds include bases with a pKa less than 3 or acids with a pKa greater than 10. Zwitter ions are also difficult to salt or unsaltable compounds according to the present invention.

Decreasing Hygroscopicity

In a still further aspect, the present invention provides a method for decreasing the hygroscopicity of an API, which method comprises:
(1) grinding, heating, co-subliming, co-melting, or contacting in solution the API with a co-crystal former under crystallization conditions, so as to form a co-crystal of the API and the co-crystal former; and
(2) isolating co-crystals comprising the API and the co-crystal former.

An aspect of the present invention provides a pharmaceutical composition comprising a co-crystal of an API that is less hygroscopic than amorphous or crystalline, free form or salt (including metal salts such as sodium, potassium, lithium, calcium, magnesium) or another reference compound. Hygroscopicity can be assessed by dynamic vapor sorption analysis, in which 5-50 mg of the compound is suspended from a Cahn microbalance. The compound being analyzed should be placed in a non-hygroscopic pan and its weight should be measured relative to an empty pan composed of identical material and having nearly identical size, shape, and weight. Ideally, platinum pans should be used. The pans should be suspended in a chamber through which a gas, such as air or nitrogen, having a controlled and known percent relative humidity (% RH) is flowed until equilibrium criteria are met. Typical equilibrium criteria include weight changes of less than 0.01% over 3 minutes at constant humidity and temperature. The relative humidity should be measured for samples dried under dry nitrogen to constant weight (<0.01% change in 3 minutes) at 40 degrees C. unless doing so would de-solvate or otherwise convert the material to an amorphous compound. In one aspect, the hygroscopicity of a dried compound can be assessed by increasing the RH from 5 to 95% in increments of 5% RH and then decreasing the RH from 95 to 5% in 5% increments to generate a moisture sorption isotherm. The sample weight should be allowed to equilibrate between each change in % RH. If the compound deliquesces or becomes amorphous above 75% RH, but below 95% RH, the experiment should be repeated with a fresh sample and the relative humidity range for the cycling should be narrowed to 5-75% RH or 10-75% RH, instead of 5-95% RH. If the sample cannot be dried prior to testing due to lack of form stability, than the sample should be studied using two complete humidity cycles of either 10-75% RH or 5-95% RH, and the results of the second cycle should be used if there is significant weight loss at the end of the first cycle.

Hygroscopicity can be defined using various parameters. For purposes of the present invention, a non-hygroscopic molecule should not gain or lose more than 1.0%, or more preferably, 0.5% weight at 25 degrees C. when cycled between 10 and 75% RH (relative humidity at 25 degrees C.). The non-hygroscopic molecule more preferably should not gain or lose more than 1.0%, or more preferably, 0.5% weight when cycled between 5 and 95% RH at 25 degrees C., or more than 0.25% of its weight between 10 and 75% RH. Most preferably, a non-hygroscopic molecule will not gain or lose more than 0.25% of its weight when cycled between 5 and 95% RH.

Alternatively, for purposes of the present invention, hygroscopicity can be defined using the parameters of Callaghan et al., "Equilibrium moisture content of pharmaceutical excipients", in Api Dev. Ind. Pharm., Vol. 8, pp. 335-369 (1982). Callaghan et al. classified the degree of hygroscopicity into four classes.

Class 1: Non-hygroscopic Essentially no moisture increases occur at relative humidities below 90%.

Class 2: Slightly hygroscopic Essentially no moisture increases occur at relative humidities below 80%.

Class 3: Moderately hygroscopic Moisture content does not increase more than 5% after storage for 1 week at relative humidities below 60%.

Class 4: Very hygroscopic Moisture content increase may occur at relative humidities as low as 40 to 50%.

Alternatively, for purposes of the present invention, hygroscopicity can be defined using the parameters of the European Pharmacopoeia Technical Guide (1999, p. 86) which has defined hygrospocity, based on the static method, after storage at 25 degrees C. for 24 hours at 80% RH:

Slightly hygroscopic: Increase in mass is less than 2 percent m/m and equal to or greater than 0.2 percent m/m.

Hygroscopic: Increase in mass is less than 15 percent m/m and equal to or greater than 0.2 percent m/m.

Very Hygroscopic: Increase in mass is equal to or greater than 15 percent m/m.

Deliquescent: Sufficient water is absorbed to form a liquid.

Co-crystals of the present invention can be set forth as being in Class 1, Class 2, or Class 3, or as being Slightly hygroscopic, Hygroscopic, or Very Hygroscopic. Co-crystals of the present invention can also be set forth based on their ability to reduce hygroscopicity. Thus, preferred co-crystals of the present invention are less hygroscopic than a reference compound. The reference compound can be specified as the API in free form (free acid, free base, hydrate, solvate, etc.) or salt (e.g., especially metal salts such as sodium, potassium, lithium, calcium, or magnesium). Further included in the present invention are co-crystals that do not gain or lose more than 1.0% weight at 25 degrees C. when cycled between 10 and 75% RH, wherein the reference compound gains or loses more than 1.0% weight under the same conditions. Further included in the present invention are co-crystals that do not gain or lose more than 0.5% weight at 25 degrees C. when cycled between 10 and 75% RH, wherein the reference compound gains or loses more than 0.5% or more than 1.0% weight under the same conditions. Further included in the present invention are co-crystals that do not gain or lose more than 1.0% weight at 25 degrees C. when cycled between 5 and 95% RH, wherein the reference compound gains or loses more than 1.0% weight under the same conditions. Further included in the present invention are co-crystals that do not gain or lose more than 0.5% weight at 25 degrees C. when cycled between 5 and 95% RH, wherein the reference compound gains or loses more than 0.5% or more than 1.0% weight under the same conditions. Further included in the present invention are co-crystals that do not gain or lose more than 0.25% weight at 25 degrees C. when cycled between 5 and 95% RH, wherein the reference compound gains or loses more than 0.5% or more than 1.0% weight under the same conditions.

Further included in the present invention are co-crystals that have a hygroscopicity (according to Callaghan et al.) that is at least one class lower than the reference compound or at least two classes lower than the reference compound. Included are a Class 1 co-crystal of a Class 2 reference compound, a Class 2 co-crystal of a Class 3 reference compound, a Class 3 co-crystal of a Class 4 reference compound, a Class 1 co-crystal of a Class 3 reference compound, a Class 1 co-crystal of a Class 4 reference compound, or a Class 2 co-crystal of a Class 4 reference compound.

Further included in the present invention are co-crystals that have a hygroscopicity (according to the European Pharmacopoeia Technical Guide) that is at least one class lower than the reference compound or at least two classes lower than the reference compound. Non-limiting examples include; a slightly hygroscopic co-crystal of a hygroscopic reference compound, a hygroscopic co-crystal of a very hygroscopic reference compound, a very hygroscopic co-crystal of a deliquescent reference compound, a slightly hygroscopic co-crystal of a very hygroscopic reference compound, a slightly hygroscopic co-crystal of a deliquescent reference compound, and a hygroscopic co-crystal of a deliquescent reference compound.

Crystallizing Amorphous Compounds

In a further aspect, the present invention provides a process for crystallizing an amorphous compound, which process comprises:
(1) grinding, heating, co-subliming, co-melting, or contacting in solution the API with a co-crystal former under crystallization conditions, so as to form a co-crystal of the API and the co-crystal former; and
(2) isolating co-crystals comprising the API and the co-crystal former.

An amorphous compound includes compounds that do not crystallize using routine methods in the art.

Decreasing Form Diversity

In a still further embodiment aspect the present invention provides a process for reducing the form diversity of an API, which process comprises:
(1) grinding, heating, co-subliming, co-melting, or contacting in solution the API with a co-crystal former under crystallization conditions, so as to form a co-crystal of the API and the co-crystal former; and
(2) isolating co-crystals comprising the API and the co-crystal former.

For purposes of the present invention, the number of forms of a co-crystal is compared to the number of forms of a reference compound (e.g. the free form or a salt of the API) that can be made using routine methods in the art. For example, an API (e.g., piracetam) which has two or more known polymorphs and a co-crystal comprising piracetam which exists in at least one fewer forms than the parent API.

Morphology Modulation

In a still further aspect the present invention provides a process for modifying the morphology of an API, which process comprises:
(1) grinding, heating, co-subliming, co-melting, or contacting in solution the API with a co-crystal former under crystallization conditions, so as to form a co-crystal of the API and the co-crystal former; and
(2) isolating co-crystals comprising the API and the co-crystal former.

In one embodiment the co-crystal comprises or consists of a co-crystal former and an API wherein the interaction between the two, e.g., H-bonding, occurs between a functional group of Table III of an API with a corresponding interacting group of Table III. In a further embodiment, the co-crystal comprises a co-crystal former of Table I or II and an API with a corresponding interacting group of Table III. In a further embodiment the co-crystal comprises an API and a co-crystal former with a functional group of Table III. In a further embodiment, the co-crystal is from Table I or II. In an aspect of the invention, only co-crystals having an H-bond acceptor on the first molecule and an H-bond donor on the second molecule, where the first and second molecules are either co-crystal former and API respectively or API and co-crystal former respectively, are included in the present invention.

In another embodiment, the co-crystal former and API each have only one H-bond donor/acceptor. In another aspect, the molecular weight of the API is less than 2000, 1500, 1000, 750, 500, 350, 200, or 150 Daltons. In another embodiment, the molecular weight of the API is between 100-200, 200-300, 300-400, 400-500, 500-600, 600-700, 700-800, 800-900, 900-1000, 1000-1200, 1200-1400, 1400-1600, 1600-1800, or 1800-2000. APIs with the above molecular weights may also be specifically excluded from the present invention.

As used herein, the term "supramolecular synthon" refers to the sum of the components of a multi-component non-covalent interaction, wherein the non-covalent interaction contributes to the formation of a discrete supramolecular entity or polymeric structure, wherein each component is a chemical functionality. A supramolecular synthon can be, for example, a dimer, trimer, catemer, or n-mer. Supramolecular synthons between identical groups or chemical functionalities (e.g., acid-acid) in similar, identical, or different molecules are termed "homosynthons." Supramolecular synthons between different groups or chemical functionalities (e.g., acid-amide) in similar, identical, or different molecules are termed "heterosynthons."

The hydrogen bond donor moieties of a co-crystal can include, but are not limited to, any one, any two, any three, any four, or more of the following: amino-pyridine, primary amine, secondary amine, sulfonamide, primary amide, secondary amide, alcohol, and carboxylic acid. The hydrogen bond acceptor moieties of a co-crystal can include, but are not limited to, any one, any two, any three, any four, or more of the following: amino-pyridine, primary amine, secondary amine, sulfonamide, primary amide, secondary amide, alcohol, carboxylic acid, carbonyl, cyano, dimethoxyphenyl, sulfonyl, aromatic nitrogen (6 membered ring), ether, chloride, organochloride, bromide, organobromide, and organoiodide. Hydrogen bonds are known to form many supramolecular structures including, but not limited to, a catemer, a dimer, a trimer, a tetramer, or a higher order structure. Tables IV-XX list specific hydrogen bond donor and acceptor moieties and their approximate interaction distances from the electromagnetic donor atom through the hydrogen atom to the electromagnetic acceptor atom. For example, Table IV lists functional groups that are known to hydrogen bond with amino-pyridines. Amino-pyridines comprise two distinct sites of hydrogen bond donation/acceptance. Both the aromatic nitrogen atom (Npy) and the amine group ($NH_2$) can participate in hydrogen bonds. The ability of a given functional group to participate in a hydrogen bond as a donor or as an acceptor or both can be determined by inspection by those skilled in the art.

The data included in Tables IV-XX are taken from an analysis of solid-state structures as reported in the Cambridge Structural Database (CSD). These data include a number of hydrogen bonding interactions between many functional groups and their associated interaction distances.

TABLE IV

Hydrogen bonding functional groups with amino-pyridines and associated interaction distances

| Functional Group | Interaction Distances (angstroms) | Mean | Standard Deviation |
|---|---|---|---|
| Catemer | 2.8-3.2 | 2.99 | 0.08 |
| Dimer | 2.9-3.25 | 3.05 | 0.06 |
| Primary Amide (to $NH_2$) | 3.07 | N/A | N/A |
| Primary Amide (to Npy) | 2.97 | N/A | N/A |
| Secondary Amide (to $NH_2$) | 2.75-3.17 | N/A | N/A |
| Secondary Amide (to Npy) | 2.70-3.20 | 2.92 | 0.07 |
| Carboxylic Acid (to $NH_2$) | 2.72-3.07 | 2.89 | 0.08 |
| Carboxylic Acid (to Npy) | 2.54-2.82 | 2.67 | 0.05 |
| Water (to $NH_2$) | 2.72-3.15 | 2.94 | 0.09 |
| Water (to Npy) | 2.65-3.15 | 2.87 | 0.10 |
| Alcohol (to $NH_2$) | 2.78-3.14 | 2.96 | 0.08 |
| Alcohol (to Npy) | 2.63-3.06 | 2.79 | 0.07 |
| Primary Amine | 2.85-3.25 | 3.05 | 0.07 |
| Secondary Amine | 2.83-3.25 | 2.93 | 0.05 |
| Carbonyl | 2.87-3.10 | 2.95 | 0.07 |
| Sulfoxo | 2.70-3.10 | 2.90 | 0.08 |
| Ether | 2.84-3.20 | 3.05 | 0.07 |
| Ester (C—O—C) | 3.09 | N/A | N/A |
| Ester (C═O) | 2.85-3.16 | 3.00 | 0.08 |

TABLE IV-continued

Hydrogen bonding functional groups with amino-pyridines and associated interaction distances

| Functional Group | Interaction Distances (angstroms) | Mean | Standard Deviation |
|---|---|---|---|
| Aromatic N | 2.78-3.25 | 3.04 | 0.07 |
| Cyano | 2.83-3.30 | 3.09 | 0.12 |
| Nitro | 2.85-3.28 | 3.08 | 0.11 |
| Chloride | 3.10-3.45 | 3.25 | 0.08 |
| Bromide | 3.27-3.48 | 3.39 | 0.05 |

TABLE V

Hydrogen bonding functional groups with primary amines and associated interaction distances

| Functional Group | Interaction Distances (angstroms) | Mean | Standard Deviation |
|---|---|---|---|
| Catemer | 2.69-3.15 | 3.07 | 0.09 |
| Primary Amide | 2.73-3.20 | 2.98 | 0.13 |
| Secondary Amide | 2.65-3.20 | 2.97 | 0.09 |
| Carboxylic Acid (O═C) | 2.74-3.15 | 2.94 | 0.09 |
| Carboxylic Acid (OH) | 2.72-3.12 | 2.95 | 0.11 |
| Amino-pyridine | 3.10-3.24 | 3.22 | 0.02 |
| Sulfonamide | 2.86-3.17 | 3.02 | 0.11 |
| Water | 2.65-3.17 | 2.95 | 0.10 |
| Alcohol | 2.63-3.26 | 2.98 | 0.15 |
| Carbonyl | 2.64-3.15 | 2.95 | 0.09 |
| Sulfoxo | 2.70-3.10 | 2.92 | 0.09 |
| Sulfonyl | 2.93-3.12 | 3.13 | 0.12 |
| Ether | 2.75-3.25 | 3.05 | 0.11 |
| Ester (C—O—C) | 2.90-3.20 | 3.11 | 0.07 |
| Ester (O═C) | 2.74-3.27 | 3.04 | 0.12 |
| Aromatic N | 2.92-3.26 | 3.07 | 0.07 |
| Cyano | 2.83-3.30 | 3.02 | 0.06 |
| Nitro | 2.75-3.17 | 3.05 | 0.08 |
| Chloride | 3.07-3.50 | 3.28 | 0.09 |
| Bromide | 3.23-3.60 | 3.43 | 0.08 |

TABLE VI

Hydrogen bonding functional groups with primary sulfonamides and associated interaction distances

| Functional Group | Interaction Distances (angstroms) | Mean | Standard Deviation |
|---|---|---|---|
| Catemer | 0-3.3 | 3.02 | N/A |
| Dimer | 0-3.22 | 3.04 | N/A |
| Water | 2.87 | N/A | N/A |
| Alcohol | 2.85-3.07 | 2.94 | 0.06 |
| Primary Amine | 2.85-3.20 | 3.02 | 0.10 |
| Secondary Amine | 2.85-3.20 | 3.03 | 0.10 |
| Sulfonyl | 2.85-3.20 | 3.03 | 0.12 |
| Ether | 2.90-3.20 | 3.07 | 0.08 |
| Ester | 2.85-3.12 | 2.99 | 0.07 |
| Cyano | 3.00 | N/A | N/A |
| Nitro | 3.00-3.20 | 3.12 | 0.07 |
| Chloride | 3.20-3.32 | 3.26 | 0.03 |

TABLE VII

Hydrogen bonding functional groups with primary amides and associated interaction distances

| Functional Group | Interaction Distances (angstroms) | Mean | Standard Deviation |
|---|---|---|---|
| Catemer | 2.70-3.10 | 2.940 | 0.05 |
| Dimer | 2.70-3.15 | 2.949 | 0.05 |

TABLE VII-continued

Hydrogen bonding functional groups with primary amides and associated interaction distances

| Functional Group | Interaction Distances (angstroms) | Mean | Standard Deviation |
|---|---|---|---|
| Secondary Amide | 2.70-3.15 | 2.935 | 0.07 |
| Carboxylic Acid (OH) | 2.40-2.80 | 2.560 | 0.06 |
| Carboxylic Acid (C=O) | 2.80-3.25 | 2.961 | 0.09 |
| Amino-pyridine (NH$_2$) | 2.90-3.20 | 3.069 | 0.00 |
| Amino-pyridine (Aromatic N) | 2.80-3.10 | 2.972 | 0.00 |
| Aromatic N | 2.90-3.21 | 3.069 | 0.07 |
| Water (to C=O) | 2.60-3.00 | 2.813 | 0.08 |
| Water (to NH$_2$) | 2.70-3.07 | 2.945 | 0.07 |
| Alcohol (to C=O) | 2.50-3.00 | 2.753 | 0.07 |
| Alcohol (to NH$_2$) | 2.70-3.10 | 2.965 | 0.06 |
| Secondary Amine (to C=O) | 2.80-3.10 | 2.967 | 0.07 |
| Secondary Amine (to NH$_2$) | 3.00-3.15 | 3.079 | 0.03 |
| Carbonyl | 2.80-3.15 | 2.993 | 0.08 |
| Sulfonyl | 2.90-3.00 | 2.920 | 0.00 |
| Ether | 2.80-3.10 | 2.960 | 0.07 |
| Ester (C=O) | 2.70-3.05 | 2.932 | 0.05 |
| Cyano | 3.00-3.30 | 3.117 | 0.07 |
| Nitro | 2.90-3.07 | 3.020 | 0.03 |
| Chloride | 3.10-3.60 | 3.340 | 0.08 |
| Bromide | 3.30-3.80 | 3.550 | 0.11 |

TABLE VIII

Hydrogen bonding functional groups with secondary amides and associated interaction distances

| Functional Group | Interaction Distances (angstroms) | Mean | Standard Deviation |
|---|---|---|---|
| Catemer | 2.60-3.10 | 2.899 | 0.07 |
| Dimer | 2.60-3.10 | 2.872 | 0.06 |
| Primary Amide | 2.70-3.15 | 2.935 | 0.07 |
| Carboxylic Acid (C=O) | 2.70-3.10 | 2.920 | 0.09 |
| Carboxylic Acid (OH) | 2.40-3.05 | 2.606 | 0.05 |
| Amino-pyridine (Aromatic N) | 2.70-3.20 | 2.920 | 0.07 |
| Amino-pyridine (NH$_2$) | 2.75-3.17 | 2.920 | 0.08 |
| Sulfonamide (S=O) | 2.80-3.20 | 3.110 | 0.16 |
| Sulfonamide (NH$_2$) | 2.70-3.00 | 2.916 | 0.05 |
| Aromatic N | 2.60-3.15 | 2.955 | 0.09 |
| Water (to C=O) | 2.40-3.10 | 2.840 | 0.09 |
| Water (to NH$_2$) | 2.60-3.10 | 2.887 | 0.10 |
| Alcohol (to C=O) | 2.50-3.04 | 2.773 | 0.09 |
| Alcohol (to NH$_2$) | 2.50-3.20 | 2.933 | 0.11 |
| Primary Amine | 2.65-3.20 | 2.970 | 0.09 |
| Secondary Amine | 2.60-3.15 | 2.932 | 0.11 |
| Carbonyl | 2.70-3.07 | 2.937 | 0.08 |
| Sulfonyl | 2.60-3.25 | 3.080 | 0.09 |
| Ether | 2.70-3.16 | 2.992 | 0.09 |
| Ester | 2.80-3.16 | 2.986 | 0.09 |
| Cyano | 2.90-3.30 | 3.120 | 0.09 |
| Nitro | 2.80-3.10 | 2.993 | 0.08 |
| Chloride | 2.90-3.40 | 3.261 | 0.15 |
| Bromide | 3.10-3.50 | 3.394 | 0.11 |

TABLE IX

Hydrogen bonding functional groups with alcohols and associated interaction distances

| Functional Group | Interaction Distances (angstroms) | Mean | Standard Deviation |
|---|---|---|---|
| Catemer | 2.40-3.00 | 2.783 | 0.08 |
| Primary Amide (C=O) | 2.50-3.00 | 2.753 | 0.07 |
| Primary Amide (NH$_2$) | 2.70-3.10 | 2.965 | 0.06 |
| Secondary Amide (C=O) | 2.50-3.04 | 2.773 | 0.09 |
| Secondary Amide (NH$_2$) | 2.50-3.20 | 2.933 | 0.11 |
| Carboxylic Acid (C=O) | 2.50-3.00 | 2.792 | 0.08 |
| Carboxylic Acid (OH) | 2.40-2.90 | 2.649 | 0.05 |
| Amino-pyridine (Aromatic N) | 2.60-3.06 | 2.790 | 0.07 |
| Amino-pyridine (NH$_2$) | 2.75-3.15 | 2.960 | 0.08 |
| Sulfonamide | 2.80-3.07 | 2.940 | 0.06 |
| Aromatic N | 2.50-3.00 | 2.777 | 0.08 |
| Water | 2.40-3.03 | 2.787 | 0.10 |
| Primary Amine | 2.60-3.15 | 2.897 | 0.13 |
| Secondary Amine | 2.60-3.15 | 2.888 | 0.13 |
| Carbonyl | 2.40-3.05 | 2.805 | 0.11 |
| Sulfonyl | 2.40-3.15 | 2.870 | 0.10 |
| Ether | 2.40-3.00 | 2.841 | 0.08 |
| Ester | 2.50-3.10 | 2.852 | 0.10 |
| Cyano | 2.40-3.10 | 2.873 | 0.09 |
| Nitro | 2.45-3.05 | 2.935 | 0.08 |
| Chloride | 2.60-3.30 | 3.093 | 0.07 |
| Bromide | 3.00-3.50 | 3.258 | 0.07 |

TABLE X

Hydrogen bonding functional groups with carboxylic acids and associated interaction distances

| Functional Group | Interaction Distances (angstroms) | Mean | Standard Deviation |
|---|---|---|---|
| Catemer | 2.50-3.00 | 2.690 | 0.08 |
| Dimer | 2.50-3.00 | 2.650 | 0.03 |
| Primary Amide (NH$_2$) | 2.80-3.25 | 2.961 | 0.09 |
| Primary Amide (C=O) | 2.40-2.80 | 2.560 | 0.07 |
| Secondary Amide (NH) | 2.70-3.10 | 2.920 | 0.09 |
| Secondary Amide (C=O) | 2.40-3.05 | 2.606 | 0.05 |
| Amino-pyridine (Aromatic N) | 2.50-2.80 | 2.670 | 0.05 |
| Amino-pyridine (NH$_2$) | 2.70-3.00 | 2.890 | 0.08 |
| Aromatic N | 2.54-2.94 | 2.658 | 0.06 |
| Water (to C=O) | 2.50-3.00 | 2.830 | 0.07 |
| Water (to OH) | 2.40-3.00 | 2.626 | 0.11 |
| Alcohol (to C=O) | 2.50-3.00 | 2.792 | 0.08 |
| Alcohol (to OH) | 2.50-2.90 | 2.649 | 0.05 |
| Primary Amine (to C=O) | 2.70-3.10 | 2.959 | 0.09 |
| Primary Amine (to OH) | 2.70-3.10 | 2.828 | 0.12 |
| Secondary Amine (to C=O) | 2.70-3.10 | 2.909 | 0.11 |
| Secondary Amine (to OH) | 2.70-3.10 | 2.727 | 0.12 |
| Carbonyl | 2.40-3.00 | 2.696 | 0.08 |
| Ether | 2.50-3.00 | 2.751 | 0.12 |
| Ester (C=O) | 2.40-3.05 | 2.672 | 0.07 |
| Ester (C—O—C) | 2.40-3.10 | 2.990 | N/A |
| Cyano | 2.50-2.80 | 2.746 | 0.09 |
| Nitro | 2.70-3.05 | 2.942 | 0.10 |
| Chloride | 2.80-3.20 | 3.001 | 0.05 |
| Bromide | 3.00-3.30 | 3.150 | 0.05 |

TABLE XI

Hydrogen bonding functional groups with carbonyls and associated interaction distances

| Functional Group | Interaction Distances (angstroms) | Mean | Standard Deviation |
|---|---|---|---|
| Primary Amide | 2.83-3.15 | 3.96 | 0.06 |
| Secondary Amide | 2.70-3.07 | 2.93 | 0.08 |
| Carboxylic Acid | 2.40-3.00 | 2.70 | 0.08 |

TABLE XI-continued

Hydrogen bonding functional groups with carbonyls and associated interaction distances

| Functional Group | Interaction Distances (angstroms) | Mean | Standard Deviation |
|---|---|---|---|
| Amino-pyridine | 2.87-3.10 | 2.95 | 0.07 |
| Secondary Sulfonamide | 2.76-3.22 | 2.949 | 0.12 |
| Water | 2.55-3.05 | 2.82 | 0.10 |
| Alcohol | 2.40-3.05 | 2.80 | 0.01 |
| Primary Amine | 2.64-3.15 | 2.959 | 0.09 |
| Secondary Amine | 2.64-3.15 | 2.87 | 0.01 |

TABLE XII

Hydrogen bonding functional groups with cyano groups and associated interaction distances

| Functional Group | Interaction Distances (angstroms) | Mean | Standard Deviation |
|---|---|---|---|
| Primary Amide | 3.01-3.30 | 3.15 | 0.09 |
| Secondary Amide | 2.90-3.30 | 3.13 | N/A |
| Carboxylic Acid | 2.57-3.00 | 2.75 | 0.09 |
| Amino-pyridine | 2.84-3.33 | 3.10 | 0.12 |
| Primary Sulfonamide | 2.99 | N/A | N/A |
| Secondary Sulfonamide | 2.83-3.00 | 2.90 | 0.07 |
| Water | 2.78-3.20 | 2.98 | 0.01 |
| Alcohol | 2.72-3.13 | 2.89 | 0.09 |
| Primary Amine | 2.84-3.27 | 3.08 | 0.09 |
| Secondary Amine | 2.84-3.30 | 3.09 | 0.12 |

TABLE XIII

Hydrogen bonding functional groups with sulfonyl groups and associated interaction distances

| Functional Group | Interaction Distances (angstroms) | Mean | Standard Deviation |
|---|---|---|---|
| Primary Amide | 2.92 | N/A | N/A |
| Secondary Amide | 2.95-3.25 | 3.08 | 0.09 |
| Primary Sulfonamide | 2.85-3.10 | 3.00 | 0.10 |
| Secondary Sulfonamide | 2.85-3.20 | 3.04 | N/A |
| Water | 2.84-3.00 | 2.90 | 0.05 |
| Alcohol | 2.65-3.15 | 2.87 | 0.1 |
| Primary Amine | 2.93-3.32 | 3.13 | 0.12 |
| Secondary Amine | 2.75-3.32 | 3.05 | 0.12 |

TABLE XIV

Hydrogen bonding functional groups with aromatic N and associated interaction distances

| Functional Group | Interaction Distances (angstroms) | Mean | Standard Deviation |
|---|---|---|---|
| Primary Amide | 2.90-3.21 | 3.07 | 0.07 |
| Secondary Amide | 2.60-3.15 | 2.96 | 0.09 |
| Carboxylic Acid | 2.54-2.94 | 2.66 | 0.06 |
| Amino-pyridine | 2.70-3.20 | 3.04 | 0.07 |
| Water | 2.60-3.15 | 2.91 | 0.09 |
| Alcohol | 2.50-3.00 | 2.78 | 0.08 |
| Primary Amine | 2.92-3.26 | 3.07 | 0.07 |
| Secondary Amine | 2.73-3.25 | 3.02 | 0.10 |

TABLE XV

Hydrogen bonding functional groups with ethers and associated interaction distances

| Functional Group | Interaction Distances (angstroms) | Mean | Standard Deviation |
|---|---|---|---|
| Primary Amide | 2.80-3.10 | 2.97 | 0.08 |
| Secondary Amide | 2.70-3.16 | 2.99 | 0.09 |
| Carboxylic Acid | 2.50-3.02 | 2.75 | 0.12 |
| Amino-pyridine | 2.80-3.20 | 3.05 | 0.07 |
| Sulfonamide | 0-3.20 | 3.07 | 0.08 |
| Water | 2.40-3.15 | 2.94 | 0.12 |
| Alcohol | 2.40-3.00 | 2.84 | 0.08 |
| Primary Amine | 2.75-3.25 | 3.05 | 0.11 |
| Secondary Amine | 2.60-3.25 | 3.05 | 0.13 |

TABLE XVI

Hydrogen bonding functional groups with chlorides and associated interaction distances

| Functional Group | Interaction Distances (angstroms) | Mean | Standard Deviation |
|---|---|---|---|
| Primary Amide | 3.10-3.60 | 3.34 | 0.08 |
| Secondary Amide | 2.90-3.30 | 3.18 | 0.06 |
| Carboxylic Acid | 2.80-3.30 | 3.00 | 0.05 |
| Amino-pyridine | 3.10-3.45 | 3.25 | 0.08 |
| Sulfonamide | 0-3.35 | 3.26 | 0.03 |
| Water | 2.70-3.30 | 3.17 | 0.06 |
| Alcohol | 2.50-3.30 | 3.09 | 0.07 |
| Primary Amine | 3.00-3.50 | 3.28 | 0.09 |
| Secondary Amine | 2.90-3.40 | 3.20 | 0.10 |

TABLE XVII

Hydrogen bonding functional groups with organochlorides and associated interaction distances

| Functional Group | Interaction Distances (angstroms) | Mean | Standard Deviation |
|---|---|---|---|
| Primary Amide | 3.18-3.21 | 3.20 | 0.02 |
| Secondary Amide | 3.20-3.27 | 3.25 | 0.03 |
| Carboxylic Acid | 2.90-3.23 | 3.17 | 0.07 |
| Amino-pyridine | 3.28-3.33 | 3.31 | 0.03 |
| Sulfonamide | 0-3.50 | N/A | N/A |
| Water | 2.79-3.26 | 3.14 | 0.15 |
| Alcohol | 2.90-3.29 | 3.17 | 0.09 |
| Primary Amine | 3.21-3.29 | 3.25 | 0.05 |
| Secondary Amine | 3.26-3.30 | 3.28 | 0.02 |

TABLE XVIII

Hydrogen bonding functional groups with bromides and associated interaction distances

| Functional Group | Interaction Distances (angstroms) | Mean | Standard Deviation |
|---|---|---|---|
| Primary Amide | 3.30-3.80 | 3.55 | 0.11 |
| Secondary Amide | 3.10-3.80 | 3.39 | 0.11 |
| Carboxylic Acid | 3.00-3.30 | 3.15 | 0.05 |
| Amino-pyridine | 3.20-3.50 | 3.39 | 0.05 |
| Alcohol | 3.00-3.50 | 3.26 | 0.07 |
| Primary Amine | 3.20-3.60 | 3.43 | 0.08 |
| Secondary Amine | 3.10-3.60 | 3.38 | 0.10 |

TABLE XIX

Hydrogen bonding functional groups with organobromides and associated interaction distances

| Functional Group | Interaction Distances (angstroms) | Mean | Standard Deviation |
|---|---|---|---|
| Primary Amide | 0-3.50 | 3.24 | N/A |
| Secondary Amide | 0-3.50 | N/A | N/A |
| Carboxylic Acid | 3.01-3.31 | 3.20 | 0.16 |
| Amino-pyridine | 0-3.50 | 3.38 | N/A |
| Sulfonamide | 0-3.50 | N/A | N/A |
| Water | 3.14-3.27 | 3.21 | 0.09 |
| Alcohol | 2.90-3.36 | 3.21 | 0.12 |
| Primary Amine | 0-3.50 | 3.38 | N/A |
| Secondary Amine | 3.20-3.39 | 3.30 | 0.12 |

TABLE XX

Hydrogen bonding functional groups with organoiodides and associated interaction distances

| Functional Group | Interaction Distances (angstroms) | Mean | Standard Deviation |
|---|---|---|---|
| Primary Amide | 0-3.80 | N/A | N/A |
| Secondary Amide | 0-3.80 | N/A | N/A |
| Carboxylic Acid | 0-3.80 | 3.59 | 0.16 |
| Amino-pyridine | 0-3.80 | 3.42 | N/A |
| Aromatic N | 2.70-3.23 | 2.95 | 0.11 |
| Alcohol | 2.90-3.48 | 3.20 | 0.20 |
| Primary Amine | 3.25-3.42 | 3.34 | 0.11 |
| Secondary Amine | 2.71-2.87 | 2.79 | 0.08 |

In another embodiment, peptides, proteins, nucleic acids or other biological APIs are excluded from the present invention. In another embodiment, all non-pharmaceutically acceptable co-crystal formers are excluded from the present invention. In another embodiment, organometalic APIs are excluded from the present invention. In another embodiment, a co-crystal former comprising any one or more of the functional groups of Table III may be specifically excluded from the present invention. In another embodiment, any one or more of the co-crystal formers of Table I or II may be specifically excluded from the present invention. Any APIs currently known in the art may also be specifically excluded from the present invention. For example, carbamazepine, itraconazole, nabumetone, fluoxetine, acetaminophen and theophylline can each be specifically excluded from the present invention. In another embodiment, the API is not a salt, is not a non-metal salt, or is not a metal salt, e.g., sodium, potassium, lithium, calcium or magnesium. In another embodiment, the API is a salt, is a non-metal salt, or is a metal salt, e.g., sodium, potassium, lithium, calcium, magnesium. In one embodiment, the API does not contain a halogen. In one embodiment, the API does contain a halogen.

In another embodiment, any one or more APIs may be specifically excluded from the present invention.

In another embodiment, a pharmaceutical composition can be formulated to contain an API in co-crystal form as micronized or nano-sized particles. More specifically, another embodiment couples the processing of a pure API to a co-crystal form with the process of making a controlled particle size for manipulation into a pharmaceutical dosage form. This embodiment combines two processing steps into a single step via techniques such as, but not limited to, grinding, alloying, or sintering (i.e., heating a powder mix). The coupling of these processes overcomes a serious limitation of having to isolate and store the bulk drug that is required for a formulation, which in some cases can be difficult to isolate (e.g., amorphous, chemically or physically unstable).

Excipients employed in pharmaceutical compositions of the present invention can be solids, semi-solids, liquids or combinations thereof. Preferably, excipients are solids. Compositions of the invention containing excipients can be prepared by any known technique of pharmacy that comprises admixing an excipient with an API or therapeutic agent. A pharmaceutical composition of the invention contains a desired amount of API per dose unit and, if intended for oral administration, can be in the form, for example, of a tablet, a caplet, a pill, a hard or soft capsule, a lozenge, a cachet, a dispensable powder, granules, a suspension, an elixir, a dispersion, or any other form reasonably adapted for such administration. If intended for parenteral administration, it can be in the form, for example, of a suspension or transdermal patch. If intended for rectal administration, it can be in the form, for example, of a suppository. Presently preferred are oral dosage forms that are discrete dose units each containing a predetermined amount of the API, such as tablets or capsules.

In another embodiment, APIs with an inappropriate pH for transdermal patches can be co-crystallized with an appropriate co-crystal former, thereby adjusting its pH to an appropriate level for use as a transdermal patch. In another embodiment, an APIs pH level can be optimized for use in a transdermal patch via co-crystallization with an appropriate co-crystal former.

Non-limiting examples follow of excipients that can be used to prepare pharmaceutical compositions of the invention.

Pharmaceutical compositions of the invention optionally comprise one or more pharmaceutically acceptable carriers or diluents as excipients. Suitable carriers or diluents illustratively include, but are not limited to, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose (e.g., RexcelJ), powdered cellulose, hydroxypropylcellulose (HPC) and hydroxypropylmethylcellulose (HPMC); calcium carbonate; glycine; bentonite; block co-polymers; polyvinylpyrrolidone; and the like. Such carriers or diluents, if present, constitute in total about 5% to about 99%, preferably about 10% to about 85%, and more preferably about 20% to about 80%, of the total weight of the composition. The carrier, carriers, diluent, or diluents selected preferably exhibit suitable flow properties and, where tablets are desired, compressibility.

Lactose, mannitol, dibasic sodium phosphate, and microcrystalline cellulose (particularly Avicel PH microcrystalline cellulose such as Avicel PH 101), either individually or in combination, are preferred diluents. These diluents are chemically compatible with many co-crystals described herein. The use of extragranular microcrystalline cellulose (that is, microcrystalline cellulose added to a granulated composition) can be used to improve hardness (for tablets) and/or disintegration time. Lactose, especially lactose monohydrate, is particularly preferred. Lactose typically provides compositions having suitable release rates of co-crystals, stability, pre-compression flowability, and/or drying properties at a relatively low diluent cost. It provides a high density substrate that aids densification during granulation (where wet granulation is employed) and therefore improves blend flow properties and tablet properties.

Pharmaceutical compositions of the invention optionally comprise one or more pharmaceutically acceptable disintegrants as excipients, particularly for tablet formulations. Suitable disintegrants include, but are not limited to, either individually or in combination, starches, including sodium starch glycolate (e.g., Explotab™ of PenWest) and pregelatinized corn starches (e.g., National™ 1551 of National Starch and Chemical Company, National™ 1550, and Colorcon™ 1500), clays (e.g., Veegum™ HV of R.T. Vanderbilt), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition.

Croscarmellose sodium is a preferred disintegrant for tablet or capsule disintegration, and, if present, preferably constitutes about 0.2% to about 10%, more preferably about 0.2% to about 7%, and still more preferably about 0.2% to about 5%, of the total weight of the composition. Croscarmellose sodium confers superior intragranular disintegration capabilities to granulated pharmaceutical compositions of the present invention.

Pharmaceutical compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Such binding agents may also prevent or inhibit crystallization or recrystallization of a co-crystal of the present invention once the salt has been dissolved in a solution. Suitable binding agents and adhesives include, but are not limited to, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™ of Aqualon); and ethylcellulose (e.g., Ethocel™ of the Dow Chemical Company). Such binding agents and/or adhesives, if present, constitute in total about 0.5% to about 25%, preferably about 0.75% to about 15%, and more preferably about 1% to about 10%, of the total weight of the pharmaceutical composition.

Many of the binding agents are polymers comprising amide, ester, ether, alcohol or ketone groups and, as such, are preferably included in pharmaceutical compositions of the present invention. Polyvinylpyrrolidones such as povidone K-30 are especially preferred. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these units' ratios in a given polymer affects properties and performance. Examples of block co-polymers with varying compositions of block units are Poloxamer 188 and Poloxamer 237 (BASF Corporation).

Pharmaceutical compositions of the invention optionally comprise one or more pharmaceutically acceptable wetting agents as excipients. Such wetting agents are preferably selected to maintain the co-crystal in close association with water, a condition that is believed to improve bioavailability of the composition. Such wetting agents can also be useful in solubilizing or increasing the solubility of co-crystals.

Non-limiting examples of surfactants that can be used as wetting agents in pharmaceutical compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and degrees Ctoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the pharmaceutical composition.

Wetting agents that are anionic surfactants are preferred. Sodium lauryl sulfate is a particularly preferred wetting agent. Sodium lauryl sulfate, if present, constitutes about 0.25% to about 7%, more preferably about 0.4% to about 4%, and still more preferably about 0.5% to about 2%, of the total weight of the pharmaceutical composition.

Pharmaceutical compositions of the invention optionally comprise one or more pharmaceutically acceptable lubricants (including anti-adherents and/or glidants) as excipients. Suitable lubricants include, but are not limited to, either individually or in combination, glyceryl behapate (e.g., Compritol™ 888 of Gattefosse); stearic acid and salts thereof, including magnesium, calcium and sodium stearates; hydrogenated vegetable oils (e.g., Sterotex™ of Abitec); colloidal silica; talc; waxes; boric acid; sodium benzoate; sodium acetate; sodium fumarate; sodium chloride; DL-leucine; PEG (e.g., Carbowax™ 4000 and Carbowax™ 6000 of the Dow Chemical Company); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the pharmaceutical composition.

Magnesium stearate is a preferred lubricant used, for example, to reduce friction between the equipment and granulated mixture during compression of tablet formulations.

Suitable anti-adherents include, but are not limited to, talc, cornstarch, DL-leucine, sodium lauryl sulfate and metallic stearates. Talc is a preferred anti-adherent or glidant used, for example, to reduce formulation sticking to equipment surfaces and also to reduce static in the blend. Talc, if present, constitutes about 0.1% to about 10%, more preferably about 0.25% to about 5%, and still more preferably about 0.5% to about 2%, of the total weight of the pharmaceutical composition.

Glidants can be used to promote powder flow of a solid formulation. Suitable glidants include, but are not limited to, colloidal silicon dioxide, starch, talc, tribasic calcium phosphate, powdered cellulose and magnesium trisilicate. Colloidal silicon dioxide is particularly preferred.

Other excipients such as colorants, flavors and sweeteners are known in the pharmaceutical art and can be used in pharmaceutical compositions of the present invention. Tablets can be coated, for example with an enteric coating, or uncoated. Compositions of the invention can further comprise, for example, buffering agents. Optionally, one or more effervescent agents can be used as disintegrants and/or to enhance organoleptic properties of pharmaceutical compositions of the invention. When present in pharmaceutical compositions of the invention to promote dosage form disintegration, one or more effervescent agents are preferably present in a total amount of about 30% to about 75%, and preferably about 45% to about 70%, for example about 60%, by weight of the pharmaceutical composition.

According to a particularly preferred embodiment of the invention, an effervescent agent, present in a solid dosage form in an amount less than that effective to promote disintegration of the dosage form, provides improved dispersion of the API in an aqueous medium. Without being bound by theory, it is believed that the effervescent agent is effective to accelerate dispersion of the API from the dosage form in the gastrointestinal tract, thereby further enhancing absorption and rapid onset of therapeutic effect. When present in a pharmaceutical composition of the invention to promote intragastrointestinal dispersion but not to enhance disintegration, an effervescent agent is preferably present in an amount of about 1% to about 20%, more preferably about 2.5% to about 15%, and still more preferably about 5% to about 10%, by weight of the pharmaceutical composition.

An "effervescent agent" herein is an agent comprising one or more compounds which, acting together or individually, evolve a gas on contact with water. The gas evolved is generally oxygen or, most commonly, carbon dioxide. Preferred effervescent agents comprise an acid and a base that react in the presence of water to generate carbon dioxide gas. Preferably, the base comprises an alkali metal or alkaline earth metal carbonate or bicarbonate and the acid comprises an aliphatic carboxylic acid.

Non-limiting examples of suitable bases as components of effervescent agents useful in the invention include carbonate salts (e.g., calcium carbonate), bicarbonate salts (e.g., sodium bicarbonate), sesquicarbonate salts, and mixtures thereof. Calcium carbonate is a preferred base.

Non-limiting examples of suitable acids as components of effervescent agents and/or solid organic acids useful in the invention include citric acid, tartaric acid (as D-, L-, or D/L-tartaric acid), malic acid (as D-, L-, or DL-malic acid), maleic acid, fumaric acid, adipic acid, succinic acid, acid anhydrides of such acids, acid salts of such acids, and mixtures thereof. Citric acid is a preferred acid.

In a preferred embodiment of the invention, where the effervescent agent comprises an acid and a base, the weight ratio of the acid to the base is about 1:100 to about 100:1, more preferably about 1:50 to about 50:1, and still more preferably about 1:10 to about 10:1. In a further preferred embodiment of the invention, where the effervescent agent comprises an acid and a base, the ratio of the acid to the base is approximately stoichiometric.

Excipients which solubilize APIs typically have both hydrophilic and hydrophobic regions, or are preferably amphiphilic or have amphiphilic regions. One type of amphiphilic or partially-amphiphilic excipient comprises an amphiphilic polymer or is an amphiphilic polymer. A specific amphiphilic polymer is a polyalkylene glycol, which is commonly comprised of ethylene glycol and/or propylene glycol subunits. Such polyalkylene glycols can be esterified at their termini by a carboxylic acid, ester, acid anhydride or other suitable moiety. Examples of such excipients include poloxamers (symmetric block copolymers of ethylene glycol and propylene glycol; e.g., poloxamer 237), polyalkylene glycolated esters of tocopherol (including esters formed from a di- or multi-functional carboxylic acid; e.g., d-alpha-tocopherol polyethylene glycol-1000 succinate), and macrogolglycerides (formed by alcoholysis of an oil and esterification of a polyalkylene glycol to produce a mixture of mono-, di- and tri-glycerides and mono- and di-esters; e.g., stearoyl macrogol-32 glycerides). Such pharmaceutical compositions are advantageously administered orally.

Pharmaceutical compositions of the present invention can comprise about 10% to about 50%, about 25% to about 50%, about 30% to about 45%, or about 30% to about 35% by weight of a co-crystal; about 10% to about 50%, about 25% to about 50%, about 30% to about 45%, or about 30% to about 35% by weight of an excipient which inhibits crystallization in aqueous solution, in simulated gastric fluid, or in simulated intestinal fluid; and about 5% to about 50%, about 10% to about 40%, about 15% to about 35%, or about 30% to about 35% by weight of a binding agent. In one example, the weight ratio of the co-crystal to the excipient which inhibits crystallization to binding agent is about 1 to 1 to 1.

Solid dosage forms of the invention can be prepared by any suitable process, not limited to processes described herein.

An illustrative process comprises (a) a step of blending an API of the invention with one or more excipients to form a blend, and (b) a step of tableting or encapsulating the blend to form tablets or capsules, respectively.

In a preferred process, solid dosage forms are prepared by a process comprising (a) a step of blending a co-crystal of the invention with one or more excipients to form a blend, (b) a step of granulating the blend to form a granulate, and (c) a step of tableting or encapsulating the blend to form tablets or capsules respectively. Step (b) can be accomplished by any dry or wet granulation technique known in the art, but is preferably a dry granulation step. A salt of the present invention is advantageously granulated to form particles of about 1 micrometer to about 100 micrometer, about 5 micrometer to about 50 micrometer, or about 10 micrometer to about 25 micrometer. One or more diluents, one or more disintegrants and one or more binding agents are preferably added, for example in the blending step, a wetting agent can optionally be added, for example in the granulating step, and one or more disintegrants are preferably added after granulating but before tableting or encapsulating. A lubricant is preferably added before tableting. Blending and granulating can be performed independently under low or high shear. A process is preferably selected that forms a granulate that is uniform in API content, that readily disintegrates, that flows with sufficient ease so that weight variation can be reliably controlled during capsule filling or tableting, and that is dense enough in bulk so that a batch can be processed in the selected equipment and individual doses fit into the specified capsules or tablet dies.

In an alternative embodiment, solid dosage forms are prepared by a process that includes a spray drying step, wherein an API is suspended with one or more excipients in one or more sprayable liquids, preferably a non-protic (e.g., non-aqueous or non-alcoholic) sprayable liquid, and then is rapidly spray dried over a current of warm air.

A granulate or spray dried powder resulting from any of the above illustrative processes can be compressed or molded to prepare tablets or encapsulated to prepare capsules. Conventional tableting and encapsulation techniques known in the art can be employed. Where coated tablets are desired, conventional coating techniques are suitable. Excipients for tablet compositions of the invention are preferably selected to provide a disintegration time of less than about 30 minutes, preferably about 25 minutes or less, more preferably about 20 minutes or less, and still more preferably about 15 minutes or less, in a standard disintegration assay.

Pharmaceutically acceptable co-crystals can be administered by controlled-, sustained-, or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the co-crystals and compositions of the invention. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed co-crystals and thus effect controlled delivery of the drug. Examples of specific anion exchangers include, but are not limited to, Duolite® A568 and Duolite® AP143 (Rohm & Haas, Spring House, Pa. USA).

One embodiment of the invention encompasses a unit dosage form which comprises a pharmaceutically acceptable co-crystal, or a solvate, hydrate, dehydrate, anhydrous, or amorphous form thereof, and one or more pharmaceutically acceptable excipients or diluents, wherein the pharmaceutical composition or dosage form is formulated for controlled-release. Specific dosage forms utilize an osmotic drug delivery system.

A particular and well-known osmotic drug delivery system is referred to as OROS® (Alza Corporation, Mountain View, Calif. USA). This technology can readily be adapted for the delivery of compounds and compositions of the invention. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS® that can be used to administer compounds and compositions of the invention include, but are not limited to, the OROS® Push-Pull™, Delayed Push-Pull™, Multi-Layer Push-Pull™, and Push-Stick™ Systems, all of which are well known. See, e.g., http://www.alza.com. Additional OROS® systems that can be used for the controlled oral delivery of compounds and compositions of the invention include OROS®-CT and L-OROS®. Id.; see also, Delivery Times, vol. II, issue II (Alza Corporation).

Conventional OROS® oral dosage forms are made by compressing a drug powder (e.g. co-crystal) into a hard tablet, coating the tablet with cellulose derivatives to form a semipermeable membrane, and then drilling an orifice in the coating (e.g., with a laser). Kim, Cherng-ju, Controlled Release Dosage Form Design, 231-238 (Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS® drug delivery systems cannot be used to effectively deliver drugs with low water solubility. Id. at 234. Because co-crystals of this invention can be far more soluble in water than the API itself, they are well suited for osmotic-based delivery to patients.

This invention does, however, encompass the incorporation of conventional crystalline API (e.g. pure API without co-crystal former), and non-salt isomers and isomeric mixtures thereof, into OROS® dosage forms.

A specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent to the exit orifice and in direct or indirect contacting relationship with the expandable layer; and a flow-promoting layer interposed between the inner surface of the wall and at least the external surface of the drug layer located within the cavity, wherein the drug layer comprises a co-crystal, or a solvate, hydrate, dehydrate, anhydrous, or amorphous form thereof. See U.S. Pat. No. 6,368,626, the entirety of which is incorporated herein by reference.

Another specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a co-crystal, or a solvate, hydrate, dehydrate, anhydrous, or amorphous form thereof. See U.S. Pat. No. 6,342,249, the entirety of which is incorporated herein by reference.

An example of a delayed-release dosage form that also functions as a time controlled-release dosage form is described in U.S. Pat. No. 5,366,738, herein incorporated by reference in its entirety. The controlled-release drug delivery device described in U.S. Pat. No. 5,366,738 is known as a gel extrusion module (GEM) delivery device. The GEM device is a drug delivery device for the controlled in situ production and release of a dispersion containing an API comprising:

(A) a compressed core prepared from an admixture comprising:
  (i) a therapeutically effective amount of the API; and
  (ii) a polymer which upon hydration forms gelatinous microscopic particles; and
(B) a water insoluble, water impermeable polymeric coating comprising a polymer and a plasticizer, which surrounds and adheres to the core, the coating having a plurality of formed apertures exposing between about 1 and about 75% of the core surface; and wherein the release rate of the beneficial agent from the device is a function of the number and size of the apertures.

In the GEM device, the polymer inside the compressed core is selected from materials such as sodium polyacrylate, carboxypolymethylenes and the pharmaceutically acceptable salts thereof such as a sodium salt, wherein the carboxypolymethylenes are prepared from acrylic acid crosslinked with allylethers of sucrose or pentaerythritol, and, for example, it is selected from carboxypolymethylenes prepared from acrylic acid crosslinked with allylethers of sucrose or pentaerythritol, and the pharmaceutically acceptable salts thereof. Often CARBOPOL® 974P and pharmaceutically acceptable salts thereof, particularly the sodium salt, is used as the polymer inside the compressed core. In addition, the compressed core may also contain one or more polymer hydration modulating agents, anti-oxidants, lubricants, fillers and excipients. An optional subcoating may be applied to the compressed core prior to application of the water insoluble coating as an aid in the manufacturing process. The subcoating may be comprised of, for example, hydroxypropyl cellulose and hydroxypropylmethylcellulose. Additional coatings may be applied for aesthetic or functional purposes.

The water insoluble, water impermeable polymeric coating is comprised of, for example, (1) a polymer selected from polyvinyl chloride, cellulose acetate, cellulose acetate butyrate, ethylcellulose and combinations of these polymers; and (2) a plasticizer selected from diethylphthalate, dibutylsebacate and triethylcitrate. For example, the polymeric coating is comprised of cellulose acetate butyrate and triethyl citrate. The GEM device does not function as an osmotic drug delivery device, hence the release function of the device depends on passage of fluids from the external environment of the body to the internal environment of the compressed core through the formed apertures. It is intended that the terms "water insoluble, water impermeable" used to describe the polymeric coating define a coating which is essentially water insoluble and water impermeable, meaning that the polymeric coating allows minimal to no passage of water through the coating from the external environment of the body to the internal environment of the compressed core, except for the fluid passage that occurs through the drilled apertures, during the period of time the API is being released from the GEM device in the body. Any minimal amount of water that does pass through the water insoluble, water impermeable polymeric coating is insubstantial and does not significantly contribute to the function of the GEM device, i.e. the release rate of the drug through the apertures. Rather the release rate of API from the GEM device is primarily a function of the number and size of the apertures on the device.

For an elegant, aesthetically pleasing final product, an outer finish coat may finally be applied to the GEM delivery device containing colorants, waxes, and the like. The GEM device can also be enterically coated, either before or after the application of additional finish coatings. Even without enteric coating, extrusion of the polymer which carries API out from inside the compressed core of the GEM device does not occur to a substantial extent in the acidic pH of the stomach, therefore substantial release of API should not occur in the stomach. Further details and examples of the GEM delivery device are described in U.S. Pat. No. 5,366,738.

According to the present invention, the packaging of pharmaceutical compositions can be accomplished via a container for containing the pharmaceutical compositions and may also include divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

An example of such a container is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

The invention will now be described in further detail, by way of example, with reference to the accompanying drawings.

EXEMPLIFICATION

General Methods for the Preparation of Co-Crystals a) High Throughput Crystallization Using the CrystalMax™ Platform CrystalMax™ comprises a sequence of automated, integrated high throughput robotic stations capable of rapid generation, identification and characterization of polymorphs, salts, and co-crystals of APIs and API candidates. Worksheet generation and combinatorial mixture design is carried out using proprietary design software Architect™. Typically, an API or an API candidate is dispensed from an organic solvent into tubes and dried under a stream of nitrogen. Salts and/or co-crystal formers may also be dispensed and dried in the same fashion. Water and organic solvents may be combinatorially dispensed into the tubes using a multi-channel dispenser. Each tube in a 96-tube array is then sealed within 15 seconds of combinatorial dispensing to avoid solvent evaporation. The mixtures are then rendered supersaturated by heating to 70 degrees C. for 2 hours followed by a 1 degree C./minute cooling ramp to 5 degrees C. Optical checks are then conducted to detect crystals and/or solid material. Once a solid has been identified in a tube, it is isolated through aspiration and drying. Raman spectra are then obtained on the solids and cluster classification of the spectral patterns is performed using proprietary software (Inquire™).

b) Crystallization from Solution

Co-crystals may be obtained by dissolving the separate components in a solvent and adding one to the other. The co-crystal may then precipitate or crystallize as the solvent mixture is evaporated slowly. The co-crystal may also be obtained by dissolving the two components in the same solvent or a mixture of solvents.

c) Crystallization from the Melt (Co-melting)

A co-crystal may be obtained by melting the two components together (i.e., co-melting) and allowing recrystallization to occur. In some cases, an anti-solvent may be added to facilitate crystallization.

d) Thermal Microscopy

A co-crystal may be obtained by melting the higher melting component on a glass slide and allowing it to recrystallize. The second component is then melted and is also allowed to recrystallize. The co-crystal may form as a separated phase/band in between the eutectic bands of the two original components.

e) Mixing and/or Grinding

A co-crystal may be obtained by mixing or grinding two components together in the solid state. Grinding can be controlled so as to result in a gentle, intermediate, or an intense blending of API and co-crystal former. Heating of such blended material can also be used to cause co-crystal formation. Co-crystals can also be prepared via grinding an API and a co-crystal former with a small amount of an appropriate solvent.

In another embodiment, a co-crystal is prepared with the addition of solvent, without the addition of solvent, or both. Solvents used in such a co-crystallization process can be, for example, but not limited to, acetone, methanol, ethanol, isopropyl alcohol, ethyl acetate, isopropyl acetate, nitromethane, dichloromethane, chloroform, toluene, propylene glycol, dimethyl sulfoxide (DMSO), dimethyl formamide (DMF), diethyl ether (ether), ethyl formate, hexane, acetonitrile, or another organic solvent including alcohols.

This technique can be used to prepare co-crystals with several APIs. For example, any of the APIs listed in Table IV of U.S. application Ser. No. 10/660,202, filed Sep. 11, 2003, can be prepared as co-crystals via grinding with a small amount of an appropriate solvent.

A "small amount" of solvent can be defined as up to about 40 percent by weight (w/w). For example, a weight percent of less than or equal to about 1, 2, 3, 4, 5, 10, 15, 20, 25, 30, 35, 40 or an intermediate amount can be considered a small amount of solvent. The weight percent of solvent can be determined by the weight of the solvent added with respect to the weight of the solvent, API, and co-crystal former combined.

A "small amount" of solvent can also be defined as an amount of solvent which solubilizes less than about 1, 2, 3, 4, or 5 percent by weight of the total API and co-crystal former.

In another embodiment, a solvent for use in the wet grinding of an API and a co-crystal former solubilizes less than or about 5 percent by weight of the solids. In another embodiment, a solvent for use in the wet grinding of an API and a co-crystal former solubilizes less than or about 4 percent by weight of the solids. In another embodiment, a solvent for use in the wet grinding of an API and a co-crystal former solubilizes less than or about 3 percent by weight of the solids. In another embodiment, a solvent for use in the wet grinding of an API and a co-crystal former solubilizes less than or about 2 percent by weight of the solids. In another embodiment, a solvent for use in the wet grinding of an API and a co-crystal former solubilizes less than or about 1 percent by weight of the solids.

In another embodiment, a co-crystal is prepared via milling or grinding an API, a co-crystal former, and a small amount of solvent.

In another embodiment, a process is provided for preparing a pharmaceutical co-crystal composition comprising an API and a co-crystal former, comprising:
 (a) providing an appropriate solvent and the API and the co-crystal former, wherein the co-crystal former is a solid at room temperature;
 (b) grinding the API, the co-crystal former, and a small amount of the appropriate solvent, so as to form a solid phase, wherein the API and co-crystal former are hydrogen bonded to each other; and (c) isolating co-crystals formed thereby.

In another embodiment, the above process further comprises incorporating the co-crystals into a pharmaceutical composition or a medicament.

f) Co-sublimation

A co-crystal may be obtained by co-subliming a mixture of an API and a co-crystal former in the same sample cell as an intimate mixture either by heating, mixing or placing the mixture under vacuum. A co-crystal may also be obtained by co-sublimation using a Kneudsen apparatus where the API and the co-crystal former are contained in separate sample cells, connected to a single cold finger, each of the sample cells is maintained at the same or different temperatures under a vacuum atmosphere in order to co-sublime the two components onto the cold-finger forming the desired co-crystal.

In another embodiment, co-crystals can be provided by seeding a solution containing an API and a co-crystal former with a co-crystal. The desired co-crystal can then be isolated by one of many techniques known to those skilled in the art.

Also, combinations and variations of the above techniques may be used to cause co-crystal formation.

Analytical Methods

Procedure for DSC Analysis

DSC analysis of the samples was performed using a Q1000 Differential Scanning Calorimeter (TA Instruments, New Castle, Del., U.S.A.), which uses Advantage for QW-Series, version 1.0.0.78, Thermal Advantage Release 2.0 (2001 TA Instruments-Water LLC). In addition, the analysis software used was Universal Analysis 2000 for Windows 95/95/2000/NT, version 3.1E; Build 3.1.0.40 (2001 TA Instruments-Water LLC).

For the DSC analysis, the purge gas used was dry nitrogen, the reference material was an empty aluminum pan that was crimped, and the sample purge was 50 mL/minute.

DSC analysis of the sample was performed by placing ≦2 mg of sample in an aluminum pan with a crimped pan closure. The starting temperature was typically 20 degrees C. with a heating rate of 10 degrees C./minute, and the ending temperature was 300 degrees C. Unless otherwise indicated, all reported transitions are as stated +/−1.0 degrees C.

Procedure for TGA Analysis

TGA analysis of samples was performed using a Q500 Thermogravimetric Analyzer (TA Instruments, New Castle, Del., U.S.A.), which uses Advantage for QW-Series, version 1.0.0.78, Thermal Advantage Release 2.0 (2001 TA Instruments-Water LLC). In addition, the analysis software used was Universal Analysis 2000 for Windows 95/95/2000/NT, version 3.1E; Build 3.1.0.40 (2001 TA Instruments-Water LLC).

For all of the TGA experiments, the purge gas used was dry nitrogen, the balance purge was 40 mL/minute $N_2$, and the sample purge was 60 mL/minute $N_2$.

TGA of the sample was performed by placing ≦2 mg of sample in a platinum pan. The starting temperature was typically 20 degrees C. with a heating rate of 10 degrees C./minute, and the ending temperature was 300 degrees C.

Procedure for PXRD Analysis

A powder X-ray diffraction (PXRD) pattern for the samples was obtained using a D/Max Rapid, Contact (Rigaku/MSC, The Woodlands, Tex., U.S.A.), which uses as its control software RINT Rapid Control Software, Rigaku Rapid/XRD, version 1.0.0 (1999 Rigaku Co.). In addition, the analysis software used were RINT Rapid display software, version 1.18 (Rigaku/MSC), and JADE XRD Pattern Processing, versions 5.0 and 6.0 ((1995-2002, Materials Data, Inc.).

For the PXRD analysis, the acquisition parameters were as follows: source was Cu with a K line at 1.5406 Å; x-y stage was manual; collimator size was 0.3 mm; capillary tube (Charles Supper Company, Natick, Mass., U.S.A.) was 0.3 mm ID; reflection mode was used; the power to the X-ray tube was 46 kV; the current to the X-ray tube was 40 mA; the omega-axis was oscillating in a range of 0-5 degrees at a speed of 1 degree/minute; the phi-axis was spinning at an angle of 360 degrees at a speed of 2 degrees/second; 0.3 mm collimator; the collection time was 60 minutes; the temperature was room temperature; and the heater was not used. The sample was presented to the X-ray source in a boron rich glass capillary.

In addition, the analysis parameters were as follows: the integration 2-theta range was 2-60 degrees; the integration chi range was 0-360 degrees; the number of chi segments was 1; the step size used was 0.02; the integration utility was cylint; normalization was used; dark counts were 8; omega offset was 180; and chi and phi offsets were 0.

PXRD diffractograms were also acquired via the Bruker AXS D8 Discover X-ray Diffractometer. This instrument was equipped with GADDS™ (General Area Diffraction Detection System), a Bruker AXS HI-STAR Area Detector at a distance of 15.05 cm as per system calibration, a copper source (Cu/$K_\alpha$ 1.54056 angstroms), automated x-y-z stage, and 0.5 mm collimator. The sample was compacted into pellet form and mounted on the x-y-z stage. A diffractogram was acquired under ambient conditions (25 degrees C.) at a powder setting of 40 kV and 40 mA in reflection mode while the sample remained stationary. The exposure time was varied and specified for each sample. The diffractogram obtained underwent a spatial remapping procedure to account for the geometrical pincushion distortion of the area detector then integrated along chi from −118.8 to −61.8 degrees and 2-theta 2.1-37 degrees at a step size of 0.02 degrees with normalization set to bin normalize.

The relative intensity of peak in a diffractogram is not necessarily a limitation of the PXRD pattern because peak intensity can vary from sample to sample, e.g., due to crystalline impurities. Further, the angles of each peak can vary by about +/−0.1 degrees, or +/−0.05. The entire pattern or most of the pattern peaks may also shift by about +/−0.1 degrees to about +/−0.2 degrees due to differences in calibration, settings, and other variations from instrument to instrument and from operator to operator. All reported PXRD peaks in the Figures, Examples, and elsewhere herein are reported with an error of about ±0.1 degrees 2-theta.

Unless otherwise specified, all infrared (IR) spectra were acquired using a Nicolet Avatar 320 FTIR.

Procedure for Single Crystal X-Ray Diffraction

Single crystal x-ray data were collected on a Bruker SMART-APEX CCD diffractometer (M. J. Zaworotko, Department of Chemistry, University of South Florida) with monochromatized Mo Kα radiation (λ=0.71073 angstroms) connected to KRYO-FLEX low temperature device. Lattice parameters were determined from least squares analysis. Reflection data was integrated using the program SAINT. Lorentz and polarization corrections were applied for diffracted reflections. In addition, the data were corrected for absorption using SADABS. The structure was solved by direct methods and refined by full matrix least squares using the program SHELXTL (Sheldrick, G. M. SHELXTL, Release 5.03; Siemans Analytical X-ray Instruments Inc.: Madison, Wis.). All non-hydrogen atoms were refined with anisotropic displacement parameters. All H-atoms bonded to carbon atoms, except methyl groups, were placed geometrically and refined with an isotropic displacement parameter fixed at 1.2 times $U_q$ for the atoms to which they were attached. H-atoms of methyl groups as well as N or O-bonded protons were located from Fourier difference map and refined with isotropic thermal parameters based upon the corresponding N or O-atom [U(H)=1.2$U_q$(N,O)].

The co-crystals of the present invention can be characterized, e.g., by the TGA or DSC data or by any one, any two, any three, any four, any five, any six, any seven, any eight, any nine, any ten, or any single integer number of PXRD 2-theta angle peaks or IR peaks listed herein or disclosed in a figure, or by single-crystal x-ray diffraction data.

Example 1

Carbamazepine:4-aminobenzoic acid Co-crystal 40 mg (0.1693 mmol) of carbamazepine and 30 mg (0.1421 mmol) of 4-aminobenzoic acid were dissolved in approximately 3 mL methanol. Slow evaporation of the solvent yielded clear plates of carbamazepine:4-aminobenzoic acid (2:1) co-crystal. The co-crystal was analyzed via IR spectroscopy and single-crystal x-ray diffraction.

Infrared Spectroscopy: (Nicolet Avatar 320 FTIR). 3460 cm$^{-1}$, (N—H stretch, 1° amine, carbamazepine); 3162 cm$^{-1}$, (C—H stretch, alkene); 1673 cm$^{-1}$, (C=O); 1603 cm$^{-1}$, (C=C).

A MEL-TEMP was used to determine the melting point of the carbamazepine:4-aminobenzoic acid co-crystal. The melting point was determined to be 185-187 degrees C.

Single crystal x-ray data (Bruker SMART-APEX CCD): $(C_{15}H_{12}N_2O)_2:C_7H_7NO_2$, M=609.67, monoclinic C2/c, a=31.013(3) angstroms, b=12.1319(9) angstroms, c=13.599 (1) angstroms, alpha=90 degrees, beta=99.173(1) degrees, gamma=90 degrees, V=6028.4(8) cubic angstroms, T=100 K, Z=8, $D_c$=1.343 g/cm$^3$, $\lambda$=0.71073 angstroms. Final residuals for 415 parameters were $R_1$ [I>2sigma(I)]=0.0416 and w$R_2$=0.106.

The carbamazepine:4-aminobenzoic acid co-crystal contains both an acid-amide 2-point supramolecular heterosynthon and a primary amide dimer. Two acid-amide supramolecular heterosynthons form a tetrameric motif, which is bonded to the primary amide dimers on each side through the amino N—H . . . O hydrogen bonds. This tetrameric motif is found in 13 percent of the structures in the CSD that contain acid-amide supramolecular heterosynthons. The O—H . . . O and N—H . . . O hydrogen bond interaction distances for the acid-amide supramolecular heterosynthon are 2.540 and 2.982 angstroms, which compare to the mean values of 2.56 and 2.96 angstroms, respectively.

Example 2

Carbamazepine:4-aminobenzoic acid:Water Co-crystal

Yellow crystals of carbamazepine:4-aminobenzoic acid: water (2:1:1) co-crystal were obtained via slow evaporation of a solution containing carbamazepine (0.030 g, 0.127 mmol) and 4-aminobenzoic acid (0.0087 g, 0.063 mmol) dissolved in 1 ml of heated ethanol after 2 days. The co-crystal was analyzed via TGA and single-crystal x-ray diffraction.

A MEL-TEMP was used to determine the melting point of the carbamazepine:4-aminobenzoic acid:water co-crystal. The melting point was determined to be about 143 degrees C.

TGA analysis of the carbamazepine:4-aminobenzoic acid: water co-crystal showed a 3 percent weight loss at 135 degrees C., a 68 percent weight loss at 174 degrees C., and a 12 percent weight loss at 306 degrees C.

Single crystal x-ray data (Bruker SMART-APEX CCD): $(C_{15}H_{12}N_2O)_2:C_7H_7NO_2:H_2O$, M=627.68, monoclinic $P2_1/n$, a=13.760(1) angstroms, b=17.457(1) angstroms, c=14.624(1) angstroms, alpha=90 degrees, beta=115.876(1) degrees, gamma=90 degrees, V=3160.8(4) cubic angstroms, T=100 K, Z=4, $D_c$=1.319 g/cm$^3$, $\lambda$=0.71073 angstroms. Final residuals for 424 parameters were $R_1$ [I>2sigma(I)]=0.0431 and w$R_2$=0.1112.

Co-crystallizing the same components as Example 1 but from ethanol produced a 2:1:1 co-crystal of carbamazepine: 4-aminobenzoic acid:water. The crystal packing is markedly different from the crystal structure of the carbamazepine:4-aminobenzoic acid co-crystal. It forms an eight molecule discrete unit through O—H . . . O and N—H . . . O hydrogen bonds that contain four carbamazepine molecules, two 4-aminobenzoic acid molecules, and two water molecules. The water molecules insert between the primary amide carbonyl and the acid OH, thereby sustaining 1-point N—H . . . O acid-amide supramolecular heterosynthons. The (amide) N—H . . . O (acid) interaction distance is 2.878 angstroms, versus a mean of 2.96 angstroms. Notably, the amide anti-oriented NH's are not involved in hydrogen bonding.

TABLE XXI

Geometrical parameters of H-bond interactions

| Co-crystal | Interaction | Distance (H . . . A) angstroms | Distance (D . . . A) angstroms | Theta (degrees) |
|---|---|---|---|---|
| Carbamazepine:4-aminobenzoic acid (Example 1) | O—H . . . O(amide) | 1.58 | 2.540(1) | 169.0 |
| | N—H(amine) . . . O(amide) | 2.12 | 3.014(2) | 162.3 |
| | N—H(amide) . . . O(acid) | 2.11 | 2.982(2) | 163.0 |
| | N—H(amide) . . . O(amide) | 2.00 | 2.907(2) | 169.5 |
| | N—H(amide) . . . O(acid) | 2.37 | 3.178(2) | 160.0 |
| Carbamazepine:4-aminobenzoic acid:water (Example 2) | O—H(water) . . . O(acid) | 1.69 | 2.593(1) | 170.0 |
| | O—H(water) . . . O(amide1) | 1.80 | 2.672(1) | 172.0 |
| | O—H(water) . . . O(amide2) | 1.93 | 2.793(1) | 171.1 |
| | N—H(amine) . . . O(amide2) | 2.14 | 3.047(2) | 170.0 |
| | N—H(amide1) . . . O(acid) | 2.01 | 2.878(2) | 163.9 |
| | N—H(amide1) . . . O(amide2) | 2.00 | 2.908(2) | 175.8 |

Table XXI includes important geometrical parameters of hydrogen bonding interaction distances. For example, the column "Distance (H . . . A) angstroms" includes the distances between the donor H-atom and the acceptor atom in angstroms. The column "Distance (D . . . A) angstroms" includes the distance between the electromagnetic atom to which the donor hydrogen atom is covalently bonded and the acceptor atom of another molecule in angstroms. The column "Theta (degrees)" includes the bond angle of the hydrogen bond. Specifically, this is the angle from the donor, through the hydrogen atom, and to the acceptor.

Example 3

Glyburide:TRIS Co-crystal

Glyburide (20.39 mg) and TRIS (tromethamine, 5 mg) were mixed in 1:1 mole ratio in 5 mL of methanol. The solution was kept overnight at 5 degrees C., decanted, and evaporated to dryness. DSC, TGA, and PXRD analyses were completed on the glyburide:TRIS co-crystal.

Figure 2:
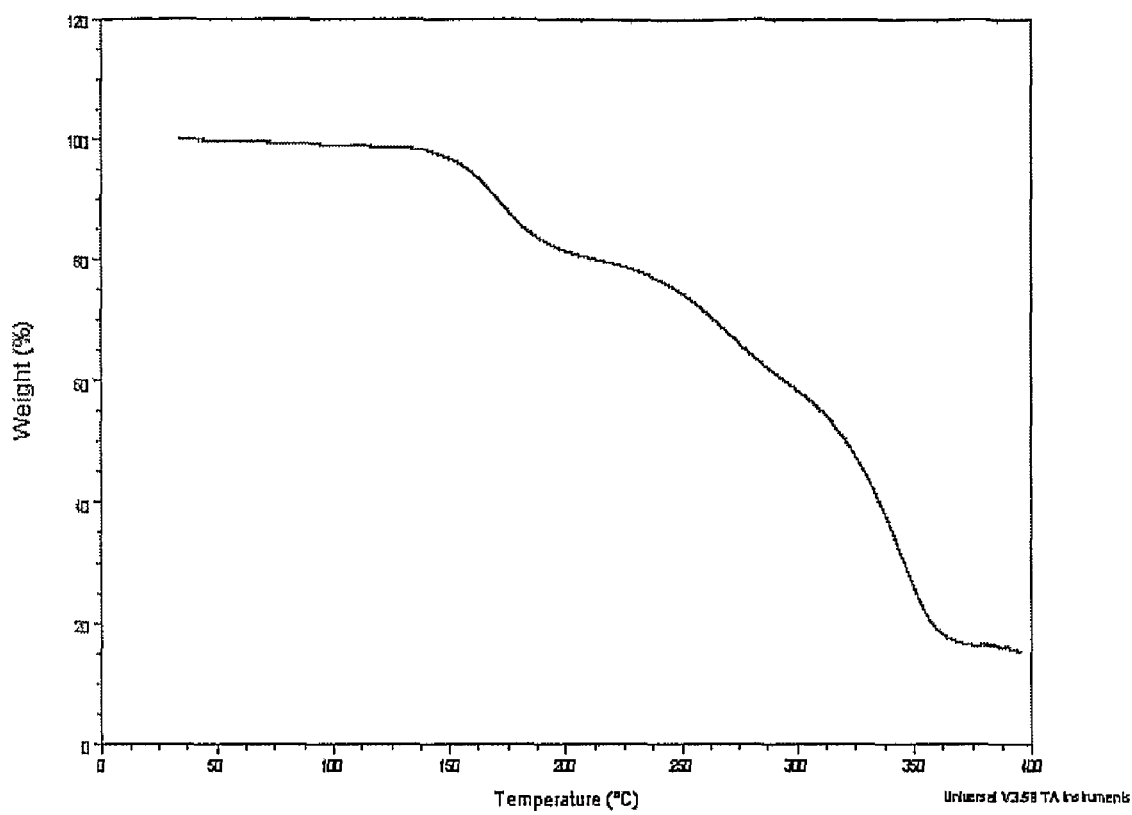
FIG. 2—TGA thermogram for glyburide:TRIS co-crystal.

DSC thermogram shows an endothermic transition at about 140 degrees C. (FIG. 1). TGA thermogram shows a weight loss of about 20 percent between about 150 degrees C. and about 200 degrees C. (FIG. 2).

Figure 3:
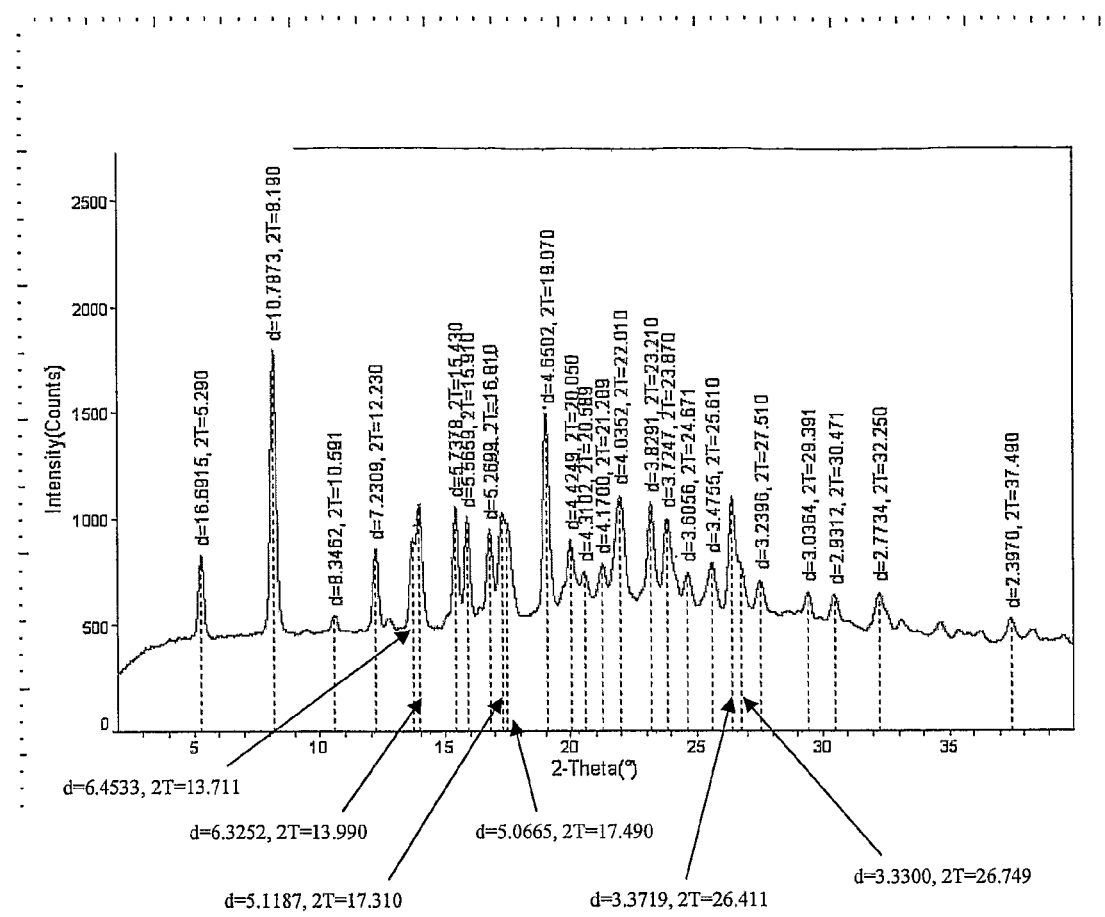
FIG. 3—PXRD diffractogram for glyburide:TRIS co-crystal.

The glyburide:TRIS co-crystal can be characterized by any one, any two, any three, any four, any five, or any six or more of the peaks in FIG. 3 including, but not limited to, 5.29, 8.19, 12.23, 13.99, 15.43, 15.91, 17.31, 19.07, 22.01, 23.21, 23.87, 25.61, and 26.41 degrees 2-theta (data as collected). FIG. 3 shows the PXRD diffractogram of the glyburide:TRIS co-crystal without background subtraction.

Example 4

Fluconazole maleate:Maleic acid Co-crystal

Fluconazole and maleic acid were dissolved in ethyl acetate with heat, then slowly evaporated. The co-crystal was characterized as a fluconazole maleate:maleic acid hydrate.

Crystal data: (Bruker SMART-APEX CCD Diffractometer), monoclinic C2; a=36.557(6) angstroms, b=5.695(6) angstroms, c=12.771(7) angstroms, beta=94.530 degrees, Z=4.

IR spectroscopy (Nicolet Avatar 320 FTIR) showed peaks at: 3121, 3055, 1702, 1562, 1430, 1257, 1217, 915, 857, and 787 $cm^{-1}$.

MEL-TEMP showed a melting point of about 84 degrees C. for the fluconazole maleate:maleic acid co-crystal.

Example 5

Oxcarbazepine Formic Acid Solvate

Oxcarbazepine was dissolved in formic acid using heat. The oxcarbazepine formic acid solvate was recovered via slow evaporation of the formic acid.

Crystal data: (Bruker SMART-APEX CCD Diffractometer), triclinic P-1; a=9.334(2) angstroms, b=10.757(2) angstroms, c=14.113(3) angstroms, alpha=97.020(4) degrees, beta=107.988(4) degrees, gamma=94.617(4), Z=2.

IR spectroscopy (Nicolet Avatar 320 FTIR) showed peaks at: 3419, 3187, 1717, 1658, 1595, 1397, 1147, and 767 $cm^{-1}$.

MEL-TEMP showed a melting point of about 223-225 degrees C. for the oxcarbazepine formic acid solvate.

Example 6

Piracetam:Gentisic acid Co-crystal

To piracetam (16 mg, 0.11 mol) was added gentisic acid (17 mg, 0.11 mol). To the solid mixture was added acetonitrile (1 mL) and the solution was heated at 70 degrees C. for 2 minutes. The homogeneous solution was then cooled to room temperature (22 degrees C.) and the solvent was slowly evaporated. After 24 hours at room temperature, a precipitate was observed. The precipitate was collected and dried, which gave a 1:1 piracetam:gentisic acid co-crystal as small colorless plates. The crystals were characterized using DSC, melting point (Mel-temp), IR, PXRD, and single crystal x-ray analysis.

Figure 4:
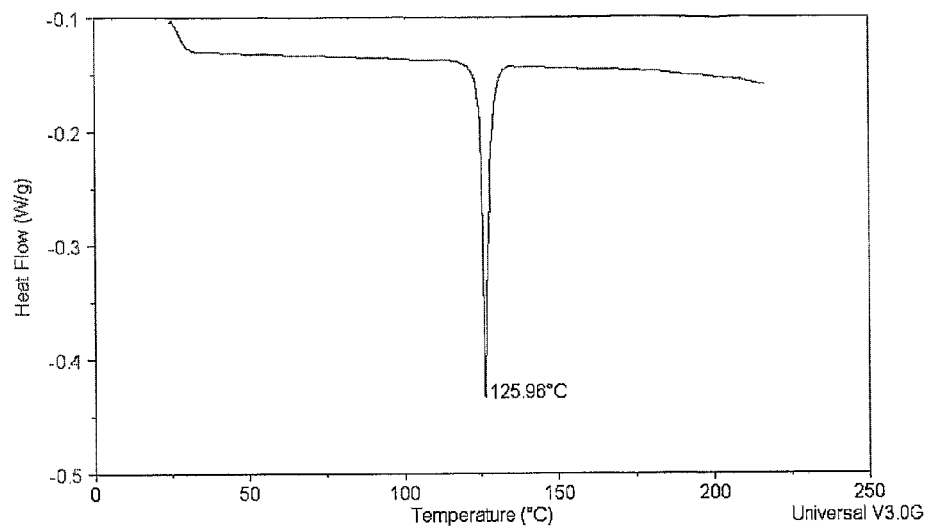
FIG. 4—DSC thermogram for piracetam:gentisic acid co-crystal.

DSC analysis of the piracetam:gentisic acid co-crystal showed an endothermic transition at about 126 degrees C., as shown in FIG. 4.

A MEL-TEMP was used to determine the melting point of the piracetam:gentisic acid co-crystal. The melting point was determined to be about 124 degrees C.

Figure 5:
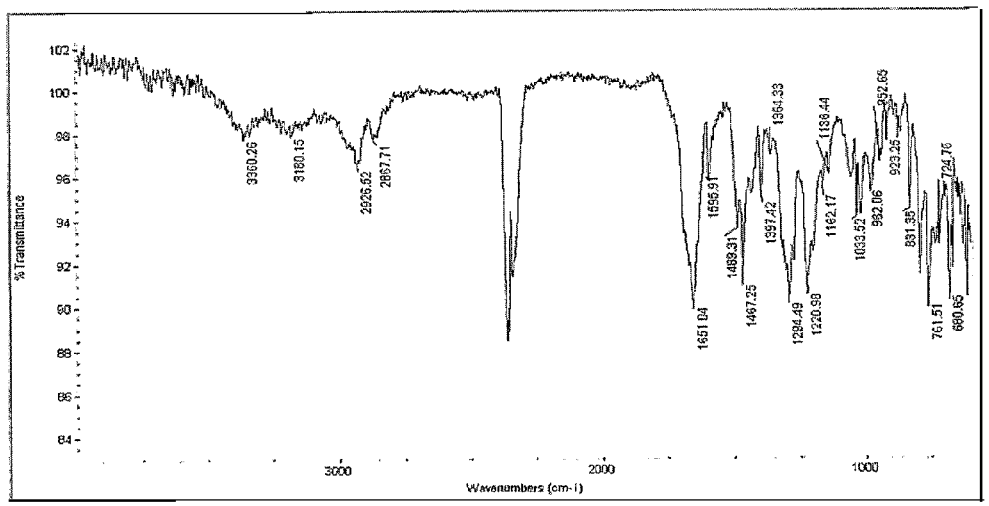
FIG. 5—IR spectrum for piracetam:gentisic acid co-crystal.

The piracetam:gentisic acid co-crystal was characterized by IR spectroscopy. The piracetam:gentisic acid co-crystal can be characterized by any one, any two, any three, any four, any five, or any six or more of the peaks in FIG. 5 including, but not limited to, 1651, 1596, 1467, 1294, 1221, 1034, 831, 762, and 681 $cm^{-1}$.

Figure 6:
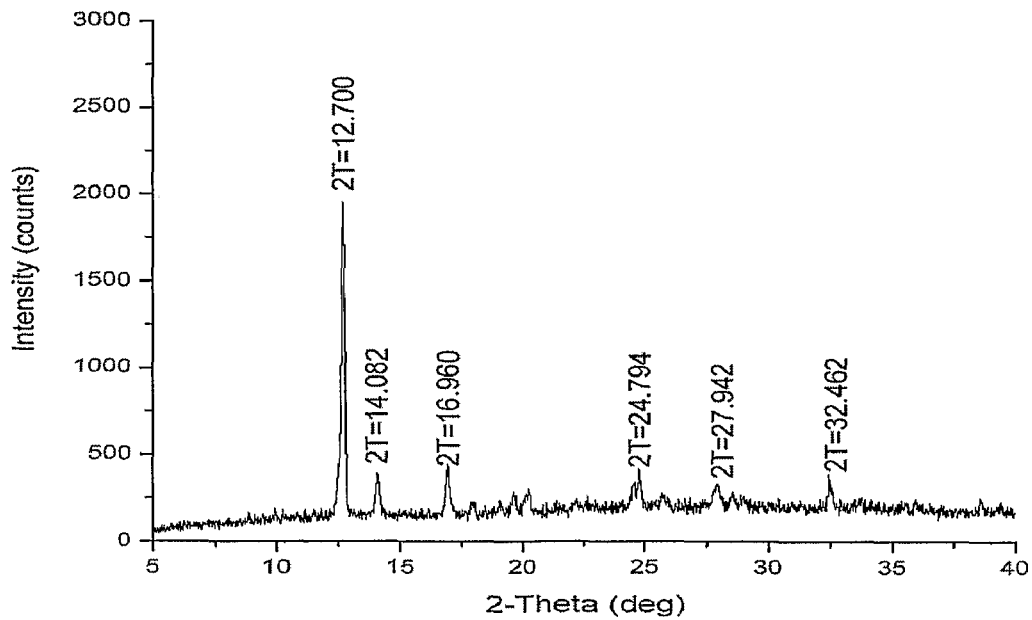
FIG. 6—PXRD diffractogram for piracetam:gentisic acid co-crystal.

The piracetam:gentisic acid co-crystal was also characterized by PXRD. The piracetam:gentisic acid co-crystal can be characterized by any one, any two, any three, any four, any five, or any six or more of the peaks in FIG. 6 including, but not limited to, 12.70, 14.08, 16.96, 24.79, 27.94, and 32.46 degrees 2-theta.

Single crystal x-ray data (Bruker SMART-APEX CCD): monoclinic C2/c, a=27.896(3) angstroms, b=5.1762(5) angstroms, c=19.7879(18) angstroms, alpha=90 degrees, beta=101.090(2) degrees, gamma=90 degrees, V=2803.9(4) cubic angstroms, T=100(2) K, Z=8.

Both piracetam and gentisic acid in their respective free forms are known to be polymorphic. Three polymorphs of piracetam can be found in the Cambridge Structural Database (CSD). In addition, the Merck Index describes gentisic acid as "dimorphic." The resulting piracetam:gentisic acid co-crystal from the above preparation may be non-polymorphic. After multiple experiments including dry grinding and wet grinding with several different solvents, only one polymorph of the piracetam:gentisic acid co-crystal has been observed.

Example 7

Piracetam:4-hydroxybenzoic acid Co-crystal

To piracetam (10 mg, 0.07 mol) was added 4-hydroxybenzoic acid (10 mg, 0.07 mol). To the solid mixture was added acetonitrile (1 mL) and the solution was heated at 70 degrees C. for 5 minutes. The homogeneous solution was then cooled to room temperature and the solvent was slowly evaporated. After 24 hours at room temperature (22 degrees C.), a precipitate was observed. The precipitate was collected and dried, which gave a 1:1 piracetam:4-hydroxybenzoic acid co-crystal as small colorless plates. The crystals were characterized using DSC, melting point (Mel-temp), IR, PXRD, and single crystal x-ray analysis.

Figure 7:
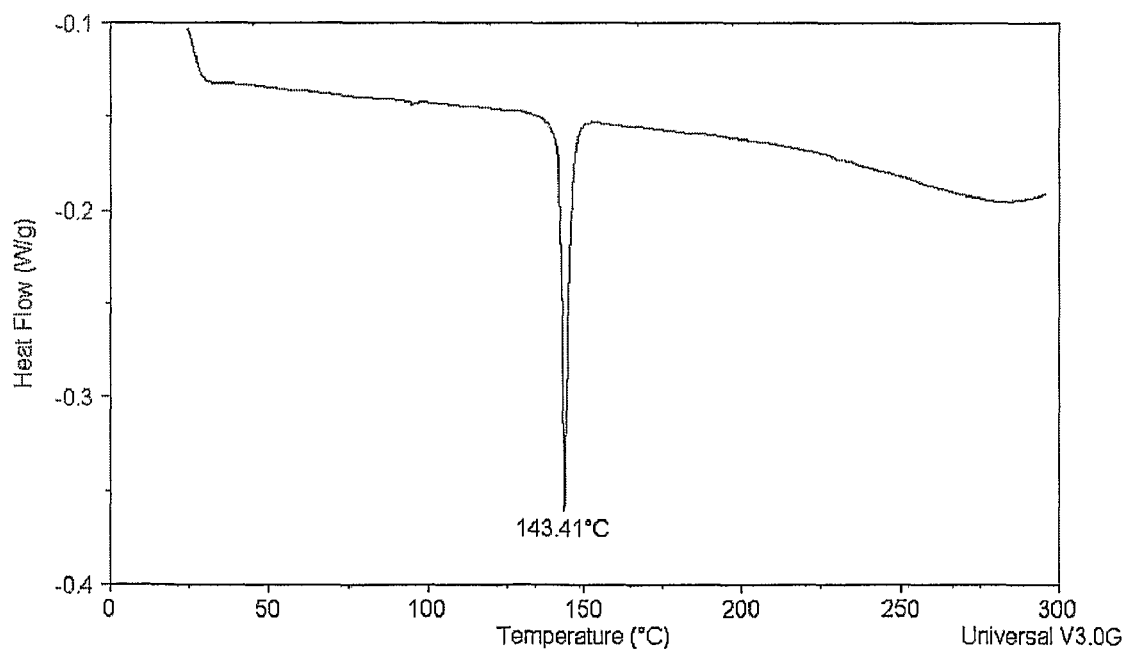
FIG. 7—DSC thermogram for piracetam:4-hydroxybenzoic acid co-crystal.

DSC analysis of the piracetam:4-hydroxybenzoic acid co-crystal showed an endothermic transition at about 143 degrees C., as shown in FIG. 7.

A MEL-TEMP was used to determine the melting point of the piracetam:4-hydroxybenzoic acid co-crystal. The melting point was determined to be 141-142 degrees C.

Figure 8:
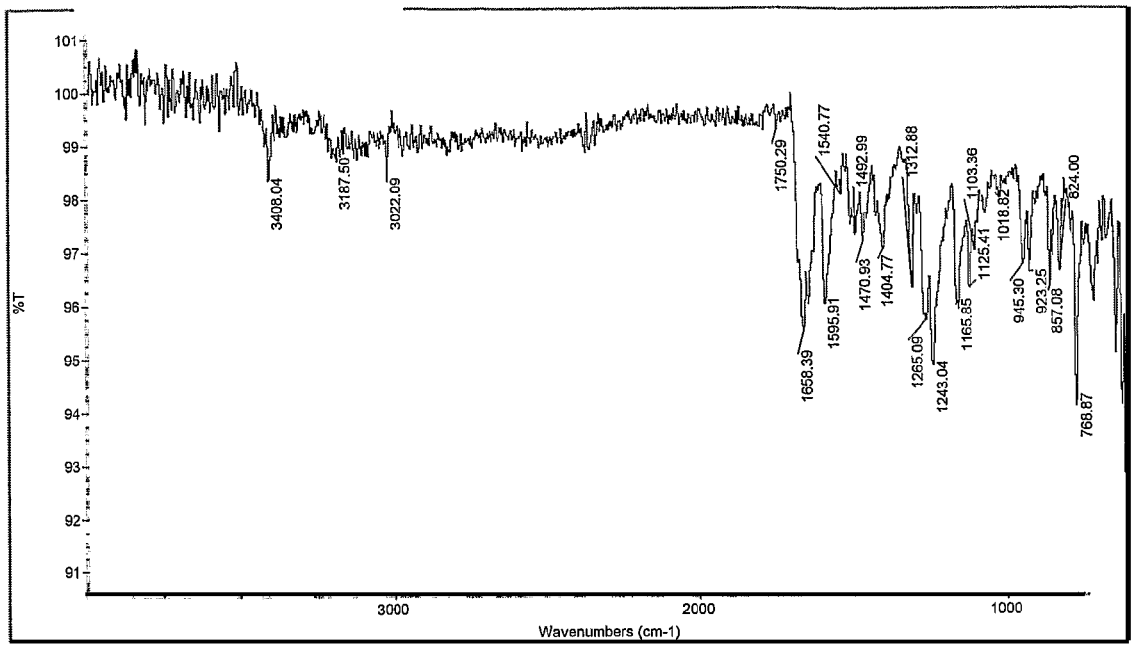
FIG. 8—IR spectrum for piracetam:4-hydroxybenzoic acid co-crystal.

The piracetam:4-hydroxybenzoic acid co-crystal was characterized by IR spectroscopy. The piracetam:4-hydroxybenzoic acid co-crystal can be characterized by any one, any two, any three, any four, any five, or any six or more of the peaks in FIG. 8 including, but not limited to, 1658, 1596, 1471, 1405, 1265, 1243, 1166, 1125, 945, 923, 857, and 769 cm$^{-1}$.

Figure 9:
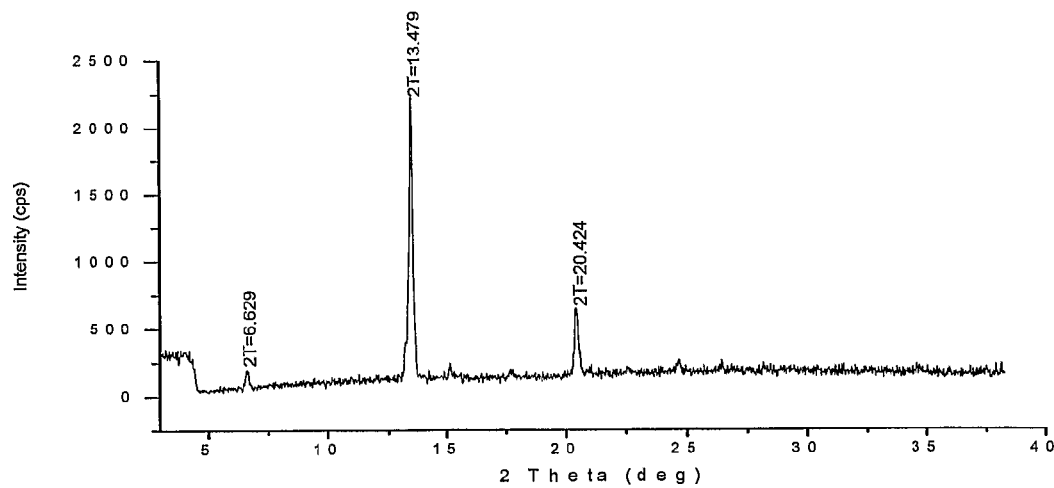
FIG. 9—PXRD diffractogram for piracetam:4-hydroxybenzoic acid co-crystal.

The piracetam:4-hydroxybenzoic acid co-crystal was also characterized by PXRD. The piracetam:4-hydroxybenzoic acid co-crystal can be characterized by any one, any two, any three, any four, any five, or any six or more of the peaks in FIG. 9 including, but not limited to, 6.63, 13.48, and 20.42 degrees 2-theta.

Single crystal x-ray data (Bruker SMART-APEX CCD): monoclinic P2(1)/n, a=14.780(3) angstroms, b=5.5029(12) angstroms, c=17.068(4) angstroms, alpha=90 degrees, beta=109.557(4) degrees, gamma=90 degrees, V=1308.0(5) cubic angstroms, T=100(2) K, Z=4.

Example 8

Carbamazepine:Cinnamic acid Co-crystal

To carbamazepine (12 mg, 0.05 mol) was added cinnamic acid (8 mg, 0.05 mol). To the solid mixture was added ethyl acetate (1 mL) and the solution was heated at 70 degrees C. for 5 minutes. The homogeneous solution was then cooled to room temperature (about 22 degrees C.) and the solvent was slowly evaporated. After 24 hours at room temperature, a precipitate was observed, collected, and dried to give a 1:1 carbamazepine:cinnamic acid co-crystal as large colorless rods. The crystals were characterized using DSC, MEL-TEMP, PXRD, IR and single-crystal x-ray analysis.

Figure 10:
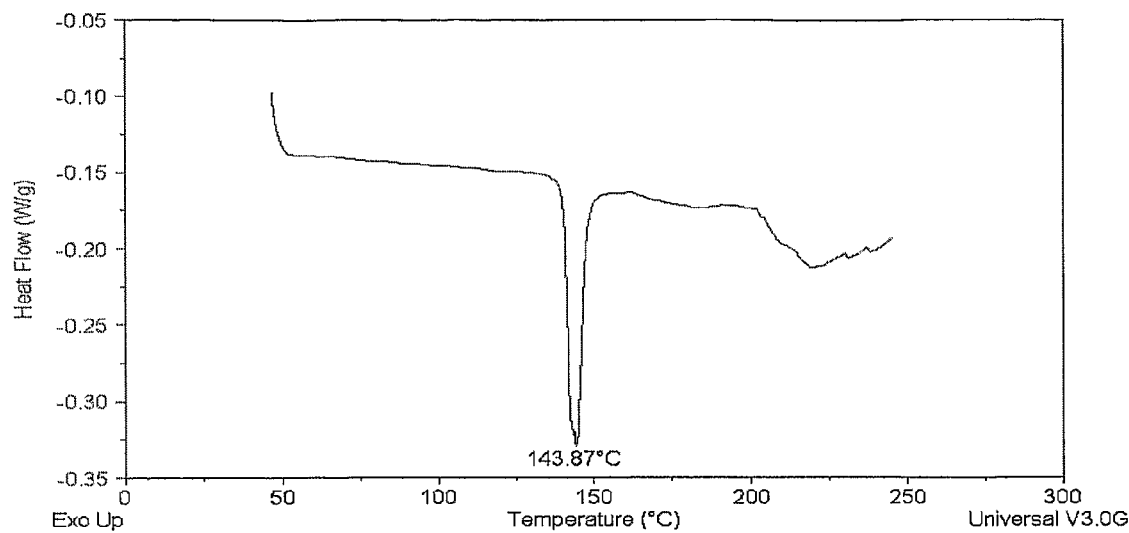
FIG. 10—DSC thermogram for carbamazepine:cinnamic acid co-crystal.
Figure 11:
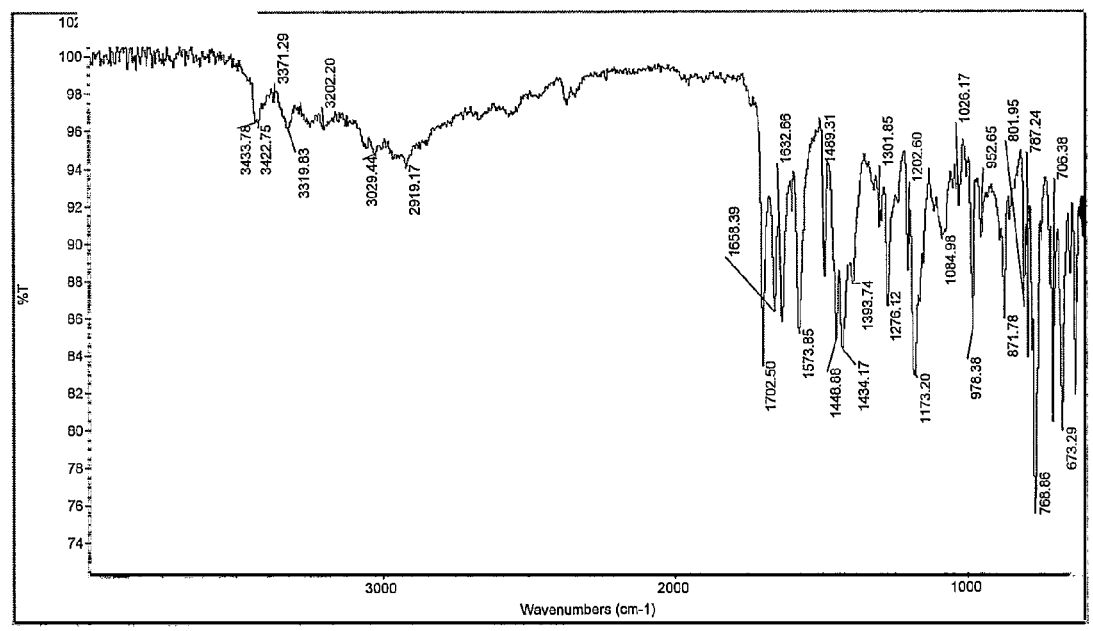
FIG. 11—IR spectrum for carbamazepine:cinnamic acid co-crystal.
Figure 12:
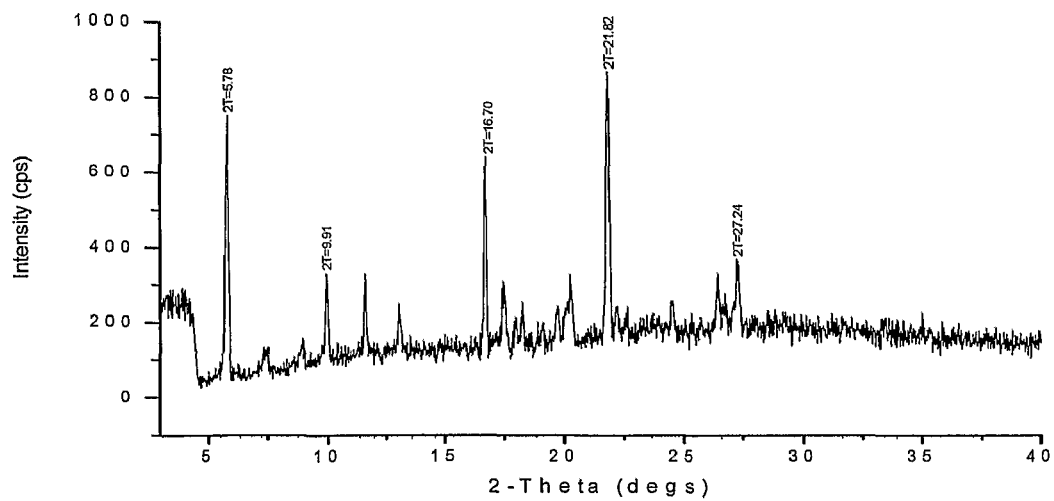
FIG. 12—PXRD diffractogram for carbamazepine:cinnamic acid co-crystal.

DSC thermogram shows an endothermic transition at about 144 degrees C. (FIG. 10). The carbamazepine:cinnamic acid co-crystal can be characterized by any one, any two, any three, any four, any five, or any six or more of the IR peaks in FIG. 11 including, but not limited to, 1703, 1658, 1633, 1574, 1489, 1449, 1434, 1276, 1173, 978, 872, 769, 706, and 673 cm$^{-1}$. A MEL-TEMP was used to determine the melting point of the carbamazepine:cinnamic acid co-crystal. The melting point was determined to be about 142-143 degrees C. The carbamazepine:cinnamic acid co-crystal can be characterized by any one, any two, any three, any four, any five, or any six or more of the PXRD peaks in FIG. 12 including, but not limited to, 5.78, 9.91, 16.70, 21.82, and 27.24 degrees 2-theta.

Single crystal x-ray data (Bruker SMART-APEX CCD): monoclinic P2(1)/c, a=15.2187(15) angstroms, b=5.4243(5) angstroms, c=23.435(2) angstroms, alpha=90 degrees, beta=95.346(2) degrees, gamma=90 degrees, V=1926.1(3) cubic angstroms, T=100 K, Z=4.

Example 9

Carbamazepine:Acetylsalicylic acid Co-crystal

To carbamazepine (18 mg, 0.08 mol) was added acetylsalicylic acid (14 mg, 0.08 mol). To the solid mixture was added ethyl acetate (1 mL) and the solution was heated at 70 degrees C. for 5 minutes. The homogeneous solution was then cooled to room temperature (about 22 degrees C.) and the solvent was slowly evaporated. After 24 hours at room temperature, a precipitate was observed, collected, and dried to give a 1:1 carbamazepine:acetylsalicylic acid co-crystal as small colorless plates. The crystals were characterized using DSC, MEL-TEMP, PXRD, IR, and single-crystal x-ray analysis.

Figure 13:
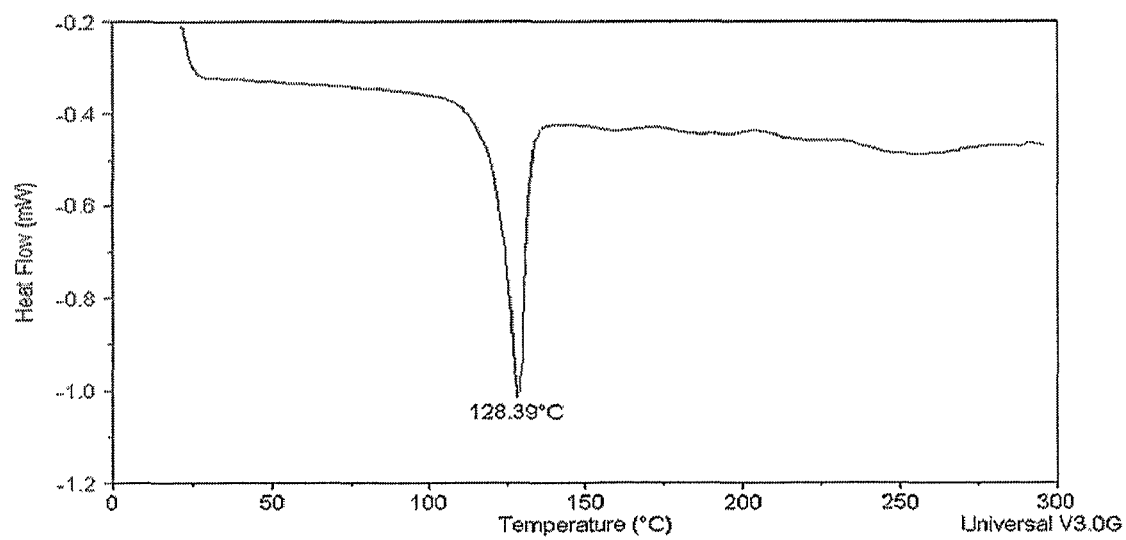
FIG. 13—DSC thermogram for carbamazepine:acetylsalicylic acid co-crystal.
Figure 14:
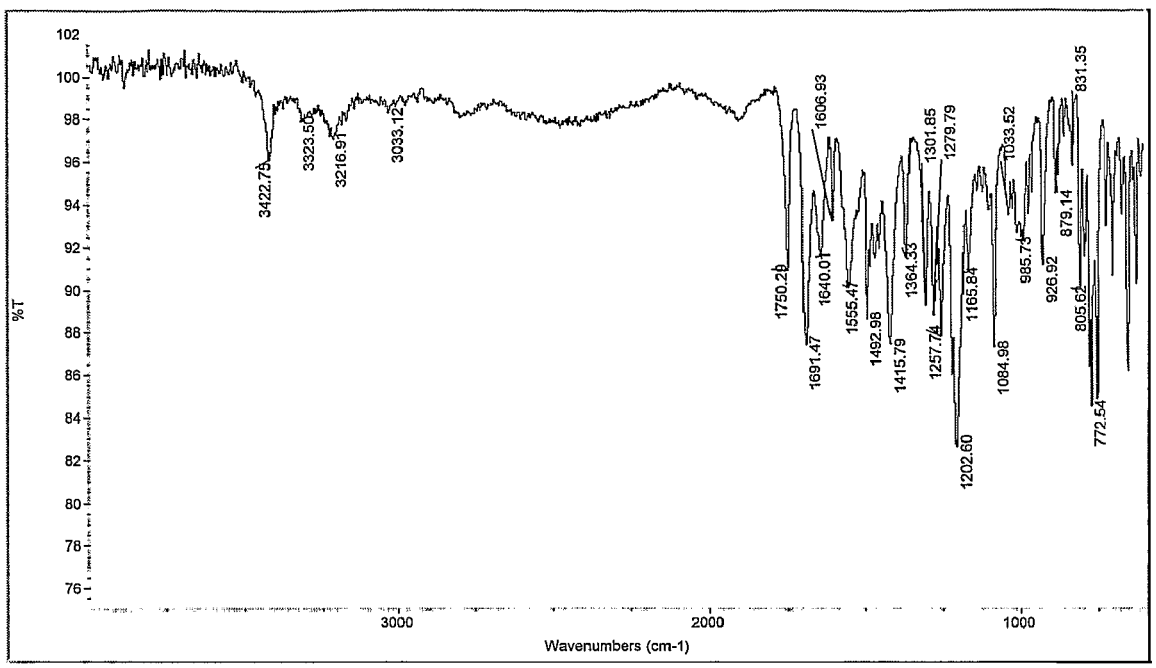
FIG. 14—IR spectrum for carbamazepine:acetylsalicylic acid co-crystal.
Figure 15:
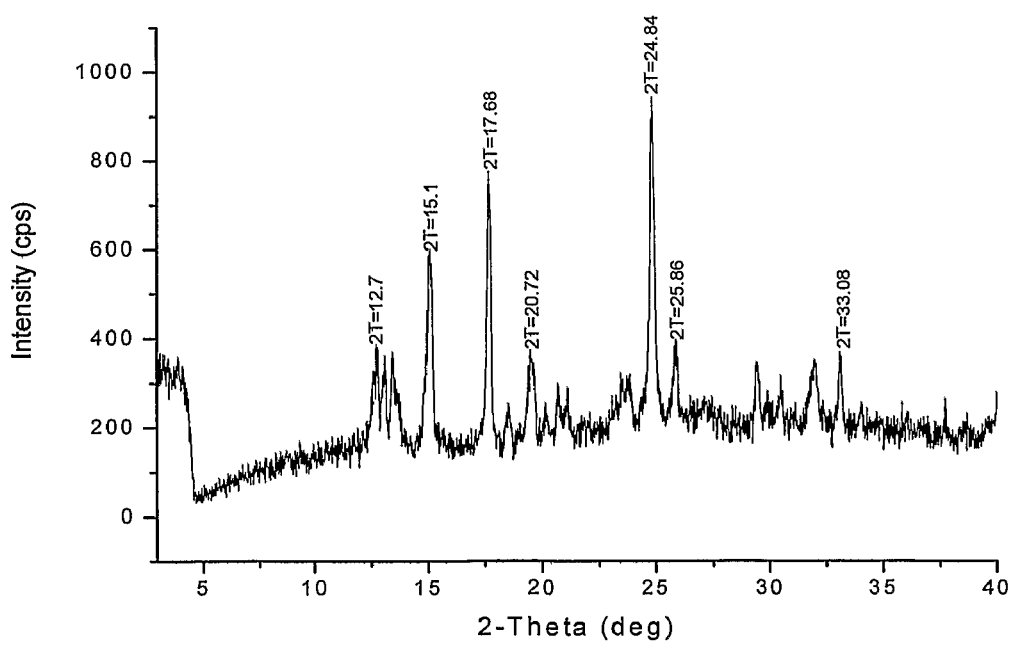
FIG. 15—PXRD diffractogram for carbamazepine:acetylsalicylic acid co-crystal.

DSC thermogram shows an endothermic transition at about 128 degrees C. (FIG. 13). The carbamazepine:acetylsalicylic acid co-crystal can be characterized by any one, any two, any three, any four, any five, or any six or more of the IR peaks in FIG. 14 including, but not limited to, 1750, 1691, 1640, 1607, 1555, 1493, 1416, 1364, 1302, 1280, 1258, 1203, 1085, 986, 927, 806, and 773 cm$^{-1}$. A MEL-TEMP was used to determine the melting point of the carbamazepine:acetylsalicylic acid co-crystal. The melting point was determined to be about 125-126 degrees C. The carbamazepine:acetylsalicylic acid co-crystal can be characterized by any one, any two, any three, any four, any five, or any six or more of the PXRD peaks in FIG. 15 including, but not limited to, 12.7, 15.1, 17.68, 20.72, 24.84, 25.86, and 33.08 degrees 2-theta.

Single crystal x-ray data (Bruker SMART-APEX CCD): triclinic P-1, a=9.0317(18) angstroms, b=11.364(2) angstroms, c=11.424(2) angstroms, alpha=60.350(4) degrees, beta=85.599(4) degrees, gamma=84.724(4) degrees, V=1014.0(3) cubic angstroms, T=100(2) K, Z=2.

Example 10

Stavudine:Melamine Co-crystal

To stavudine (132 mg, 0.58 mmol) was added melamine (34 mg, 0.27 mmol). To the solid mixture was added 1:1 ethanol:water (2 mL) and the solution was heated for 5 minutes at approximately 40 degrees C. The homogeneous solution was then allowed to cool to room temperature (about 22 degrees C.) and allowed to slowly evaporate in an unmodified atmosphere. After 4 days, a precipitate was observed, collected, and dried to give a 3:1 stavudine:melamine co-crystal as small colorless plates. The crystals were characterized using DSC, IR, PXRD, MEL-TEMP, and single-crystal x-ray analysis.

Figure 16:
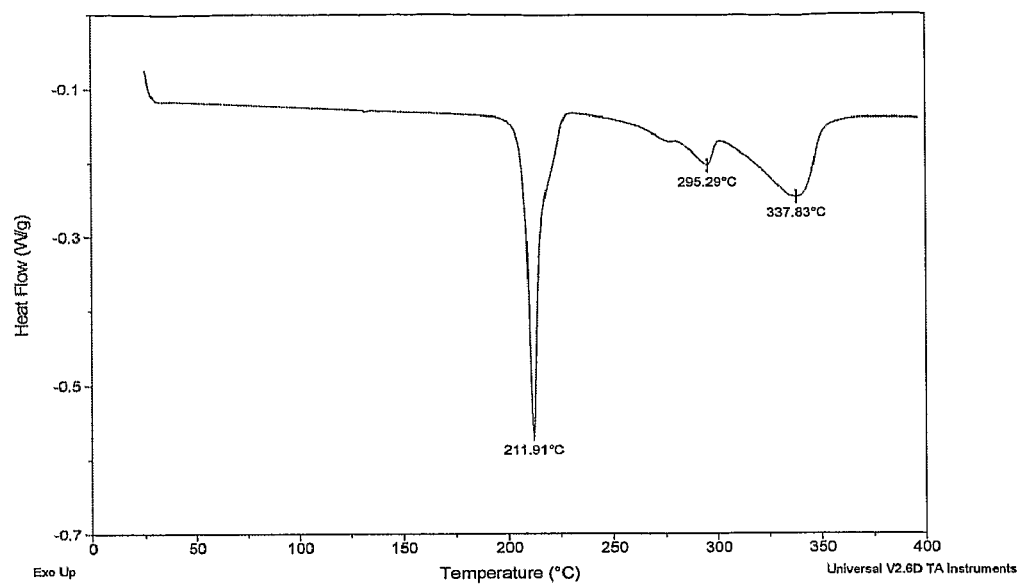
FIG. 16—DSC thermogram for stavudine:melamine co-crystal.
Figure 17A:
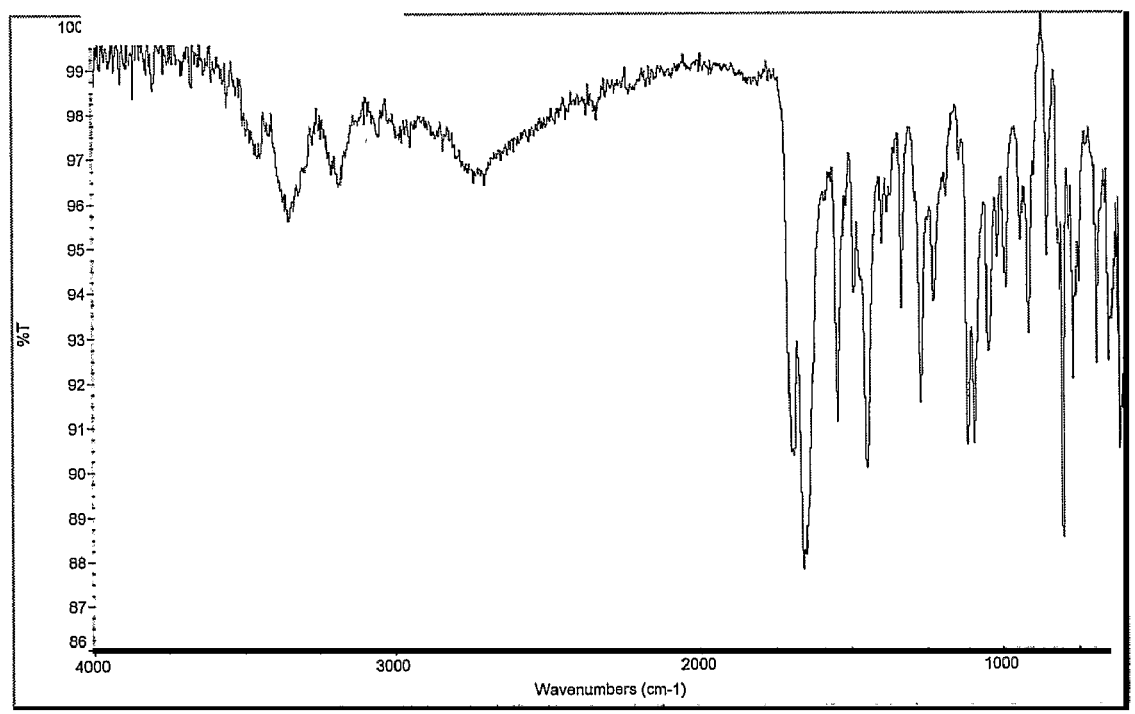
FIGS. 17A and 17B—IR spectrum for stavudine:melamine co-crystal.
Figure 17B:
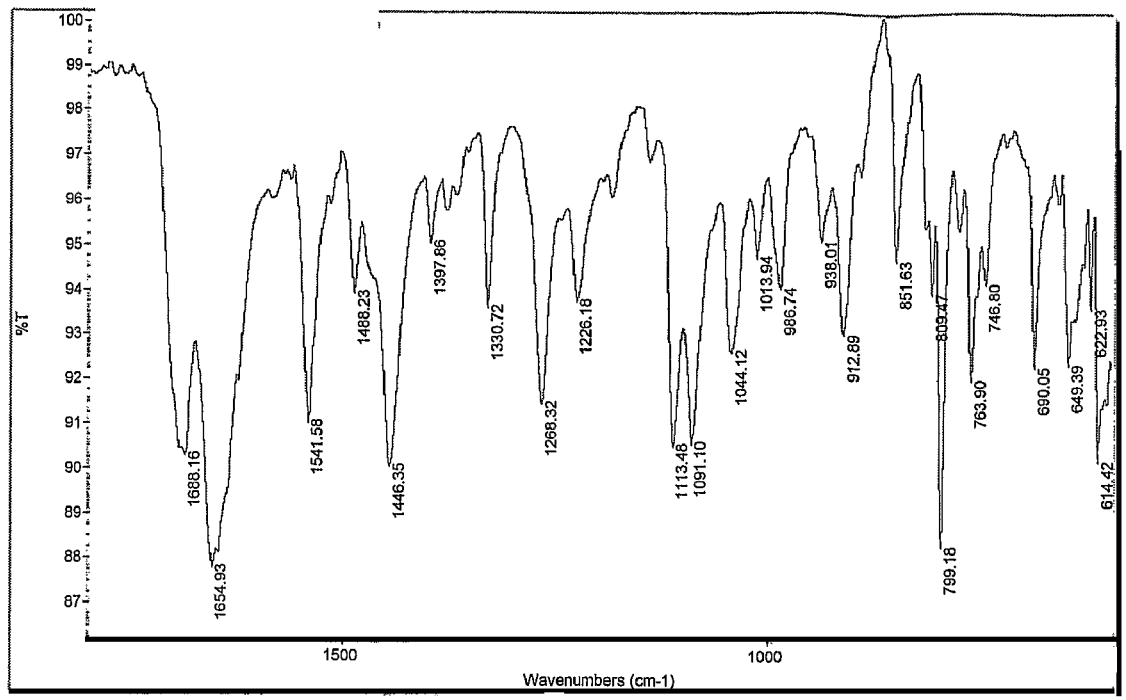

DSC thermogram shows an endothermic transition at about 212 degrees C. (FIG. 16). The stavudine:melamine co-crystal can be characterized by any one, any two, any three, any four, any five, or any six or more of the IR peaks in FIG. 17B including, but not limited to, 1688, 1655, 1542, 1446, 1268, 1113, 1091, 1044, 799, 690, and 614 cm$^{-1}$. (FIG. 17A shows the IR spectrum of the stavudine:melamine co-crystal, FIG. 17B shows the same spectrum with the fingerprint region expanded.) A MEL-TEMP was used to determine the melting point of the stavudine:melamine co-crystal. The melting point was determined to be about 186-190 degrees C. The stavudine:melamine co-crystal can be characterized by any one, any two, any three, any four, any five, or any six or more of the PXRD peaks in FIG. 18 including, but not limited to, 11.06, 18.32, 20.24, 22.4, 24.64, 28.08, and 33.92 degrees 2-theta.

Single crystal x-ray data (Bruker SMART-APEX CCD): monoclinic C2, a=28.720(4) angstroms, b=16.622(3) angstroms, c=15.900(2) angstroms, alpha=90 degrees, beta=102.909(3) degrees, gamma=90 degrees, V=7398.3(19) cubic angstroms, T=100(2) K, Z=8.

Example 11

Stavudine:2-aminopyridine Co-crystal

To stavudine (40 mg, 0.18 mmol) was added 2-aminopyridine (17 mg, 0.18 mmol). To the solid mixture was added 1:1 ethanol:water (2 mL) and the solution heated until dissolved. The homogeneous solution was then allowed to cool to room temperature (about 22 degrees C.) and allowed to slowly evaporate in an unmodified atmosphere. After a few days, a precipitate was observed, collected, and dried to give a 1:1 stavudine:2-aminopyridine co-crystal as colorless blocks. The crystals were characterized using DSC, IR, MEL-TEMP, and single-crystal x-ray analysis.

Figure 19:
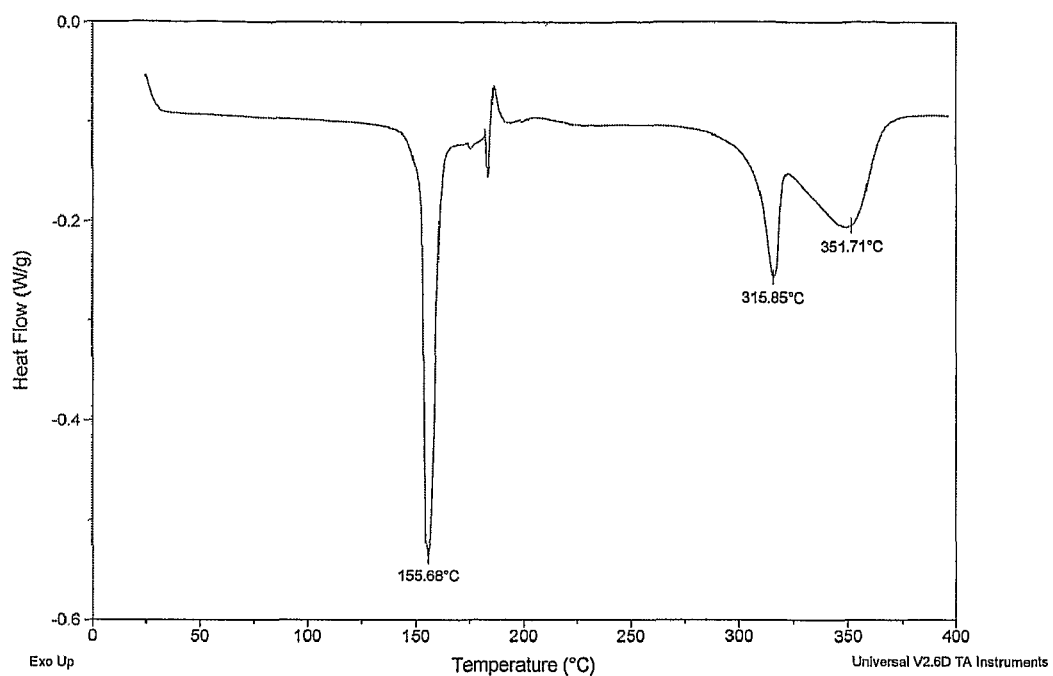
FIG. 19—DSC thermogram for stavudine:2-aminopyridine co-crystal.
Figure 20A:
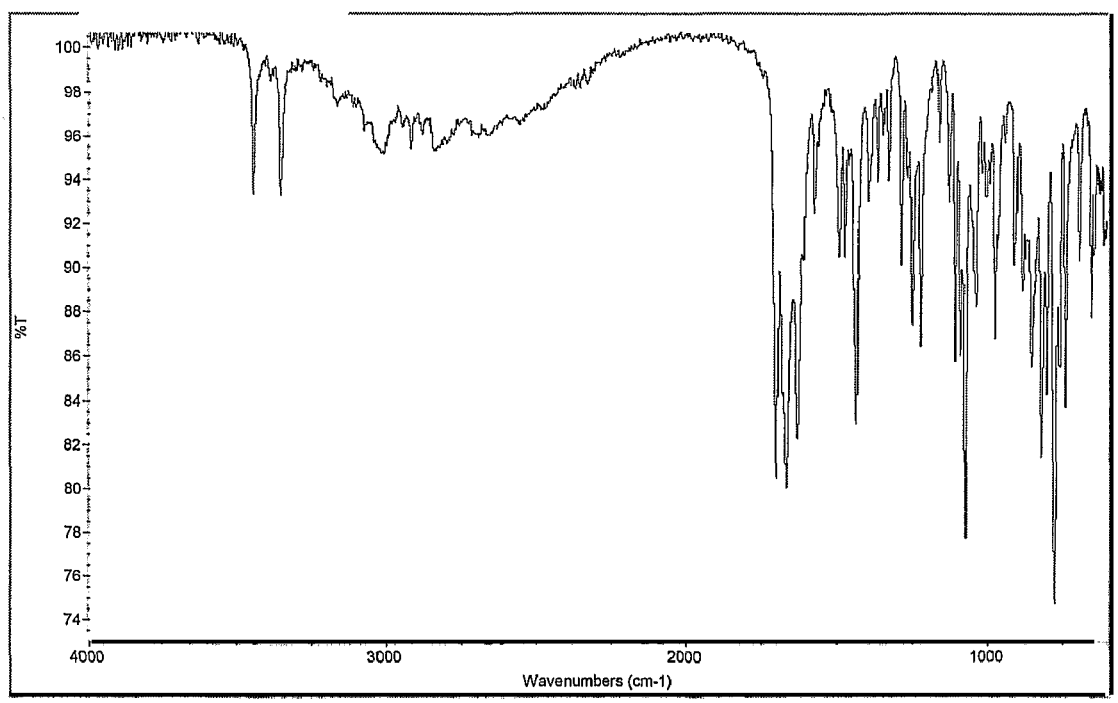
FIGS. 20A and 20B—IR spectrum for stavudine:2-aminopyridine co-crystal.
Figure 20B:
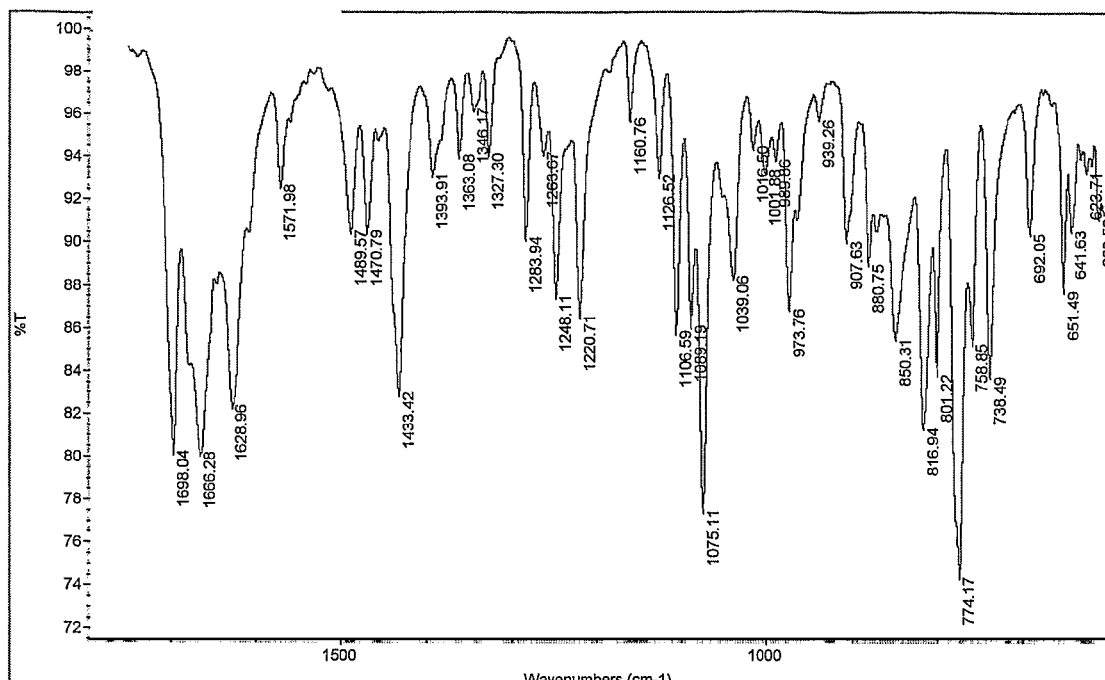

DSC thermogram shows an endothermic transition at about 156 degrees C. (FIG. 19). The stavudine:2-aminopyridine co-crystal can be characterized by any one, any two, any three, any four, any five, or any six or more of the IR peaks in FIG. 20B including, but not limited to, 1698, 1666, 1629, 1490, 1471, 1433, 1284, 1248, 1221, 1107, 1089, 1075, 1039, 974, 817, 774, 738, 692, 651, and 576 $cm^{-1}$. (FIG. 20A shows the IR spectrum of the stavudine:2-aminopyridine co-crystal, FIG. 20B shows the same spectrum with the fingerprint region expanded.) A MEL-TEMP was used to determine the melting point of the stavudine:2-aminopyridine co-crystal. The melting point was determined to be about 120-122 degrees C.

Single crystal x-ray data (Bruker SMART-APEX CCD): orthorhombic $P2_12_12_1$, a=7.1242(6) angstroms, b=13.7996(12) angstroms, c=15.0613(2) angstroms, alpha=90 degrees, beta=90 degrees, gamma=90 degrees, V=1476.3(2) cubic angstroms, T=100(2) K, Z=4.

TABLE I

| Co-Crystal Former | MW (g/mol) | MP (° C.) | Class | Functionality | # acceptors | # donors | Molecular Structure | pKa Values |
|---|---|---|---|---|---|---|---|---|
| 1-Hydroxy-2-naphthoic acid | 188.18 | 191-192 | 2 | Carboxylic acid, alcohol | 1 | 2 | | 2.7, 13.5 |
| 4-aminobenzoic acid | 137.14 | 187-188 | 2 | Amine, carboxylic acid | 1 | 3 | | 4.7, 4.8 |
| 4-aminopyridine | 94.11 | 158-159 | 3 | Amine, pyridine | 1 | 2 | | 10 |
| 4-Chlorobenzenesulfonic acid | 192.63 | 67 | 1 | $SO_3H$ | 3 | 1 | | 0-1 |
| 4-ethoxyphenyl urea | 180.2 | 173-174 | 3 | Amide, NH | 2 | 3 | | ~7-9 |
| 7-oxo-DHEA | 303 | 190-192 | 1 | Alcohol, Ketone | 3 | 1 | | |
| Acesulfame | 163.15 | 123-124 | 3 | $SO_2$, Amide | 4 | 1 | | ~5-7 |
| Acetohydroxamic acid | 75.07 | 89-92 | 3 | Amide, NH, OH | 2 | 2 | | 8.7 |

TABLE I-continued

| Co-Crystal Former | MW (g/mol) | MP (° C.) | Class | Functionality | # acceptors | # donors | Molecular Strucutre | pKa Values |
|---|---|---|---|---|---|---|---|---|
| Adenine | 135.13 | 220 (sub.) | 1 | Amine, NH | 3 | 3 | | 3.8 |
| Adipic Acid | 146.14 | 152 | 1 | Carboxylic acid | 2 | 2 | HOOC(CH$_2$)$_4$COOH | 4.44, 5.44 |
| Alanine | 89.09 | 289-291 | 1 | Amine, carboxillic acid | 1 | 3 | | 2.35, 9.87 |
| Allopurinaol | 136.11 | >350 | 3 | OH, NH | 4 | 2 | | 10.2 |
| Arginine | 174.2 | 244 (dec.) | 1 | Amine, COOH | 2 | 7 | | 2.18, 9.09, 13.2 |
| Ascorbic acid | 176.12 | 190-192 | 1 | C=O, OH | 6 | 4 | | 4.17, 11.57 |
| Asparagine | 132.12 | 234-235 | 1 | Amine, amide, COOH | 3 | 5 | | 2.02, 8.5 |
| Aspartic acid | 133.1 | 270-271 | 1 | Amine, COOH | 2 | 4 | | 1.88, 3.65, 9.60 |
| Benzenesulfonic Acid | 158.18 | 43-44 | 1 | SO$_3$H | 2 | 1 | | 0.70, 1.58 |
| Benzoic acid* | 122.12 | 122-123 | 2 | COOH | 1 | 1 | | 4.19 |
| Caffeine | 194.19 | 238 | 3 | C=O | 3 | 0 | | |

TABLE I-continued

| Co-Crystal Former | MW (g/mol) | MP (° C.) | Class | Functionality | # acceptors | # donors | Molecular Structure | pKa Values |
|---|---|---|---|---|---|---|---|---|
| Camphoric acid | 200.23 | 186-189 | 2 | Carboxylic acid | 2 | 2 | | 4.72, 5.83 |
| Capric acid | 172.27 | 31.4 | 1 | Carboxylic acid | 1 | 1 | $CH_3(CH_2)_8COOH$ | 4.9 |
| Chrysin | 254.24 | 285 | 1 | Phenol, ether, ketone | 2 | 2 | | |
| Cinnamic acid | 144.2 | 133 | 3 | Carboxylic acid | 1 | 1 | | 4.4 |
| Citric Acid | 192.12 | 153 | 1 | OH, COOH | 4 | 4 | | 3.13, 4.76, 6.40 |
| Clemizole | 325.84 | 167 | 1 | Pyrrolidine | 3 | 0 | | |
| Cyclamic acid | 179.24 | 169-170 | 3 | NH, $SO_3H$ | 2 | 2 | | −2 |
| Cysteine | 121.15 | — | 1 | Amine, COOH SH | 2 | 4 | | 1.71, 8.33, 10.78 |
| Dimethylglycine | 103.1 | 178-192 | 1 | Amine, Carboxylic acid | 2 | 1 | | 2.5 |

TABLE I-continued

| Co-Crystal Former | MW (g/mol) | MP (° C.) | Class | Functionality | # acceptors | # donors | Molecular Structure | pKa Values |
|---|---|---|---|---|---|---|---|---|
| D-Ribose | 150.13 | 87 | 1 | Alcohol, ether | 1 | 4 | 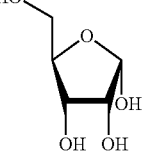 | |
| Fumaric acid | 116.07 | 287 | 1 | COOH | 2 | 2 | 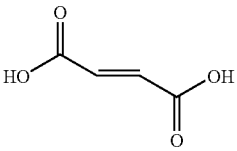 | 3.03, 4.38 |
| Galactaric acid | 210.14 | 255 (dec) | 1 | Carboxylic acid, alcohol | 2 | 6 | 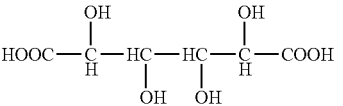 | 3.08, 3.63 |
| Genistein | 270.24 | 297-298 | 1 | Alcohol, Phenol, ether, ketone | 2 | 3 | 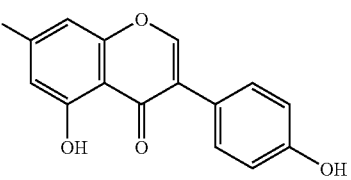 | |
| Gentisic acid | 154.12 | 199-200 form I, 205 form II | 2 | Carboxylic acid, alcohol, phenol | 1 | 3 | 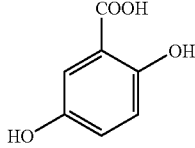 | 2.93 |
| Glucamine, N-Methyl | 195.22 | 128-129 | 1 | Alcohol, Amine | 5 | 6 | 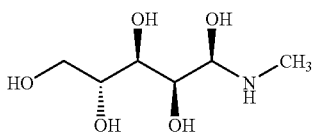 | 8.03(B) |
| Gluconic acid | 196.15 | 131 | 1 | OH, COOH | 6 | 6 | 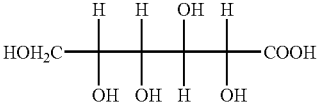 | 3.76 |
| Glucosamine | 179.17 | 88 | 1 | OH | 5 | 6 | 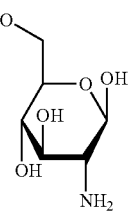 | 6.91 |
| Glucuronic acid | 194.14 | 165 | 1 | Carboxylic acid, alcohol, aldehyde | 2 | 5 | 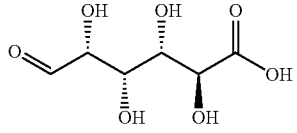 | 3.18 |

TABLE I-continued

| Co-Crystal Former | MW (g/mol) | MP (° C.) | Class | Functionality | # acceptors | # donors | Molecular Structure | pKa Values |
|---|---|---|---|---|---|---|---|---|
| Glutamic acid | 147.13 | 160 | 1 | Amine, COOH | 2 | 4 | | 2.19, 4.25, 9.67 |
| Glutamine | 146.15 | 185-186 | 1 | Amine, Amide, COOH | 2 | 5 | | 2.17, 9.13 |
| Glutaric acid | 132.11 | 98-98 | 1 | COOH | 2 | 2 | | 2.7, 4.5 |
| Glycine | 75.07 | 182 | 1 | Amine, COOH | 2 | 3 | | 2.34, 9.6 |
| Glycolic acid | 76.05 | 80 | 1 | OH, COOH | 2 | 2 | | 3.82 |
| Hippuric acid | 179.17 | 187-188 | 1 | Amide, NH, COOH | 2 | 2 | | 3.55 |
| Histidine | 155.16 | 287 (dec.) | 1 | Amine, COOH, Imidazole | 2 | 4 | | 1.78, 5.97, 8.97 |
| Hydroquinone* | 110.11 | 170-171 | 2 | OH, Phenol | 2 | 2 | | ~10 |
| Imidazole | 68.08 | 90-91 | 1 | NH | 1 | 1 | | 6.92 |
| Ipriflavone | 280.32 | 115-117 | 1 | Ketone, ether | 3 | 0 | | |
| Isoleucine | 131.17 | 168-170 (sub.) | 1 | Amine, COOH | 1 | 3 | | 2.32, 9.76 |

TABLE I-continued

| Co-Crystal Former | MW (g/mol) | MP (° C.) | Class | Functionality | # acceptors | # donors | Molecular Structure | pKa Values |
|---|---|---|---|---|---|---|---|---|
| Lactobionic acid | 358.3 | 128-130 | 2 | Alcohol, carboxylic acid, ether | 1 | 9 | 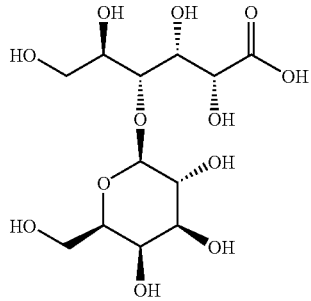 | 3.2 |
| Lauric acid | 200.32 | 44-48 | 1 | Carboxylic acid | 1 | 1 | CH₃(CH₂)₁₀COOH | ~4.5 |
| Leucine | 131.17 | 145-148 (sub.) | 1 | Carboxylic acid, amine | 1 | 3 | 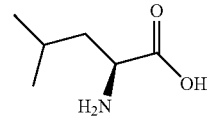 | 2.36, 9.6 |
| Lysine | 146.19 | 225 (dec.) | 1 | Amine, COOH | 1 | 5 | 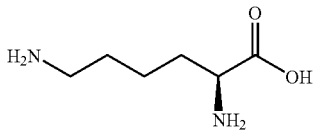 | 2.2, 8.9, 10.28 |
| Maleic | 116.07 | 138-139 | 1 | COOH | 2 | 2 | 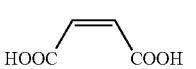 | 1.92, 6.23 |
| Malic acid | 134.09 | 131-132 | 1 | OH, COOH | 3 | 3 | 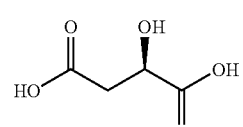 | 3.46, 5.1 |
| Malonic | 104.06 | 135 | 1 | COOH | 2 | 2 | 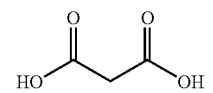 | 2.83, 5.70 |
| Mandelic acid | 152.15 | 119 | 1 | OH, COOH | 2 | 2 | 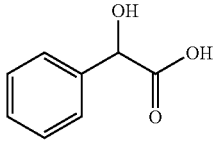 | 3.37 |
| Methionine | 149.21 | 280-282 (dec.) | 1 | Amine, COOH, S—Me | 2 | 3 | 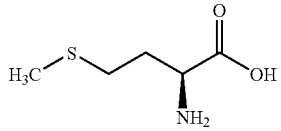 | 2-3, 9 |
| Nicotinamide | 122.12 | 128-131 | 1 | Pyridine, amide | 2 | 2 | 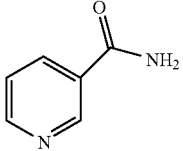 | 3.3 |

TABLE I-continued

| Co-Crystal Former | MW (g/mol) | MP (° C.) | Class | Functionality | # acceptors | # donors | Molecular Structure | pKa Values |
|---|---|---|---|---|---|---|---|---|
| Nicotinic acid | 123.11 | 236-237 | 2 | Carboxylic acid, pyridine | 2 | 1 | | 2.07(B), 4.85 |
| Orotic acid | 156.1 | 345-346 | 2 | Carboxilic acid, lactam | 3 | 3 | | 5.85, 8.95 |
| Oxalic acid | 90.04 | 189 (dec) | 2 | Carboxilic acid | 2 | 2 | | 1.27, 4.27 |
| Palmitic acid | 256.43 | 63-64 | 1 | Carboxylic acid | 1 | 1 | $CH_3(CH_2)_{14}COOH$ | 4.9 |
| Pamoic | 388.38 | 280 (dec) | 2 | Carboxylic acid, phenol | 2 | 4 | | 2.51, 3.1 |
| Phenylalanine | 165.19 | 283 (dec.) | 1 | Amine, COOH | 1 | 3 | | ~2, ~9 |
| Piperazine | 86.14 | 106 | 1 | NH | 0 | 2 | | 9.82(B) |
| Procaine | 236.31 | 61 | 1 | Amine, C=O | 2 | 2 | | 8.9(B) |
| Proline | 115.13 | 220-222 (dec.) | 1 | COOH, NH | 1 | 2 | | 1.99, 10.6 |
| p-Toluenesulfonic acid | 172.2 | 106-107 | 2 | Sulfonic acid | 2 | 1 | | −1.34 |

TABLE I-continued

| Co-Crystal Former | MW (g/mol) | MP (° C.) | Class | Functionality | # acceptors | # donors | Molecular Structure | pKa Values |
|---|---|---|---|---|---|---|---|---|
| Pyridoxamine | 168 | 193-194 | 2 | OH, Amine, Pyridine | 3 | 4 | 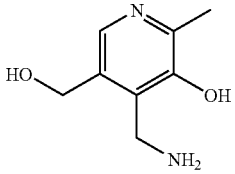 | ~9 |
| Pyridoxine | 170 | 160 | 2 | Alcohol, Pyridine | 3 | 3 | 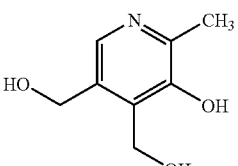 | ~9 |
| Pyroglutamic acid | 129.12 | 162 | 2 | Carboxylic acid, Lactam | 2 | 2 | 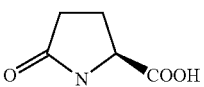 | 3.32 |
| Quercetin | 302.24 | 314 dec. | 1 | Phenol, ether ketone | 2 | 5 | 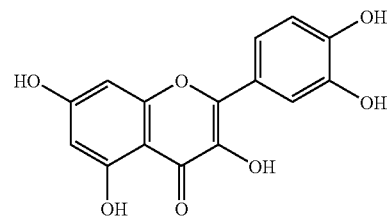 | |
| Resveratrol | 228.24 | 253-255 | 1 | Phenol | 0 | 3 | 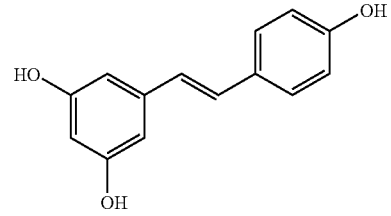 | |
| Saccharin | 183.19 | 228-230 | 1 | Amide, C=O, S=O, N—H | 3 | 1 | 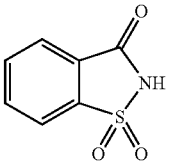 | 2 |
| Salicylic acid, 4-amino | 153.14 | 150-151 | 3 | COOH, OH, Analine | 1 | 4 | 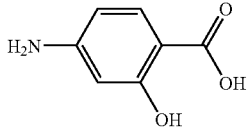 | 3.25, 10, 3.5(B) |
| Salicylic acid | 138.12 | 159 | 3 | COOH, OH | 2 | 2 | 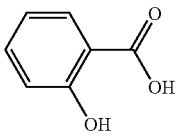 | 2.98, 13.82 |
| Sebacic acid | 202.25 | 134.5 | 1 | Carboxylic acid | 2 | 2 | HOOC(CH$_2$)$_8$COOH | 4.59, 5.59 |

TABLE I-continued

| Co-Crystal Former | MW (g/mol) | MP (° C.) | Class | Functionality | # acceptors | # donors | Molecular Strucutre | pKa Values |
|---|---|---|---|---|---|---|---|---|
| Serine | 105.09 | 228 (dec.) | 1 | Carboxylic acid, amine, OH | 2 | 3 | 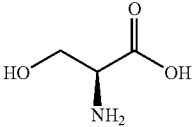 | 2.21, 9.15 |
| Stearic acid | 284.47 | 70-71 | 1 | Carboxylic acid | 1 | 1 | CH$_3$(CH$_2$)$_{16}$COOH | 4.9 |
| Succinic acid | 118.09 | 185-187 | 1 | Carboxylic acid | 2 | 2 | 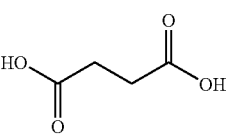 | 4.21, 5.64 |
| Tartaric acid | 150.09 | 205-206 | 1 | Carboxylic acid | 4 | 4 | 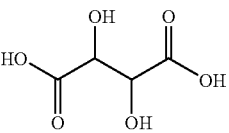 | 3.02, 4.36 |
| Threonine | 119.12 | 255-257 (dec.) | 1 | Amine, COOH, OH | 2 | 4 | 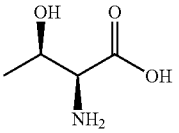 | 2.15, 9.12 |
| TRIS | 121.13 | 171-172 | 2 | Amine, OH | 3 | 5 | 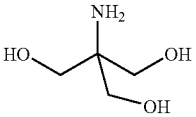 | 5.91, 8.3 |
| Tryptophan | 204.23 | 289 (dec.) | 1 | Amine, COOH, Indole | 1 | 4 | 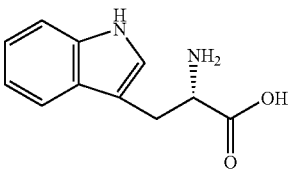 | 2.38, 9.39 |
| Tyrosine | 181.19 | 342-344 | 1 | Amine, COOH, OH | 2 | 3 | 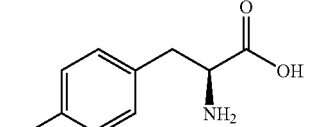 | 2.2, 9.11, 10.07 |
| Urea | 60.06 | Dec. | 1 | C=O, NH2 | 1 | 4 | 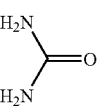 | ~8 |
| Valine | 117.15 | 315 | 1 | Amine, COOH | 1 | 3 | 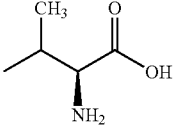 | ~4.5, ~9 |

TABLE I-continued

| Co-Crystal Former | MW (g/mol) | MP (° C.) | Class | Functionality | # acceptors | # donors | Molecular Strucutre | pKa Values |
|---|---|---|---|---|---|---|---|---|
| Vitamin K5 | 209.68 | 280-282 (dec.) | 3 | Amine, OH | 1 | 3 | (naphthalene with OH, CH₃, NH₂ substituents) | ~9 |
| Xylitol | 152.15 | 93-95 (I) | 2 | OH | 5 | 5 | HO–CH₂–CH(OH)–CH(OH)–CH(OH)–CH₂–OH | ~9 |

TABLE II

| Co-crystal Former | Co-crystal Former Functional Group | Interacting Group | | | | | | | |
|---|---|---|---|---|---|---|---|---|---|
| 1,5-Napthalene-disulfonic acid | Sulfonic Acid | pyridine | ketone | aldehyde | ether | ester | amide | Carboxylic Acid | amine |
| 1-Hydroxy-2-naphthoic acid | Carboxylic Acid | alcohol | ketone | thiol | amide | amine | analine | phenol | phosphate |
| 1-Hydroxy-2-naphthoic acid | alcohol | alcohol | ketone | thiol | amide | amine | analine | phenol | phosphate |
| 4-Aminobenzoic Acid | Amine | alcohol | ketone | thiol | amide | amine | analine | phenol | phosphate |
| 4-Aminobenzoic Acid | Carboxylic Acid | alcohol | ketone | thiol | amide | amine | analine | phenol | phosphate |
| 4-aminopyridine | Amine | alcohol | ketone | thiol | amide | amine | analine | phenol | phosphate |
| 4-aminopyridine | Pyridine | *alcohol | pyridinium | * | *amide | nitro | *amine | *Carboxylic Acid | *sulfonamide |
| 4-Chlorobenzene-Sulfonic Acid | Sulfonic Acid | pyridine | ketone | aldehyde | ether | ester | amide | Carboxylic Acid | amine |
| 4-ethoxyphenyl Urea | Amide | alcohol | ketone | thiol | amide | amine | analine | phenol | phosphate |
| 4-ethoxyphenyl Urea | Amine | alcohol | ketone | thiol | amide | amine | analine | phenol | phosphate |
| 7-oxo-DHEA | alcohol | alcohol | ketone | thiol | amide | amine | analine | phenol | phosphate |
| 7-oxo-DHEA | Ketone | alcohol | | thiol | amide | amine | analine | phenol | phosphate |
| Acesulfame | Sulfone | pyridine | ketone | aldehyde | ether | ester | amide | carboxilic acid | amine |
| Acesulfame | Amide | alcohol | ketone | thiol | amide | amine | analine | phenol | phosphate |
| Acetohydroxamic Acid | Amide | alcohol | ketone | thiol | amide | amine | analine | phenol | phosphate |
| Acetohydroxamic Acid | Amine | alcohol | ketone | thiol | amide | amine | analine | phenol | phosphate |
| Acetohydroxamic Acid | Alcohol | alcohol | ketone | thiol | amide | amine | analine | phenol | phosphate |
| Adenine | Amine | alcohol | ketone | thiol | amide | amine | analine | phenol | phosphate |
| Adenine | N | *alcohol | pyridinium | * | *amide | nitro | *amine | *carboxilic acid | *sulfonamide |
| Adipic acid | Carboxylic Acid | alcohol | ketone | thiol | amide | amine | analine | phenol | phosphate |
| Alanine | Amine | alcohol | ketone | thiol | amide | amine | analine | phenol | phosphate |
| Alanine | Carboxylic Acid | alcohol | ketone | thiol | amide | amine | analine | phenol | phosphate |
| Allopurinaol | Alcohol | alcohol | ketone | thiol | amide | amine | analine | phenol | phosphate |
| Allopurinaol | Amine | alcohol | ketone | thiol | amide | amine | analine | phenol | phosphate |
| Arginine | Amine | alcohol | ketone | thiol | amide | amine | analine | phenol | phosphate |
| Arginine | Carboxylic Acid | alcohol | ketone | thiol | amide | amine | analine | phenol | phosphate |
| Ascorbic Acid | Ketone | alcohol | | thiol | amide | amine | analine | phenol | phosphate |
| Ascorbic Acid | Alcohol | alcohol | ketone | thiol | amide | amine | analine | phenol | phosphate |
| Ascorbic Acid | Carboxylic Acid | alcohol | ketone | thiol | amide | amine | analine | phenol | phosphate |
| Asparagine | Amine | alcohol | ketone | thiol | amide | amine | analine | phenol | phosphate |
| Asparagine | Amide | alcohol | ketone | thiol | amide | amine | analine | phenol | phosphate |
| Asparagine | Carboxylic Acid | alcohol | ketone | thiol | amide | amine | analine | phenol | phosphate |
| Aspartic Acid | Amine | alcohol | ketone | thiol | amide | amine | analine | phenol | phosphate |
| Aspartic Acid | Carboxylic Acid | alcohol | ketone | thiol | amide | amine | analine | phenol | phosphate |
| Benzenesulfonic Acid | Sulfonic Acid | pyridine | ketone | aldehyde | ether | ester | amide | Carboxylic Acid | amine |

| Co-crystal Former | Interacting Group | | | | | | | | |
|---|---|---|---|---|---|---|---|---|---|
| 1,5-Napthalene-disulfonic acid | metals | thioether | | sulfate | alcohol | | | | |
| 1-Hydroxy-2-naphthoic acid | sulfate | sulfone | nitrate | pyridine | carboxilic acid | metals | aldehyde | ester | ether |
| 1-Hydroxy-2-naphthoic acid | sulfate | sulfone | nitrate | pyridine | carboxilic acid | metals | aldehyde | ester | ether |
| 4-Aminobenzoic Acid | sulfate | sulfone | nitrate | pyridine | | carboxilic acid | metals | aldehyde | ester |
| 4-Aminobenzoic Acid | sulfate | sulfone | nitrate | pyridine | | Carboxylic Acid | metals | aldehyde | ester |
| 4-aminopyridine | sulfate | sulfone | nitrate | pyridine | | carboxilic acid | metals | aldehyde | ester |

TABLE II-continued

| | | | | | | | | | |
|---|---|---|---|---|---|---|---|---|---|
| 4-aminopyridine | *ketone | ether | triazole | | ammonium | oxime | *chlorine | | thiol |
| 4-Chlorobenzene-Sulfonic Acid | metals | thioether | | sulfate | alcohol | | | | |
| 4-ethoxyphenyl Urea | sulfate | sulfone | nitrate | pyridine | | Carboxylic Acid | metals | aldehyde | ester |
| 4-ethoxyphenyl Urea | sulfate | sulfone | nitrate | pyridine | | carboxilic acid | metals | aldehyde | ester |
| 7-oxo-DHEA | sulfate | sulfone | nitrate | pyridine | carboxilic acid | metals | aldehyde | ester | ether |
| 7-oxo-DHEA | sulfate | sulfone | nitrate | pyridine | | Carboxylic Acid | metals | aldehyde | ester |
| Acesulfame | metals | thioether | | sulfate | alcohol | | | | |
| Acesulfame | sulfate | sulfone | nitrate | pyridine | | Carboxylic Acid | metals | aldehyde | ester |
| Acetohydroxamic Acid | sulfate | sulfone | nitrate | pyridine | | carboxilic acid | metals | aldehyde | ester |
| Acetohydroxamic Acid | sulfate | sulfone | nitrate | pyridine | | carboxilic acid | metals | aldehyde | ester |
| Acetohydroxamic Acid | sulfate | sulfone | nitrate | pyridine | | Carboxylic Acid | metals | aldehyde | ester |
| Adenine | sulfate | sulfone | nitrate | pyridine | | carboxilic acid | metals | aldehyde | ester |
| Adenine | *ketone | ether | triazole | | ammonium | oxime | *chlorine | | thiol |
| Adipic acid | sulfate | sulfone | nitrate | pyridine | | carboxilic acid | metals | aldehyde | ester |
| Alanine | sulfate | sulfone | nitrate | pyridine | | carboxilic acid | metals | aldehyde | ester |
| Alanine | sulfate | sulfone | nitrate | pyridine | | carboxilic acid | metals | aldehyde | ester |
| Allopurinaol | sulfate | sulfone | nitrate | pyridine | | Carboxylic Acid | metals | aldehyde | ester |
| Allopurinaol | sulfate | sulfone | nitrate | pyridine | | carboxilic acid | metals | aldehyde | ester |
| Arginine | sulfate | sulfone | nitrate | pyridine | | carboxilic acid | metals | aldehyde | ester |
| Arginine | sulfate | sulfone | nitrate | pyridine | | carboxilic acid | metals | aldehyde | ester |
| Ascorbic Acid | sulfate | sulfone | nitrate | pyridine | | Carboxylic Acid | metals | aldehyde | ester |
| Ascorbic Acid | sulfate | sulfone | nitrate | pyridine | | Carboxylic Acid | metals | aldehyde | ester |
| Ascorbic Acid | sulfate | sulfone | nitrate | pyridine | | carboxilic acid | metals | aldehyde | ester |
| Asparagine | sulfate | sulfone | nitrate | pyridine | | carboxilic acid | metals | aldehyde | ester |
| Asparagine | sulfate | sulfone | nitrate | pyridine | | Carboxylic Acid | metals | aldehyde | ester |
| Asparagine | sulfate | sulfone | nitrate | pyridine | | carboxilic acid | metals | aldehyde | ester |
| Aspartic Acid | sulfate | sulfone | nitrate | pyridine | | carboxilic acid | metals | aldehyde | ester |
| Aspartic Acid | sulfate | sulfone | nitrate | pyridine | | carboxilic acid | metals | aldehyde | ester |
| Benzenesulfonic Acid | metals | thioether | | sulfate | alcohol | | | | |

| Co-crystal Former | Interacting Group | | | | | | | |
|---|---|---|---|---|---|---|---|---|
| 1,5-Napthalene-disulfonic Acid | | | | | | | | |
| 1-Hydroxy-2-naphthoic acid | cyano | | furan | bromine | chlorine | s-heterocyclic | pyridine | cyano |
| 1-Hydroxy-2-naphthoic acid | cyano | | furan | bromine | chlorine | s-heterocyclic | pyridine | cyano |
| 4-Aminobenzoic Acid | ether | cyano | | furan | bromine | chlorine | s-heterocyclic | pyridine |
| 4-Aminobenzoic acid | ether | cyano | | furan | bromine | chlorine | s-heterocyclic | pyridine |
| 4-aminopyridine | ether | cyano | | furan | bromine | chlorine | s-heterocyclic | pyridine |
| 4-aminopyridine | n-heterocyclic ring | thionedisulfide | pyrrolidindione | iodine | hydrazone | thiocyanate | *bromine | |
| 4-Chlorobenzene-Sulfonic Acid | | | | | | | | |
| 4-ethoxyphenyl Urea | ether | cyano | | furan | bromine | chlorine | s-heterocyclic | pyridine |
| 4-ethoxyphenyl Urea | ether | cyano | | furan | bromine | chlorine | s-heterocyclic | pyridine |
| 7-oxo-DHEA | cyano | | furan | bromine | chlorine | s-heterocyclic | pyridine | cyano |
| 7-oxo-DHEA | ether | cyano | | furan | bromine | chlorine | s-heterocyclic | pyridine |
| Acesulfame | | | | | | | | |
| Acesulfame | ether | cyano | | furan | bromine | chlorine | s-heterocyclic | pyridine |
| Acetohydroxamic Acid | ether | cyano | | furan | bromine | chlorine | s-heterocyclic | pyridine |
| Acetohydroxamic Acid | ether | cyano | | furan | bromine | chlorine | s-heterocyclic | pyridine |
| Acetohydroxamic Acid | ether | cyano | | furan | bromine | chlorine | s-heterocyclic | pyridine |
| Adenine | ether | cyano | | furan | bromine | chlorine | s-heterocyclic | pyridine |
| Adenine | n-heterocyclic ring | thionedisulfide | pyrrolidindione | iodine | hydrazone | thiocyanate | *bromine | |
| Adipic acid | ether | cyano | | furan | bromine | chlorine | s-heterocyclic | pyridine |
| Alanine | ether | cyano | | furan | bromine | chlorine | s-heterocyclic | pyridine |
| Alanine | ether | cyano | | furan | bromine | chlorine | s-heterocyclic | pyridine |
| Allopurinaol | ether | cyano | | furan | bromine | chlorine | s-heterocyclic | pyridine |
| Allopurinaol | ether | cyano | | furan | bromine | chlorine | s-heterocyclic | pyridine |
| Arginine | ether | cyano | | furan | bromine | chlorine | s-heterocyclic | pyridine |
| Arginine | ether | cyano | | furan | bromine | chlorine | s-heterocyclic | pyridine |
| Ascorbic Acid | ether | cyano | | furan | bromine | chlorine | s-heterocyclic | pyridine |
| Ascorbic Acid | ether | cyano | | furan | bromine | chlorine | s-heterocyclic | pyridine |
| Ascorbic Acid | ether | cyano | | furan | bromine | chlorine | s-heterocyclic | pyridine |
| Asparagine | ether | cyano | | furan | bromine | chlorine | s-heterocyclic | pyridine |
| Asparagine | ether | cyano | | furan | bromine | chlorine | s-heterocyclic | pyridine |
| Asparagine | ether | cyano | | furan | bromine | chlorine | s-heterocyclic | pyridine |
| Aspartic acid | ether | cyano | | furan | bromine | chlorine | s-heterocyclic | pyridine |
| Aspartic acid | ether | cyano | | furan | bromine | chlorine | s-heterocyclic | pyridine |
| Benzenesulfonic Acid | | | | | | | | |

| Co-crystal Former | Interacting Group | | | | | |
|---|---|---|---|---|---|---|
| 1,5-Napthalene-disulfonic Acid | | | | | | |
| 1-Hydroxy-2-naphthoic acid | n-heterocyclic | ketone | phosphate ester | | fluorine | carbamate | imidazole |
| 1-Hydroxy-2-naphthoic acid | n-heterocyclic | ketone | phosphate ester | | fluorine | carbamate | imidazole |
| 4-Aminobenzoic Acid | cyano | n-heterocyclic | ketone | phosphate ester | | fluorine | carbamate |
| 4-Aminobenzoic Acid | cyano | n-heterocyclic | ketone | phosphate ester | | fluorine | carbamate |
| 4-aminopyridine | cyano | n-heterocyclic | ketone | phosphate ester | | fluorine | carbamate |

TABLE II-continued

| | | | | | | | |
|---|---|---|---|---|---|---|---|
| 4-aminopyridine | hydroxamic acid | cyano | carboxamide | *sulfonic acid | *phosphoric acid | N-oxide | ester |
| 4-Chlorobenzene-Sulfonic Acid | | | | | | | |
| 4-ethoxyphenyl Urea | cyano | n-heterocyclic | ketone | phosphate ester | | fluorine | carbamate |
| 4-ethoxyphenyl Urea | cyano | n-heterocyclic | ketone | phosphate ester | | fluorine | carbamate |
| 7-oxo-DHEA | n-heterocyclic | ketone | phosphate ester | | fluorine | carbamate | imidazole |
| 7-oxo-DHEA | cyano | n-heterocyclic | ketone | phosphate ester | | fluorine | carbamate |
| Acesulfame | | | | | | | |
| Acesulfame | cyano | n-heterocyclic | ketone | phosphate ester | | fluorine | carbamate |
| Acetohydroxamic Acid | cyano | n-heterocyclic | ketone | phosphate ester | | fluorine | carbamate |
| Acetohydroxamic Acid | cyano | n-heterocyclic | ketone | phosphate ester | | fluorine | carbamate |
| Acetohydroxamic Acid | cyano | n-heterocyclic | ketone | phosphate ester | | fluorine | carbamate |
| Adenine | cyano | n-heterocyclic | ketone | phosphate ester | | fluorine | carbamate |
| Adenine | hydroxamic acid | cyano | carboxamide | *sulfonic acid | *phosphoric acid | N-oxide | ester |
| Adipic acid | cyano | n-heterocyclic | ketone | phosphate ester | | fluorine | carbamate |
| Alanine | cyano | n-heterocyclic | ketone | phosphate ester | | fluorine | carbamate |
| Alanine | cyano | n-heterocyclic | ketone | phosphate ester | | fluorine | carbamate |
| Allopurinaol | cyano | n-heterocyclic | ketone | phosphate ester | | fluorine | carbamate |
| Allopurinaol | cyano | n-heterocyclic | ketone | phosphate ester | | fluorine | carbamate |
| Arginine | cyano | n-heterocyclic | ketone | phosphate ester | | fluorine | carbamate |
| Arginine | cyano | n-heterocyclic | ketone | phosphate ester | | fluorine | carbamate |
| Ascorbic Acid | cyano | n-heterocyclic | ketone | phosphate ester | | fluorine | carbamate |
| Ascorbic Acid | cyano | n-heterocyclic | ketone | phosphate ester | | fluorine | carbamate |
| Ascorbic Acid | cyano | n-heterocyclic | ketone | phosphate ester | | fluorine | carbamate |
| Asparagine | cyano | n-heterocyclic | ketone | phosphate ester | | fluorine | carbamate |
| Asparagine | cyano | n-heterocyclic | ketone | phosphate ester | | fluorine | carbamate |
| Asparagine | cyano | n-heterocyclic | ketone | phosphate ester | | fluorine | carbamate |
| Aspartic Acid | cyano | n-heterocyclic | ketone | phosphate ester | | fluorine | carbamate |
| Aspartic Acid | cyano | n-heterocyclic | ketone | phosphate ester | | fluorine | carbamate |
| Benzenesulfonic Acid | | | | | | | |

| Co-crystal Former | Interacting Group | | | | | | | | |
|---|---|---|---|---|---|---|---|---|---|
| 1,5-Napthalene-disulfonic Acid | | | | | | | | | |
| 1-Hydroxy-2-naphthoic acid | BF4 | | | | | | | | |
| 1-Hydroxy-2-naphthoic acid | BF4 | | | | | | | | |
| 4-Aminobenzoic Acid | imidazole | BF4 | | N—SO2 | | thiourea | iodine | | |
| 4-Aminobenzoic Acid | imidazole | BF4 | | N—SO2 | | thiourea | iodine | | |
| 4-aminopyridine | imidazole | BF4 | | N—SO2 | | thiourea | iodine | | |
| 4-aminopyridine | ether | fluorine | acetate | thione | dithiadiazocyclopentadienyl | | | | |
| 4-Chlorobenzene-Sulfonic Acid | imidazole | BF4 | | N—SO2 | | thiourea | iodine | epoxide | peroxide |
| 4-ethoxyphenyl Urea | imidazole | BF4 | | N—SO2 | | thiourea | iodine | | |
| 4-ethoxyphenyl Urea | imidazole | BF4 | | N—SO2 | | thiourea | iodine | | |
| 7-oxo-DHEA | BF4 | | | | | | | | |
| 7-oxo-DHEA | imidazole | BF4 | | N—SO2 | | thiourea | iodine | | |
| Acesulfame | | | | | | | | | |
| Acesulfame | imidazole | BF4 | | N—SO2 | | thiourea | iodine | epoxide | peroxide |
| Acetohydroxamic Acid | imidazole | BF4 | | N—SO2 | | thiourea | iodine | epoxide | peroxide |
| Acetohydroxamic Acid | imidazole | BF4 | | N—SO2 | | thiourea | iodine | | |
| Acetohydroxamic Acid | imidazole | BF4 | | N—SO2 | | thiourea | iodine | epoxide | |
| Adenine | imidazole | BF4 | | N—SO2 | | thiourea | iodine | | |
| Adenine | ether | fluorine | acetate | thione | dithiadiazocyclopentadienyl | | | | |
| Adipic acid | imidazole | BF4 | | N—SO2 | | thiourea | iodine | | |
| Alanine | imidazole | BF4 | | N—SO2 | | thiourea | iodine | | |
| Alanine | imidazole | BF4 | | N—SO2 | | thiourea | iodine | | |
| Allopurinaol | imidazole | BF4 | | N—SO2 | | thiourea | iodine | epoxide | |
| Allopurinaol | imidazole | BF4 | | N—SO2 | | thiourea | iodine | | |
| Arginine | imidazole | BF4 | | N—SO2 | | thiourea | iodine | | |
| Arginine | imidazole | BF4 | | N—SO2 | | thiourea | iodine | | |
| Ascorbic Acid | imidazole | BF4 | | N—SO2 | | thiourea | iodine | | |
| Ascorbic Acid | imidazole | BF4 | | N—SO2 | | thiourea | iodine | epoxide | |
| Ascorbic Acid | imidazole | BF4 | | N—SO2 | | thiourea | iodine | | |
| Asparagine | imidazole | BF4 | | N—SO2 | | thiourea | iodine | | |
| Asparagine | imidazole | BF4 | | N—SO2 | | thiourea | iodine | epoxide | peroxide |
| Asparagine | imidazole | BF4 | | N—SO2 | | thiourea | iodine | | |
| Aspartic acid | imidazole | BF4 | | N—SO2 | | thiourea | iodine | | |
| Aspartic acid | imidazole | BF4 | | N—SO2 | | thiourea | iodine | | |
| Benzenesulfonic Acid | | | | | | | | | |

| Co-crystal Former | Co-crystal Former Functional Group | Interacting Group | | | | | | | |
|---|---|---|---|---|---|---|---|---|---|
| Benzoic Acid | Carboxylic Acid | alcohol | ketone | thiol | amide | amine | analine | phenol | phosphate |
| Caffeine | Ketone | alcohol | | thiol | amide | amine | analine | phenol | phosphate |
| Camphoric acid | Carboxylic Acid | alcohol | ketone | thiol | amide | amine | analine | phenol | phosphate |
| Capric acid | Carboxylic Acid | alcohol | ketone | thiol | amide | amine | analine | phenol | phosphate |
| Genistein | Ketone | alcohol | | thiol | amide | amine | analine | phenol | phosphate |
| Genistein | Phenol | amine | amide | sulfoxide | n | pyridine | cyano | aldehyde | |
| Genistein | Ether | aromatic-N | amide | amine | aromatic_s | Sp2 amine | sulfoxide | chlorate | chlorine |
| Cinnamic acid | Carboxylic Acid | alcohol | ketone | thiol | amide | amine | analine | phenol | phosphate |

TABLE II-continued

| | | | | | | | | | |
|---|---|---|---|---|---|---|---|---|---|
| Citric Acid | Alcohol | alcohol | ketone | thiol | amide | amine | analine | phenol | phosphate |
| Citric Acid | Carboxylic Acid | alcohol | ketone | thiol | amide | amine | analine | phenol | phosphate |
| Clemizole | Pyrrolidine | *alcohol | pyridinium | * | *amide | nitro | *amine | *carboxilic acid | *sulfonamide |
| Cyclamic Acid | Amine | alcohol | ketone | thiol | amide | amine | analine | phenol | phosphate |
| Cyclamic Acid | Sulfonic Acid | pyridine | ketone | aldehyde | ether | ester | amide | Carboxylic Acid | amine |
| Cysteine | Amine | alcohol | ketone | thiol | amide | amine | analine | phenol | phosphate |
| Cysteine | Carboxylic Acid | alcohol | ketone | thiol | amide | amine | analine | phenol | phosphate |
| Cysteine | Thiol | carboxylic acid | sodium | aldehyde | ketone | —N | cadmium | | arsenic |
| Dimethylglycine | Carboxylic Acid | alcohol | ketone | thiol | amide | amine | analine | phenol | phosphate |
| Dimethylglycine | Amine | alcohol | ketone | thiol | amide | amine | analine | phenol | phosphate |
| D-ribose | Ether | aromatic-N | amide | amine | aromatic_s | Sp2 amine | sulfoxide | chlorate | chlorine |
| D-ribose | Alcohol | alcohol | ketone | thiol | amide | amine | analine | phenol | phosphate |
| Fumaric Acid | Carboxylic Acid | alcohol | ketone | thiol | amide | amine | analine | phenol | phosphate |
| Galactaric acid | Carboxylic Acid | alcohol | ketone | thiol | amide | amine | analine | phenol | phosphate |
| Galactaric acid | alcohol | alcohol | ketone | thiol | amide | amine | analine | phenol | phosphate |
| Chrysin | Ketone | alcohol | | thiol | amide | amine | analine | phenol | phosphate |
| Chrysin | Phenol | amine | amide | sulfoxide | n | pyridine | cyano | aldehyde | |
| Chrysin | Ether | aromatic-N | amide | amine | aromatic_s | Sp2 amine | sulfoxide | chlorate | chlorine |
| Gentisic acid | Carboxylic Acid | alcohol | ketone | thiol | amide | amine | analine | phenol | phosphate |
| Gentisic acid | Phenol | amine | amide | sulfoxide | n | pyridine | cyano | aldehyde | |
| Glucamine, N-methyl | alcohol | alcohol | ketone | thiol | amide | amine | analine | phenol | phosphate |
| Glucamine, N-methyl | Amine | alcohol | ketone | thiol | amide | amine | analine | phenol | phosphate |
| Gluconic Acid | Alcohol | alcohol | ketone | thiol | amide | amine | analine | phenol | phosphate |
| Gluconic Acid | Carboxylic Acid | alcohol | ketone | thiol | amide | amine | analine | phenol | phosphate |
| Glucosamine | alcohol | alcohol | ketone | thiol | amide | amine | analine | phenol | phosphate |
| Glucuronic acid | Carboxylic Acid | alcohol | ketone | thiol | amide | amine | analine | phenol | phosphate |
| Glucuronic acid | alcohol | alcohol | ketone | thiol | amide | amine | analine | phenol | phosphate |
| Glucuronic acid | Aldehyde | alcohol | ketone | thiol | amide | amine | analine | phenol | phosphate |
| Glutamic Acid | Amine | alcohol | ketone | thiol | amide | amine | analine | phenol | phosphate |
| Glutamic Acid | Carboxylic Acid | alcohol | ketone | thiol | amide | amine | analine | phenol | phosphate |

| Co-crystal Former | | | | Interacting Group | | | | | |
|---|---|---|---|---|---|---|---|---|---|
| Benzoic Acid | sulfate | sulfone | nitrate | pyridine | | carboxilic acid | metals | aldehyde | ester | ether |
| Caffeine | sulfate | sulfone | nitrate | pyridine | | Carboxylic Acid | metals | aldehyde | ester | ether |
| Camphoric acid | sulfate | sulfone | nitrate | pyridine | | carboxilic acid | metals | aldehyde | ester | ether |
| Capric acid | sulfate | sulfone | nitrate | pyridine | | carboxilic acid | metals | aldehyde | ester | ether |
| Genistein | sulfate | sulfone | nitrate | pyridine | | Carboxylic Acid | metals | aldehyde | ester | ether |
| Genistein | alchohol | | ester | ether | n-oxide | chlorine | fluorine | bromine | iodine | ketone |
| Genistein | | cyano | ester | amine | nitro | nitrate | bromine | aldehyde | ketone | peroxide |
| Cinnamic acid | sulfate | sulfone | nitrate | pyridine | | carboxilic acid | metals | aldehyde | ester | ether |
| Citric Acid | sulfate | sulfone | nitrate | pyridine | | Carboxylic Acid | metals | aldehyde | ester | ether |
| Citric Acid | sulfate | sulfone | nitrate | pyridine | | carboxilic acid | metals | aldehyde | ester | ether |
| Clemizole | *ketone | ether | triazole | | ammonium | oxime | *chlorine | | thiol | n-heterocyclic ring |
| Cyclamic Acid | sulfate | sulfone | nitrate | pyridine | | carboxilic acid | metals | aldehyde | ester | ether |
| Cyclamic Acid | metals | thioether | | sulfate | alcohol | | | | | |
| Cysteine | sulfate | sulfone | nitrate | pyridine | | carboxilic acid | metals | aldehyde | ester | ether |
| Cysteine | sulfate | sulfone | nitrate | pyridine | | carboxilic acid | metals | aldehyde | ester | ether |
| Cysteine | chlorine | alcohol | potassium | Ru | | Rb | Sb | | | |
| Dimethylglycine | sulfate | sulfone | nitrate | pyridine | | carboxilic acid | metals | aldehyde | ester | ether |
| Dimethylglycine | sulfate | sulfone | nitrate | pyridine | | carboxilic acid | metals | aldehyde | ester | ether |
| D-ribose | | cyano | ester | amine | nitro | nitrate | bromine | aldehyde | ketone | peroxide |
| D-ribose | sulfate | sulfone | nitrate | pyridine | | Carboxylic Acid | metals | aldehyde | ester | ether |
| Fumaric Acid | sulfate | sulfone | nitrate | pyridine | | carboxilic acid | metals | aldehyde | ester | ether |
| Galactaric acid | sulfate | sulfone | nitrate | pyridine | | carboxilic acid | metals | aldehyde | ester | ether |
| Galactaric acid | sulfate | sulfone | nitrate | pyridine | carboxilic acid | metals | aldehyde | ester | ether | cyano |
| Chrysin | sulfate | sulfone | nitrate | pyridine | | Carboxylic Acid | metals | aldehyde | ester | ether |
| Chrysin | alchohol | | ester | ether | n-oxide | chlorine | fluorine | bromine | iodine | ketone |
| Chrysin | | cyano | ester | amine | nitro | nitrate | bromine | aldehyde | ketone | peroxide |
| Gentisic acid | sulfate | sulfone | nitrate | pyridine | | carboxilic acid | metals | aldehyde | ester | ether |
| Gentisic acid | alchohol | | ester | ether | n-oxide | chlorine | fluorine | bromine | iodine | ketone |
| Glucamine, N-methyl | sulfate | sulfone | nitrate | pyridine | carboxilic acid | metals | aldehyde | ester | ether | cyano |
| Glucamine, N-methyl | sulfate | sulfone | nitrate | pyridine | | carboxilic acid | metals | aldehyde | ester | ether |
| Gluconic Acid | sulfate | sulfone | nitrate | pyridine | | Carboxylic Acid | metals | aldehyde | ester | ether |
| Gluconic Acid | sulfate | sulfone | nitrate | pyridine | | carboxilic acid | metals | aldehyde | ester | ether |
| Glucosamine | sulfate | sulfone | nitrate | pyridine | | Carboxylic Acid | metals | aldehyde | ester | ether |
| Glucuronic acid | sulfate | sulfone | nitrate | pyridine | | carboxilic acid | metals | aldehyde | ester | ether |
| Glucuronic acid | sulfate | sulfone | nitrate | pyridine | carboxilic acid | metals | aldehyde | ester | ether | cyano |
| Glucuronic acid | sulfate | sulfone | nitrate | pyridine | aromatic | carboxilic acid | metals | aldehyde | ester | ether |

TABLE II-continued

| | | | | | | | | | |
|---|---|---|---|---|---|---|---|---|---|
| Glutamic Acid | sulfate | sulfone | nitrate | pyridine | carboxilic acid | metals | aldehyde | ester | ether |
| Glutamic Acid | sulfate | sulfone | nitrate | pyridine | carboxilic acid | metals | aldehyde | ester | ether |

| Co-crystal Former | Interacting Group | | | | | | | | |
|---|---|---|---|---|---|---|---|---|---|
| Benzoic Acid | cyano | | furan | bromine | chlorine | s-heterocyclic | pyridine | cyano | |
| Caffeine | cyano | | furan | bromine | chlorine | s-heterocyclic | pyridine | cyano | |
| Camphoric acid | cyano | | furan | bromine | chlorine | s-heterocyclic | pyridine | cyano | |
| Capric acid | cyano | | furan | bromine | chlorine | s-heterocyclic | pyridine | cyano | |
| Genistein | cyano | | furan | bromine | chlorine | s-heterocyclic | pyridine | cyano | |
| Genistein | sulfonic acid | sulfate | phosphate | phosphonic acid | carboxylic acid | nitro | | sulfone | analine |
| Genistein | epoxide | | | heterocyclic-S | iodine | ester | | ether | carboxylic acid |
| Cinnamic acid | cyano | | furan | bromine | chlorine | s-heterocyclic | pyridine | cyano | |
| Citric Acid | cyano | | furan | bromine | chlorine | s-heterocyclic | pyridine | cyano | |
| Citric Acid | cyano | | furan | bromine | chlorine | s-heterocyclic | pyridine | cyano | |
| Clemizole | thionedisulfide | pyrrolidindione | iodine | hydrazone | thiocyanate | *bromine | | | hydroxamic acid |
| Cyclamic Acid | cyano | | furan | bromine | chlorine | s-heterocyclic | pyridine | cyano | |
| Cyclamic Acid | | | | | | | | | |
| Cysteine | cyano | | furan | bromine | chlorine | s-heterocyclic | pyridine | cyano | |
| Cysteine | cyano | | furan | bromine | chlorine | s-heterocyclic | pyridine | cyano | |
| Cysteine | | | | | | | | | |
| Dimethylglycine | cyano | | furan | bromine | chlorine | s-heterocyclic | pyridine | cyano | |
| Dimethylglycine | cyano | | furan | bromine | chlorine | s-heterocyclic | pyridine | cyano | |
| D-ribose | epoxide | | | heterocyclic-S | iodine | ester | | ether | carboxylic acid |
| D-ribose | cyano | | furan | bromine | chlorine | s-heterocyclic | pyridine | cyano | |
| Fumaric Acid | cyano | | furan | bromine | chlorine | s-heterocyclic | pyridine | cyano | |
| Galactaric acid | cyano | | furan | bromine | chlorine | s-heterocyclic | pyridine | cyano | |
| Galactaric acid | | furan | bromine | chlorine | s-heterocyclic | pyridine | cyano | n-heterocyclic | |
| Chrysin | cyano | | furan | bromine | chlorine | s-heterocyclic | pyridine | cyano | |
| Chrysin | sulfonic acid | sulfate | phosphate | phosphonic acid | carboxylic acid | nitro | | sulfone | analine |
| Chrysin | epoxide | | | heterocyclic-S | iodine | ester | | ether | carboxylic acid |
| Gentisic acid | cyano | | furan | bromine | chlorine | s-heterocyclic | pyridine | cyano | |
| Gentisic acid | sulfonic acid | sulfate | phosphate | phosphonic acid | carboxylic acid | nitro | | sulfone | analine |
| Glucamine, N-methyl | | furan | bromine | chlorine | s-heterocyclic | pyridine | cyano | n-heterocyclic | |
| Glucamine, N-methyl | cyano | | furan | bromine | chlorine | s-heterocyclic | pyridine | cyano | |
| Gluconic Acid | cyano | | furan | bromine | chlorine | s-heterocyclic | pyridine | cyano | |
| Gluconic Acid | cyano | | furan | bromine | chlorine | s-heterocyclic | pyridine | cyano | |
| Glucosamine | cyano | | furan | bromine | chlorine | s-heterocyclic | pyridine | cyano | |
| Glucuronic acid | cyano | | furan | bromine | chlorine | s-heterocyclic | pyridine | cyano | |
| Glucuronic acid | | furan | bromine | chlorine | s-heterocyclic | pyridine | cyano | n-heterocyclic | |
| Glucuronic acid | cyano | | furan | bromine | chlorine | s-heterocyclic | pyridine | cyano | |
| Glutamic Acid | cyano | | furan | bromine | chlorine | s-heterocyclic | pyridine | cyano | |
| Glutamic Acid | cyano | | furan | bromine | chlorine | s-heterocyclic | pyridine | cyano | |

| Co-crystal Former | Interacting Group | | | | | | | | |
|---|---|---|---|---|---|---|---|---|---|
| Benzoic Acid | n-heterocyclic | ketone | phosphate ester | | fluorine | carbamate | imidazole | BF4 | |
| Caffeine | n-heterocyclic | ketone | phosphate ester | | fluorine | carbamate | imidazole | BF4 | |
| Camphoric acid | n-heterocyclic | ketone | phosphate ester | | fluorine | carbamate | imidazole | BF4 | |
| Capric acid | n-heterocyclic | ketone | phosphate ester | | fluorine | carbamate | imidazole | BF4 | |
| Genistein | n-heterocyclic | ketone | phosphate ester | | fluorine | carbamate | imidazole | BF4 | |
| Genistein | | | | | | | | | |
| Genistein | sulfate | sulfone | | alcohol | | phospphate | cyanamide | | |
| Cinnamic acid | n-heterocyclic | ketone | phosphate ester | | fluorine | carbamate | imidazole | BF4 | |
| Citric Acid | n-heterocyclic | ketone | phosphate ester | | fluorine | carbamate | imidazole | BF4 | |
| Citric Acid | n-heterocyclic | ketone | phosphate ester | | fluorine | carbamate | imidazole | BF4 | |
| Clemizole | cyano | carboxamide | *sulfonic acid | *phosphoric acid | N-oxide | ester | ether | fluorine | acetate |
| Cyclamic Acid | n-heterocyclic | ketone | phosphate ester | | fluorine | carbamate | imidazole | BF4 | |
| Cyclamic Acid | | | | | | | | | |
| Cysteine | n-heterocyclic | ketone | phosphate ester | | fluorine | carbamate | imidazole | BF4 | |
| Cysteine | n-heterocyclic | ketone | phosphate ester | | fluorine | carbamate | imidazole | BF4 | |
| Cysteine | | | | | | | | | |
| Dimethylglycine | n-heterocyclic | ketone | phosphate ester | | fluorine | carbamate | imidazole | BF4 | |
| Dimethylglycine | n-heterocyclic | ketone | phosphate ester | | fluorine | carbamate | imidazole | BF4 | |
| D-ribose | sulfate | sulfone | | alcohol | | phospphate | cyanamide | | |
| D-ribose | n-heterocyclic | ketone | phosphate ester | | fluorine | carbamate | imidazole | BF4 | |
| Fumaric Acid | n-heterocyclic | ketone | phosphate ester | | fluorine | carbamate | imidazole | BF4 | |
| Galactaric acid | n-heterocyclic | ketone | phosphate ester | | fluorine | carbamate | imidazole | BF4 | |
| Galactaric acid | ketone | phosphate ester | | fluorine | carbamate | imidazole | BF4 | | |
| Chrysin | n-heterocyclic | ketone | phosphate ester | | fluorine | carbamate | imidazole | BF4 | |
| Chrysin | | | | | | | | | |
| Chrysin | sulfate | sulfone | | alcohol | | phospphate | cyanamide | | |
| Gentisic acid | n-heterocyclic | ketone | phosphate ester | | fluorine | carbamate | imidazole | BF4 | |
| Gentisic acid | | | | | | | | | |
| Glucamine, N-methyl | ketone | phosphate ester | | fluorine | carbamate | imidazole | BF4 | | |
| Glucamine, N-methyl | n-heterocyclic | ketone | phosphate ester | | fluorine | carbamate | imidazole | BF4 | |
| Gluconic Acid | n-heterocyclic | ketone | phosphate ester | | fluorine | carbamate | imidazole | BF4 | |
| Gluconic Acid | n-heterocyclic | ketone | phosphate ester | | fluorine | carbamate | imidazole | BF4 | |
| Glucosamine | n-heterocyclic | ketone | phosphate ester | | fluorine | carbamate | imidazole | BF4 | |

TABLE II-continued

| Co-crystal Former | | | | | | | | | |
|---|---|---|---|---|---|---|---|---|---|
| Glucuronic acid | n-heterocyclic | ketone | phosphate ester | | fluorine | carbamate | imidazole | BF4 | |
| Glucuronic acid | ketone | phosphate ester | | fluorine | carbamate | imidazole | BF4 | | |
| Glucuronic acid | n-heterocyclic | ketone | phosphate ester | | fluorine | carbamate | imidazole | BF4 | alkane |
| Glutamic Acid | n-heterocyclic | ketone | phosphate ester | | fluorine | carbamate | imidazole | BF4 | |
| Glutamic Acid | n-heterocyclic | ketone | phosphate ester | | fluorine | carbamate | imidazole | BF4 | |

| Co-crystal Former | | Interacting Group | | | |
|---|---|---|---|---|---|
| Benzoic Acid | | N—SO2 | thiourea | iodine | |
| Caffeine | | N—SO2 | thiourea | iodine | |
| Camphoric acid | | N—SO2 | thiourea | iodine | |
| Capric acid | | N—SO2 | thiourea | iodine | |
| Genistein | | N—SO2 | thiourea | iodine | |
| Genistein | | | | | |
| Genistein | | | | | |
| Cinnamic acid | | N—SO2 | thiourea | iodine | |
| Citric Acid | | N—SO2 | thiourea | iodine | epoxide |
| Citric Acid | | N—SO2 | thiourea | iodine | |
| Clemizole | thione | dithiadiazocyclopentadienyl | | | |
| Cyclamic Acid | | N—SO2 | thiourea | iodine | |
| Cyclamic Acid | | | | | |
| Cysteine | | N—SO2 | thiourea | iodine | |
| Cysteine | | N—SO2 | thiourea | iodine | |
| Cysteine | | | | | |
| Dimethylglycine | | N—SO2 | thiourea | iodine | |
| Dimethylglycine | | N—SO2 | thiourea | iodine | |
| D-ribose | | | | | |
| D-ribose | | N—SO2 | thiourea | iodine | epoxide |
| Fumaric Acid | | N—SO2 | thiourea | iodine | |
| Galactaric acid | | N—SO2 | thiourea | iodine | |
| Galactaric acid | | | | | |
| Chrysin | | N—SO2 | thiourea | iodine | |
| Chrysin | | | | | |
| Chrysin | | | | | |
| Gentisic acid | | N—SO2 | thiourea | iodine | |
| Gentisic acid | | | | | |
| Glucamine, N-methyl | | | | | |
| Glucamine, N-methyl | | N—SO2 | thiourea | iodine | |
| Gluconic Acid | | N—SO2 | thiourea | iodine | epoxide |
| Gluconic Acid | | N—SO2 | thiourea | iodine | |
| Glucosamine | | N—SO2 | thiourea | iodine | epoxide |
| Glucuronic acid | | N—SO2 | thiourea | iodine | |
| Glucuronic acid | | | | | |
| Glucuronic acid | aromatic | N—SO2 | thiourea | iodine | epoxide |
| Glutamic Acid | | N—SO2 | thiourea | iodine | |
| Glutamic Acid | | N—SO2 | thiourea | iodine | |

| Co-crystal Former | Co-crystal Former Functional Group | Interacting Group | | | | | | | | |
|---|---|---|---|---|---|---|---|---|---|---|
| Glutamine | Amine | alcohol | ketone | thiol | amide | amine | analine | phenol | phosphate | sulfate |
| Glutamine | Amide | alcohol | ketone | thiol | amide | amine | analine | phenol | phosphate | sulfate |
| Glutamine | Carboxylic Acid | alcohol | ketone | thiol | amide | amine | analine | phenol | phosphate | sulfate |
| Glutaric Acid | Carboxylic Acid | alcohol | ketone | thiol | amide | amine | analine | phenol | phosphate | sulfate |
| Glycine | Amine | alcohol | ketone | thiol | amide | amine | analine | phenol | phosphate | sulfate |
| Glycine | Carboxylic Acid | alcohol | ketone | thiol | amide | amine | analine | phenol | phosphate | sulfate |
| Glycolic Acid | Alcohol | alcohol | ketone | thiol | amide | amine | analine | phenol | phosphate | sulfate |
| Glycolic Acid | Carboxylic Acid | alcohol | ketone | thiol | amide | amine | analine | phenol | phosphate | sulfate |
| Hippuric Acid | Amide | alcohol | ketone | thiol | amide | amine | analine | phenol | phosphate | sulfate |
| Hippuric Acid | Amine | alcohol | ketone | thiol | amide | amine | analine | phenol | phosphate | sulfate |
| Hippuric Acid | Carboxylic Acid | alcohol | ketone | thiol | amide | amine | analine | phenol | phosphate | sulfate |
| Histidine | Amine | alcohol | ketone | thiol | amide | amine | analine | phenol | phosphate | sulfate |
| Histidine | Carboxylic Acid | alcohol | ketone | thiol | amide | amine | analine | phenol | phosphate | sulfate |
| Histidine | Imidazole | imidazole | chlorine | acetamide | carboxylate | | thione | nitro | cyanamide | ketone |
| Hydroquinone | Alcohol | alcohol | ketone | thiol | amide | amine | analine | phenol | phosphate | sulfate |
| Hydroquinone | Phenol | amine | amide | sulfoxide | n | pyridine | cyano | aldehyde | | alchohol |
| Imidazole | Amine | alcohol | ketone | thiol | amide | amine | analine | phenol | phosphate | sulfate |
| Ipriflavone | Ether | aromatic-N | amide | amine | aromatic_s | Sp2 amine | sulfoxide | chlorate | chlorine | |
| Ipriflavone | Ketone | alcohol | | thiol | amide | amine | analine | phenol | phosphate | sulfate |
| Isoleucine | Amine | alcohol | ketone | thiol | amide | amine | analine | phenol | phosphate | sulfate |
| Isoleucine | Carboxylic Acid | alcohol | ketone | thiol | amide | amine | analine | phenol | phosphate | sulfate |
| lactobionic acid | Carboxylic Acid | alcohol | ketone | thiol | amide | amine | analine | phenol | phosphate | sulfate |
| Lactobionic acid | alcohol | alcohol | ketone | thiol | amide | amine | analine | phenol | phosphate | sulfate |
| Lactobionic acid | Ether | aromatic-N | amide | amine | aromatic_s | Sp2 amine | sulfoxide | chlorate | chlorine | |
| Lauric acid | Carboxylic Acid | alcohol | ketone | thiol | amide | amine | analine | phenol | phosphate | sulfate |
| Leucine | Carboxylic Acid | alcohol | ketone | thiol | amide | amine | analine | phenol | phosphate | sulfate |
| Leucine | Amine | alcohol | ketone | thiol | amide | amine | analine | phenol | phosphate | sulfate |
| Lysine | Amine | alcohol | ketone | thiol | amide | amine | analine | phenol | phosphate | sulfate |
| Lysine | Carboxylic Acid | alcohol | ketone | thiol | amide | amine | analine | phenol | phosphate | sulfate |

TABLE II-continued

| Co-crystal Former | | | | Interacting Group | | | | | |
|---|---|---|---|---|---|---|---|---|---|
| Maleic | Carboxylic Acid | alcohol | ketone | thiol | amide | amine | analine | phenol | phosphate | sulfate |
| Malic Acid | Alcohol | alcohol | ketone | thiol | amide | amine | analine | phenol | phosphate | sulfate |
| Malic Acid | Carboxylic Acid | alcohol | ketone | thiol | amide | amine | analine | phenol | phosphate | sulfate |
| Malonic | Carboxylic Acid | alcohol | ketone | thiol | amide | amine | analine | phenol | phosphate | sulfate |
| Mandelic Acid | Alcohol | alcohol | ketone | thiol | amide | amine | analine | phenol | phosphate | sulfate |
| Mandelic Acid | Carboxylic Acid | alcohol | ketone | thiol | amide | amine | analine | phenol | phosphate | sulfate |
| Methionine | Amine | alcohol | ketone | thiol | amide | amine | analine | phenol | phosphate | sulfate |
| Methionine | Carboxylic Acid | alcohol | ketone | thiol | amide | amine | analine | phenol | phosphate | sulfate |
| Methionine | Thioether | —N | amide | amine | —s | Sp2 amine | sulfoxide | chlorate | chlorine | |

| Co-crystal Former | | | | Interacting Group | | | | | |
|---|---|---|---|---|---|---|---|---|---|
| Glutamine | sulfone | nitrate | pyridine | | carboxilic acid | metals | aldehyde | ester | ether | cyano |
| Glutamine | sulfone | nitrate | pyridine | | Carboxylic Acid | metals | aldehyde | ester | ether | cyano |
| Glutamine | sulfone | nitrate | pyridine | | carboxilic acid | metals | aldehyde | ester | ether | cyano |
| Glutaric Acid | sulfone | nitrate | pyridine | | carboxilic acid | metals | aldehyde | ester | ether | cyano |
| Glycine | sulfone | nitrate | pyridine | | carboxilic acid | metals | aldehyde | ester | ether | cyano |
| Glycine | sulfone | nitrate | pyridine | | carboxilic acid | metals | aldehyde | ester | ether | cyano |
| Glycolic Acid | sulfone | nitrate | pyridine | | Carboxylic Acid | metals | aldehyde | ester | ether | cyano |
| Glycolic Acid | sulfone | nitrate | pyridine | | carboxilic acid | metals | aldehyde | ester | ether | cyano |
| Hippuric Acid | sulfone | nitrate | pyridine | | carboxilic acid | metals | aldehyde | ester | ether | cyano |
| Hippuric Acid | sulfone | nitrate | pyridine | | carboxilic acid | metals | aldehyde | ester | ether | cyano |
| Hippuric Acid | sulfone | nitrate | pyridine | | carboxilic acid | metals | aldehyde | ester | ether | cyano |
| Histidine | sulfone | nitrate | pyridine | | carboxilic acid | metals | aldehyde | ester | ether | cyano |
| Histidine | sulfone | nitrate | pyridine | | carboxilic acid | metals | aldehyde | ester | ether | cyano |
| Histidine | cyano | Carboxylic Acid | alcohol | | thiol | amine | phosphinic acid hemihydrate | chlorine | sulfonyl | sulfoxide |
| Hydroquinone | sulfone | nitrate | pyridine | | Carboxylic Acid | metals | aldehyde | ester | ether | cyano |
| Hydroquinone | | ester | ether | n-oxide | chlorine | fluorine | bromine | iodine | ketone | sulfonic acid |
| Imidazole | sulfone | nitrate | pyridine | | carboxilic acid | metals | aldehyde | ester | ether | cyano |
| Ipriflavone | cyano | ester | amine | nitro | nitrate | bromine | aldehyde | ketone | peroxide | epoxide |
| Ipriflavone | sulfone | nitrate | pyridine | | Carboxylic Acid | metals | aldehyde | ester | ether | cyano |
| Isoleucine | sulfone | nitrate | pyridine | | carboxilic acid | metals | aldehyde | ester | ether | cyano |
| Isoleucine | sulfone | nitrate | pyridine | | carboxilic acid | metals | aldehyde | ester | ether | cyano |
| lactobionic acid | sulfone | nitrate | pyridine | | carboxilic acid | metals | aldehyde | ester | ether | cyano |
| Lactobionic acid | sulfone | nitrate | pyridine | carboxilic acid | metals | aldehyde | ester | ether | cyano | |
| Lactobionic acid | cyano | ester | amine | nitro | nitrate | bromine | aldehyde | ketone | peroxide | epoxide |
| Lauric acid | sulfone | nitrate | pyridine | | carboxilic acid | | aldehyde | ester | ether | cyano |
| Leucine | sulfone | nitrate | pyridine | | Carboxylic Acid | metals | aldehyde | ester | ether | cyano |
| Leucine | sulfone | nitrate | pyridine | | carboxilic acid | metals | aldehyde | ester | ether | cyano |
| Lysine | sulfone | nitrate | pyridine | | carboxilic acid | metals | aldehyde | ester | ether | cyano |
| Lysine | sulfone | nitrate | pyridine | | carboxilic acid | metals | aldehyde | ester | ether | cyano |
| Maleic | sulfone | nitrate | pyridine | | carboxilic acid | metals | aldehyde | ester | ether | cyano |
| Malic Acid | sulfone | nitrate | pyridine | | Carboxylic Acid | metals | aldehyde | ester | ether | cyano |
| Malic Acid | sulfone | nitrate | pyridine | | carboxilic acid | metals | aldehyde | ester | ether | cyano |
| Malonic | sulfone | nitrate | pyridine | | carboxilic acid | metals | aldehyde | ester | ether | cyano |
| Mandelic Acid | sulfone | nitrate | pyridine | | Carboxylic Acid | metals | aldehyde | ester | ether | cyano |
| Mandelic Acid | sulfone | nitrate | pyridine | | carboxilic acid | metals | aldehyde | ester | ether | cyano |
| Methionine | sulfone | nitrate | pyridine | | carboxilic acid | metals | aldehyde | ester | ether | cyano |
| Methionine | sulfone | nitrate | pyridine | | carboxilic acid | metals | aldehyde | ester | ether | cyano |
| Methionine | cyano | ester | amine | nitro | nitrate | bromine | aldehyde | ketone | peroxide | epoxide |

| Co-crystal Former | | | | Interacting Group | | | | | |
|---|---|---|---|---|---|---|---|---|---|
| Glutamine | | furan | bromine | chlorine | s-heterocyclic | pyridine | cyano | n-heterocyclic | ketone |
| Glutamine | | furan | bromine | chlorine | s-heterocyclic | pyridine | cyano | n-heterocyclic | ketone |
| Glutamine | | furan | bromine | chlorine | s-heterocyclic | pyridine | cyano | n-heterocyclic | ketone |
| Glutaric Acid | | furan | bromine | chlorine | s-heterocyclic | pyridine | cyano | n-heterocyclic | ketone |
| Glycine | | furan | bromine | chlorine | s-heterocyclic | pyridine | cyano | n-heterocyclic | ketone |
| Glycine | | furan | bromine | chlorine | s-heterocyclic | pyridine | cyano | n-heterocyclic | ketone |
| Glycolic Acid | | furan | bromine | chlorine | s-heterocyclic | pyridine | cyano | n-heterocyclic | ketone |
| Glycolic Acid | | furan | bromine | chlorine | s-heterocyclic | pyridine | cyano | n-heterocyclic | ketone |
| Hippuric Acid | | furan | bromine | chlorine | s-heterocyclic | pyridine | cyano | n-heterocyclic | ketone |
| Hippuric Acid | | furan | bromine | chlorine | s-heterocyclic | pyridine | cyano | n-heterocyclic | ketone |
| Hippuric Acid | | furan | bromine | chlorine | s-heterocyclic | pyridine | cyano | n-heterocyclic | ketone |
| Histidine | | furan | bromine | chlorine | s-heterocyclic | pyridine | cyano | n-heterocyclic | ketone |
| Histidine | | furan | bromine | chlorine | s-heterocyclic | pyridine | cyano | n-heterocyclic | ketone |
| Histidine | amide | fluorine | sulfonate ester | | | | | | |
| Hydroquinone | | furan | bromine | chlorine | s-heterocyclic | pyridine | cyano | n-heterocyclic | ketone |
| Hydroquinone | sulfate | phosphate | phosphonic acid | carboxylic acid | nitro | sulfone | analine | | |
| Imidazole | | furan | bromine | chlorine | s-heterocyclic | pyridine | cyano | n-heterocyclic | ketone |
| Ipriflavone | | heterocyclic-S | iodine | ester | ether | carboxylic acid | sulfate | sulfone | |
| Ipriflavone | | furan | bromine | chlorine | s-heterocyclic | pyridine | cyano | n-heterocyclic | ketone |
| Isoleucine | | furan | bromine | chlorine | s-heterocyclic | pyridine | cyano | n-heterocyclic | ketone |
| Isoleucine | | furan | bromine | chlorine | s-heterocyclic | pyridine | cyano | n-heterocyclic | ketone |
| lactobionic acid | | furan | bromine | chlorine | s-heterocyclic | pyridine | cyano | n-heterocyclic | ketone |
| Lactobionic acid | furan | bromine | chlorine | s-heterocyclic | pyridine | cyano | n-heterocyclic | ketone | phosphate ester |

TABLE II-continued

| Co-crystal Former | | | | | | | | | | |
|---|---|---|---|---|---|---|---|---|---|---|
| Lactobionic acid | | heterocyclic-S | iodine | ester | ether | carboxylic acid | sulfate | sulfone | | |
| Lauric acid | furan | bromine | chlorine | s-heterocyclic | pyridine | cyano | | n-heterocyclic | ketone | |
| Leucine | furan | bromine | chlorine | s-heterocyclic | pyridine | cyano | | n-heterocyclic | ketone | |
| Leucine | furan | bromine | chlorine | s-heterocyclic | pyridine | cyano | | n-heterocyclic | ketone | |
| Lysine | furan | bromine | chlorine | s-heterocyclic | pyridine | cyano | | n-heterocyclic | ketone | |
| Lysine | furan | bromine | chlorine | s-heterocyclic | pyridine | cyano | | n-heterocyclic | ketone | |
| Maleic | furan | bromine | chlorine | s-heterocyclic | pyridine | cyano | | n-heterocyclic | ketone | |
| Malic Acid | furan | bromine | chlorine | s-heterocyclic | pyridine | cyano | | n-heterocyclic | ketone | |
| Malic Acid | furan | bromine | chlorine | s-heterocyclic | pyridine | cyano | | n-heterocyclic | ketone | |
| Malonic | furan | bromine | chlorine | s-heterocyclic | pyridine | cyano | | n-heterocyclic | ketone | |
| Mandelic Acid | furan | bromine | chlorine | s-heterocyclic | pyridine | cyano | | n-heterocyclic | ketone | |
| Mandelic Acid | furan | bromine | chlorine | s-heterocyclic | pyridine | cyano | | n-heterocyclic | ketone | |
| Methionine | furan | bromine | chlorine | s-heterocyclic | pyridine | cyano | | n-heterocyclic | ketone | |
| Methionine | furan | bromine | chlorine | s-heterocyclic | pyridine | cyano | | n-heterocyclic | ketone | |
| Methionine | Ag | Se | heterocyclic-S | iodine | ester | ether | carboxylic acid | sulfate | sulfone | |

| Co-crystal Former | Interacting Group | | | | | | | | | |
|---|---|---|---|---|---|---|---|---|---|---|
| Glutamine | phosphate ester | | fluorine | carbamate | imidazole | BF4 | N—SO2 | thiourea | iodine | |
| Glutamine | phosphate ester | | fluorine | carbamate | imidazole | BF4 | N—SO2 | thiourea | iodine | |
| Glutamine | phosphate ester | | fluorine | carbamate | imidazole | BF4 | N—SO2 | thiourea | iodine | epoxide peroxide |
| Glutaric Acid | phosphate ester | | fluorine | carbamate | imidazole | BF4 | N—SO2 | thiourea | iodine | |
| Glycine | phosphate ester | | fluorine | carbamate | imidazole | BF4 | N—SO2 | thiourea | iodine | |
| Glycine | phosphate ester | | fluorine | carbamate | imidazole | BF4 | N—SO2 | thiourea | iodine | |
| Glycolic Acid | phosphate ester | | fluorine | carbamate | imidazole | BF4 | N—SO2 | thiourea | iodine | epoxide |
| Glycolic Acid | phosphate ester | | fluorine | carbamate | imidazole | BF4 | N—SO2 | thiourea | iodine | |
| Hippuric Acid | phosphate ester | | fluorine | carbamate | imidazole | BF4 | N—SO2 | thiourea | iodine | epoxide peroxide |
| Hippuric Acid | phosphate ester | | fluorine | carbamate | imidazole | BF4 | N—SO2 | thiourea | iodine | |
| Hippuric Acid | phosphate ester | | fluorine | carbamate | imidazole | BF4 | N—SO2 | thiourea | iodine | |
| Histidine | phosphate ester | | fluorine | carbamate | imidazole | BF4 | N—SO2 | thiourea | iodine | |
| Histidine | phosphate ester | | fluorine | carbamate | imidazole | BF4 | N—SO2 | thiourea | iodine | |
| Histidine | | | | | | | | | | |
| Hydroquinone | phosphate ester | | fluorine | carbamate | imidazole | BF4 | N—SO2 | thiourea | iodine | epoxide |
| Hydroquinone | | | | | | | | | | |
| Imidazole | phosphate ester | | fluorine | carbamate | imidazole | BF4 | N—SO2 | thiourea | iodine | |
| Ipriflavone | | alcohol | | phospphate | cyanamide | | | | | |
| Ipriflavone | phosphate ester | | fluorine | carbamate | imidazole | BF4 | N—SO2 | thiourea | iodine | |
| Isoleucine | phosphate ester | | fluorine | carbamate | imidazole | BF4 | N—SO2 | thiourea | iodine | |
| Isoleucine | phosphate ester | | fluorine | carbamate | imidazole | BF4 | N—SO2 | thiourea | iodine | |
| lactobionic acid | phosphate ester | | fluorine | carbamate | imidazole | BF4 | N—SO2 | thiourea | iodine | |
| Lactobionic acid | | fluorine | carbamate | imidazole | BF4 | | | | | |
| Lactobionic acid | | alcohol | | phospphate | cyanamide | | | | | |
| Lauric acid | phosphate ester | | fluorine | carbamate | imidazole | BF4 | N—SO2 | thiourea | iodine | |
| Leucine | phosphate ester | | fluorine | carbamate | imidazole | BF4 | N—SO2 | thiourea | iodine | |
| Leucine | phosphate ester | | fluorine | carbamate | imidazole | BF4 | N—SO2 | thiourea | iodine | |
| Lysine | phosphate ester | | fluorine | carbamate | imidazole | BF4 | N—SO2 | thiourea | iodine | |
| Lysine | phosphate ester | | fluorine | carbamate | imidazole | BF4 | N—SO2 | thiourea | iodine | |
| Maleic | phosphate ester | | fluorine | carbamate | imidazole | BF4 | N—SO2 | thiourea | iodine | |
| Malic Acid | phosphate ester | | fluorine | carbamate | imidazole | BF4 | N—SO2 | thiourea | iodine | epoxide |
| Malic Acid | phosphate ester | | fluorine | carbamate | imidazole | BF4 | N—SO2 | thiourea | iodine | |
| Malonic | phosphate ester | | fluorine | carbamate | imidazole | BF4 | N—SO2 | thiourea | iodine | |
| Mandelic Acid | phosphate ester | | fluorine | carbamate | imidazole | BF4 | N—SO2 | thiourea | iodine | epoxide |
| Mandelic Acid | phosphate ester | | fluorine | carbamate | imidazole | BF4 | N—SO2 | thiourea | iodine | |
| Methionine | phosphate ester | | fluorine | carbamate | imidazole | BF4 | N—SO2 | thiourea | iodine | |
| Methionine | phosphate ester | | fluorine | carbamate | imidazole | BF4 | N—SO2 | thiourea | iodine | |
| Methionine | | alcohol | | phospphate | | | | | | |

| Co-crystal Former | Co-crystal Former Functional Group | Interacting Group | | | | | | | |
|---|---|---|---|---|---|---|---|---|---|
| Nicotinamide | Pyridine | *alcohol | * | *amide | nitro | *amine | *Carboxylic Acid | *sulfonamide | |
| Nicotinamide | Amide | alcohol | ketone | thiol | amide | amine | analine | phenol | phosphate |
| Nicotinic Acid | Carboxylic Acid | alcohol | ketone | thiol | amide | amine | analine | phenol | phosphate |
| Nicotinic Acid | Pyridine | *alcohol | * | *amide | nitro | *amine | *Carboxylic Acid | *sulfonamide | |
| Orotic acid | Carboxylic Acid | alcohol | ketone | thiol | amide | amine | analine | phenol | phosphate |
| Orotic acid | Lactam | alcohol | ketone | thiol | amide | amine | analine | phenol | phosphate |
| Oxalic acid | Carboxylic Acid | alcohol | ketone | thiol | amide | amine | analine | phenol | phosphate |
| Palmitic acid | Carboxylic Acid | alcohol | ketone | thiol | amide | amine | analine | phenol | phosphate |
| Pamoic acid | Carboxylic Acid | alcohol | ketone | thiol | amide | amine | analine | phenol | phosphate |
| Pamoic acid | alcohol | alcohol | ketone | thiol | amide | amine | analine | phenol | phosphate |
| Pamoic acid | Phenol | amine | amide | sulfoxide | n | pyridine | cyano | aldehyde | |
| Phenylalanine | Amine | alcohol | ketone | thiol | amide | amine | analine | phenol | phosphate |
| Phenylalanine | Carboxylic Acid | alcohol | ketone | thiol | amide | amine | analine | phenol | phosphate |
| Piperazine | Amine | alcohol | ketone | thiol | amide | amine | analine | phenol | phosphate |
| Procaine | Amine | alcohol | ketone | thiol | amide | amine | analine | phenol | phosphate |
| Procaine | Ketone | alcohol | ketone | thiol | amide | amine | analine | phenol | phosphate |
| Proline | Carboxylic Acid | alcohol | ketone | thiol | amide | amine | analine | phenol | phosphate |

TABLE II-continued

| Co-crystal Former | | | | | | | | | |
|---|---|---|---|---|---|---|---|---|---|
| Proline | Amine | alcohol | ketone | thiol | amide | amine | analine | phenol | phosphate |
| p-Toluenesulfonic acid | Sulfonic Acid | pyridine | ketone | aldehyde | ether | ester | amide | Carboxylic Acid | amine |
| Pyridoxamine | Alcohol | alcohol | ketone | thiol | amide | amine | analine | phenol | phosphate |
| Pyridoxamine | Amine | alcohol | ketone | thiol | amide | amine | analine | phenol | phosphate |
| Pyridoxamine | Pyridine | *alcohol | | * | *amide | nitro | *amine | *Carboxylic Acid | *sulfonamide |
| Pyridoxine (4-Pyridoxic Acid) | Pyridine | *alcohol | pyridinium | * | *amide | nitro | *amine | *Carboxylic Acid | *sulfonamide |
| Pyridoxine (4-Pyridoxic Acid) | Alcohol | alcohol | ketone | thiol | amide | amine | analine | phenol | phosphate |
| Pyroglutamic acid | Carboxylic Acid | alcohol | ketone | thiol | amide | amine | analine | phenol | phosphate |
| Pyroglutamic acid | Lactam | alcohol | ketone | thiol | amide | amine | analine | phenol | phosphate |
| Quercetin | Ketone | alcohol | | thiol | amide | amine | analine | phenol | phosphate |
| Quercetin | Phenol | amine | amide | sulfoxide | n | pyridine | cyano | aldehyde | |
| Quercetin | Ether | aromatic-N | amide | amine | aromatic_s | Sp2 amine | sulfoxide | chlorate | chlorine |
| Resveratrol | Ketone | alcohol | | thiol | amide | amine | analine | phenol | phosphate |
| Resveratrol | Phenol | amine | amide | sulfoxide | n | pyridine | cyano | aldehyde | |
| Saccharin | Amide | alcohol | ketone | thiol | amide | amine | analine | phenol | phosphate |
| Saccharin | Ketone | alcohol | | thiol | amide | amine | analine | phenol | phosphate |
| Saccharin | Sulfoxide | pyridine | ketone | aldehyde | ether | ester | amide | Carboxylic Acid | amine |

| Co-crystal Former | Interacting Group | | | | | | | | |
|---|---|---|---|---|---|---|---|---|---|
| Nicotinamide | *ketone | ether | triazole | ammonium | oxime | *chlorine | | thiol | n-heterocyclic ring |
| Nicotinamide | sulfate | sulfone | nitrate | pyridine | | Carboxylic Acid | metals | aldehyde | ester | ether |
| Nicotinic Acid | sulfate | sulfone | nitrate | pyridine | | Carboxylic Acid | metals | aldehyde | ester | ether |
| Nicotinic Acid | *ketone | ether | triazole | ammonium | oxime | *chlorine | | thiol | n-heterocyclic ring |
| Orotic acid | sulfate | sulfone | nitrate | pyridine | | carboxilic acid | | aldehyde | ester | ether |
| Orotic acid | sulfate | sulfone | nitrate | pyridine | | Carboxylic Acid | metals | aldehyde | ester | ether |
| Oxalic acid | sulfate | sulfone | nitrate | pyridine | | carboxilic acid | | aldehyde | ester | ether |
| Palmitic acid | sulfate | sulfone | nitrate | pyridine | | carboxilic acid | | aldehyde | ester | ether |
| Pamoic acid | sulfate | sulfone | nitrate | pyridine | | carboxilic acid | | aldehyde | ester | ether |
| Pamoic acid | sulfate | sulfone | nitrate | pyridine | carboxilic acid | metals | aldehyde | ester | ether | cyano |
| Pamoic acid | alchohol | | ester | ether | n-oxide | chlorine | fluorine | bromine | iodine | ketone |
| Phenylalanine | sulfate | sulfone | nitrate | pyridine | | carboxilic acid | metals | aldehyde | ester | ether |
| Phenylalanine | sulfate | sulfone | nitrate | pyridine | | carboxilic acid | metals | aldehyde | ester | ether |
| Piperazine | sulfate | sulfone | nitrate | pyridine | | carboxilic acid | metals | aldehyde | ester | ether |
| Procaine | sulfate | sulfone | nitrate | pyridine | | carboxilic acid | metals | aldehyde | ester | ether |
| Procaine | sulfate | sulfone | nitrate | pyridine | | Carboxylic Acid | metals | aldehyde | ester | ether |
| Proline | sulfate | sulfone | nitrate | pyridine | | carboxilic acid | metals | aldehyde | ester | ether |
| Proline | sulfate | sulfone | nitrate | pyridine | | carboxilic acid | metals | aldehyde | ester | ether |
| p-Toluenesulfonic acid | metals | thioether | | sulfate | alcohol | | | | | |
| Pyridoxamine | sulfate | sulfone | nitrate | pyridine | | Carboxylic Acid | metals | aldehyde | ester | ether |
| Pyridoxamine | sulfate | sulfone | nitrate | pyridine | | carboxilic acid | metals | aldehyde | ester | ether |
| Pyridoxamine | *ketone | ether | triazole | ammonium | oxime | *chlorine | | thiol | n-heterocyclic ring |
| Pyridoxine (4-Pyridoxic Acid) | *ketone | ether | triazole | ammonium | oxime | *chlorine | | thiol | n-heterocyclic ring |
| Pyridoxine (4-Pyridoxic Acid) | sulfate | sulfone | nitrate | pyridine | | Carboxylic Acid | metals | aldehyde | ester | ether |
| Pyroglutamic acid | sulfate | sulfone | nitrate | pyridine | | carboxilic acid | metals | aldehyde | ester | ether |
| Pyroglutamic acid | sulfate | sulfone | nitrate | pyridine | | Carboxylic Acid | metals | aldehyde | ester | ether |
| Quercetin | sulfate | sulfone | nitrate | Pyridine | | Carboxylic Acid | metals | aldehyde | ester | ether |
| Quercetin | alchohol | | ester | ether | n-oxide | chlorine | fluorine | bromine | iodine | ketone |
| Quercetin | | cyano | ester | amine | nitro | nitrate | bromine | aldehyde | ketone | peroxide |
| Resveratrol | sulfate | sulfone | nitrate | pyridine | | Carboxylic Acid | metals | aldehyde | ester | ether |
| Resveratrol | alchohol | | ester | ether | n-oxide | chlorine | fluorine | bromine | iodine | ketone |
| Saccharin | sulfate | sulfone | nitrate | pyridine | | Carboxylic Acid | metals | aldehyde | ester | ether |
| Saccharin | sulfate | sulfone | nitrate | pyridine | | Carboxylic Acid | metals | aldehyde | ester | ether |
| Saccharin | metals | thioether | | sulfate | alcohol | | | | | |

| Co-crystal Former | Interacting Group | | | | | | | |
|---|---|---|---|---|---|---|---|---|
| Nicotinamide | thionedisulfide | pyrrolidindione | iodine | hydrazone | thiocyanate | *bromine | | hydroxamic acid |
| Nicotinamide | cyano | | furan | bromine | chlorine | s-heterocyclic | pyridine | cyano |
| Nicotinic Acid | cyano | | furan | bromine | chlorine | s-heterocyclic | pyridine | cyano |
| Nicotinic acid | thionedisulfide | pyrrolidindione | iodine | hydrazone | thiocyanate | *bromine | | hydroxamic acid |
| Orotic acid | cyano | | furan | bromine | chlorine | s-heterocyclic | pyridine | cyano |
| Orotic acid | cyano | | furan | bromine | chlorine | s-heterocyclic | pyridine | cyano |
| Oxalic acid | cyano | | furan | bromine | chlorine | s-heterocyclic | pyridine | cyano |
| Palmitic acid | cyano | | furan | bromine | chlorine | s-heterocyclic | pyridine | cyano |
| Pamoic acid | cyano | | furan | bromine | chlorine | s-heterocyclic | pyridine | cyano |
| Pamoic acid | | furan | bromine | chlorine | s-heterocyclic | pyridine | cyano | n-heterocyclic |
| Pamoic acid | sulfonic acid | sulfate | phosphate | phosphonic acid | carboxylic acid | nitro | sulfone | analine |

TABLE II-continued

| | | | | | | | | | |
|---|---|---|---|---|---|---|---|---|---|
| Phenylalanine | cyano | | furan | bromine | chlorine | s-heterocyclic | pyridine | cyano | |
| Phenylalanine | cyano | | furan | bromine | chlorine | s-heterocyclic | pyridine | cyano | |
| Piperazine | cyano | | furan | bromine | chlorine | s-heterocyclic | pyridine | cyano | |
| Procaine | cyano | | furan | bromine | chlorine | s-heterocyclic | pyridine | cyano | |
| Procaine | cyano | | furan | bromine | chlorine | s-heterocyclic | pyridine | cyano | |
| Proline | cyano | | furan | bromine | chlorine | s-heterocyclic | pyridine | cyano | |
| Proline | cyano | | furan | bromine | chlorine | s-heterocyclic | pyridine | cyano | |
| p-Toluenesulfonic acid | | | | | | | | | |
| Pyridoxamine | cyano | | furan | bromine | chlorine | s-heterocyclic | pyridine | cyano | |
| Pyridoxamine | cyano | | furan | bromine | chlorine | s-heterocyclic | pyridine | cyano | |
| Pyridoxamine | thionedisulfide | | iodine | hydrazone | thiocyanate | *bromine | | hydroxamic acid | |
| Pyridoxine (4-Pyridoxic Acid) | thionedisulfide | pyrrolidindione | iodine | hydrazone | thiocyanate | *bromine | | hydroxamic acid | |
| Pyridoxine (4-Pyridoxic Acid) | cyano | | furan | bromine | chlorine | s-heterocyclic | pyridine | cyano | |
| Pyroglutamic acid | cyano | | furan | bromine | chlorine | s-heterocyclic | pyridine | cyano | |
| Pyroglutamic acid | cyano | | furan | bromine | chlorine | s-heterocyclic | pyridine | cyano | |
| Quercetin | cyano | | furan | bromine | chlorine | s-heterocyclic | pyridine | cyano | |
| Quercetin | sulfonic acid | sulfate | phosphate | phosphonic acid | carboxylic acid | nitro | | sulfone | analine |
| Quercetin | epoxide | | | heterocyclic-S | iodine | ester | | ether | carboxylic acid |
| Resveratrol | cyano | | furan | bromine | chlorine | s-heterocyclic | pyridine | cyano | |
| Resveratrol | sulfonic acid | sulfate | phosphate | phosphonic acid | carboxylic acid | nitro | | sulfone | analine |
| Saccharin | cyano | | furan | bromine | chlorine | s-heterocyclic | pyridine | cyano | |
| Saccharin | cyano | | furan | bromine | chlorine | s-heterocyclic | pyridine | cyano | |
| Saccharin | | | | | | | | | |

| Co-crystal Former | | | Interacting Group | | | | | | |
|---|---|---|---|---|---|---|---|---|---|
| Nicotinamide | cyano | carboxamide | *sulfonic acid | *phosphoric acid | N-oxide | ester | ether | fluorine | acetate |
| Nicotinamide | n-heterocyclic | ketone | phosphate ester | | fluorine | carbamate | imidazole | BF4 | |
| Nicotinic Acid | n-heterocyclic | ketone | phosphate ester | | fluorine | carbamate | imidazole | BF4 | |
| Nicotinic Acid | cyano | carboxamide | *sulfonic acid | *phosphoric acid | N-oxide | ester | ether | fluorine | acetate |
| Orotic acid | n-heterocyclic | ketone | phosphate ester | | fluorine | carbamate | imidazole | BF4 | |
| Orotic acid | n-heterocyclic | ketone | phosphate ester | | fluorine | carbamate | imidazole | BF4 | |
| Oxalic acid | n-heterocyclic | ketone | phosphate ester | | fluorine | carbamate | imidazole | BF4 | |
| Palmitic acid | n-heterocyclic | ketone | phosphate ester | | fluorine | carbamate | imidazole | BF4 | |
| Pamoic acid | n-heterocyclic | ketone | phosphate ester | | fluorine | carbamate | imidazole | BF4 | |
| Pamoic acid | ketone | phosphate ester | | fluorine | carbamate | imidazole | BF4 | | |
| Pamoic acid | | | | | | | | | |
| Phenylalanine | n-heterocyclic | ketone | phosphate ester | | fluorine | carbamate | imidazole | BF4 | |
| Phenylalanine | n-heterocyclic | ketone | phosphate ester | | fluorine | carbamate | imidazole | BF4 | |
| Piperazine | n-heterocyclic | ketone | phosphate ester | | fluorine | carbamate | imidazole | BF4 | |
| Procaine | n-heterocyclic | ketone | phosphate ester | | fluorine | carbamate | imidazole | BF4 | |
| Procaine | n-heterocyclic | ketone | phosphate ester | | fluorine | carbamate | imidazole | BF4 | |
| Proline | n-heterocyclic | ketone | phosphate ester | | fluorine | carbamate | imidazole | BF4 | |
| Proline | n-heterocyclic | ketone | phosphate ester | | fluorine | carbamate | imidazole | BF4 | |
| p-Toluenesulfonic acid | | | | | | | | | |
| Pyridoxamine | n-heterocyclic | ketone | phosphate ester | | fluorine | carbamate | imidazole | BF4 | |
| Pyridoxamine | n-heterocyclic | ketone | phosphate ester | | fluorine | carbamate | imidazole | BF4 | |
| Pyridoxamine | cyano | carboxamide | *sulfonic acid | *phosphoric acid | N-oxide | ester | ether | fluorine | acetate |
| Pyridoxine (4-Pyridoxic Acid) | cyano | carboxamide | *sulfonic acid | *phosphoric acid | N-oxide | ester | ether | fluorine | acetate |
| Pyridoxine (4-Pyridoxic Acid) | n-heterocyclic | ketone | phosphate ester | | fluorine | carbamate | imidazole | BF4 | |
| Pyroglutamic acid | n-heterocyclic | ketone | phosphate ester | | fluorine | carbamate | imidazole | BF4 | |
| Pyroglutamic acid | n-heterocyclic | ketone | phosphate ester | | fluorine | carbamate | imidazole | BF4 | |
| Quercetin | n-heterocyclic | ketone | phosphate ester | | fluorine | carbamate | imidazole | BF4 | |
| Quercetin | | | | | | | | | |
| Quercetin | sulfate | sulfone | | alcohol | | phospphate | cyanamide | | |
| Resveratrol | n-heterocyclic | ketone | phosphate ester | | fluorine | carbamate | imidazole | BF4 | |
| Resveratrol | n-heterocyclic | ketone | phosphate ester | | fluorine | carbamate | imidazole | BF4 | |
| Saccharin | n-heterocyclic | ketone | phosphate ester | | fluorine | carbamate | imidazole | BF4 | |
| Saccharin | n-heterocyclic | ketone | phosphate ester | | fluorine | carbamate | imidazole | BF4 | |
| Saccharin | | | | | | | | | |

| Co-crystal Former | | | Interacting Group | | | |
|---|---|---|---|---|---|---|
| Nicotinamide | thione | dithiadiazocyclopentadienyl | | | | |
| Nicotinamide | | N—SO2 | | thiourea | iodine | epoxide | peroxide |
| Nicotinic Acid | | N—SO2 | | thiourea | iodine | | |
| Nicotinic Acid | thione | dithiadiazocyclopentadienyl | | | | |
| Orotic acid | | N—SO2 | | thiourea | iodine | | |
| Orotic acid | | N—SO2 | | thiourea | iodine | epoxide | peroxide |
| Oxalic acid | | N—SO2 | | thiourea | iodine | | |
| Palmitic acid | | N—SO2 | | thiourea | iodine | | |
| Pamoic acid | | N—SO2 | | thiourea | iodine | | |
| Pamoic acid | | | | | | |
| Pamoic acid | | | | | | |
| Phenylalanine | | N—SO2 | | thiourea | iodine | | |

TABLE II-continued

| | | | | | |
|---|---|---|---|---|---|
| Phenylalanine | N—SO2 | thiourea | iodine | | |
| Piperazine | N—SO2 | thiourea | iodine | | |
| Procaine | N—SO2 | thiourea | iodine | | |
| Procaine | N—SO2 | thiourea | iodine | | |
| Proline | N—SO2 | thiourea | iodine | | |
| Proline | N—SO2 | thiourea | iodine | | |
| p-Toluenesulfonic acid | | | | | |
| Pyridoxamine | N—SO2 | thiourea | iodine | epoxide | |
| Pyridoxamine | N—SO2 | thiourea | iodine | | |
| Pyridoxamine | thione | dithiadiazocyclopentadienyl | | | |
| Pyridoxine (4-Pyridoxic Acid) | thione | dithiadiazocyclopentadienyl | | | |
| Pyridoxine (4-Pyridoxic Acid) | N—SO2 | thiourea | iodine | epoxide | |
| Pyroglutamic acid | N—SO2 | thiourea | iodine | | |
| Pyroglutamic acid | N—SO2 | thiourea | iodine | epoxide | peroxide |
| Quercetin | N—SO2 | thiourea | iodine | | |
| Quercetin | | | | | |
| Quercetin | | | | | |
| Resveratrol | N—SO2 | thiourea | iodine | | |
| Resveratrol | | | | | |
| Saccharin | N—SO2 | thiourea | iodine | epoxide | peroxide |
| Saccharin | N—SO2 | thiourea | iodine | | |
| Saccharin | | | | | |

| Co-crystal Former | Co-crystal Former Functional Group | Interacting Group | | | | | | | |
|---|---|---|---|---|---|---|---|---|---|
| Saccharin | Amine | alcohol | ketone | thiol | amide | | analine | phenol | phosphate | sulfate |
| Salicylic Acid | Carboxylic Acid | alcohol | ketone | thiol | amide | amine | analine | phenol | phosphate | sulfate |
| Salicylic Acid | Alcohol | alcohol | ketone | thiol | amide | amine | analine | phenol | phosphate | sulfate |
| Salicylic Acid, 4-amino | Carboxylic Acid | alcohol | ketone | thiol | amide | amine | analine | phenol | phosphate | sulfate |
| Salicylic Acid, 4-amino | alcohol | alcohol | ketone | thiol | amide | amine | analine | phenol | phosphate | sulfate |
| Salicylic Acid, 4-amino | Amine | alcohol | ketone | thiol | amide | amine | analine | phenol | phosphate | sulfate |
| Sebacic acid | Carboxylic Acid | alcohol | ketone | thiol | amide | amine | analine | phenol | phosphate | sulfate |
| Serine | Carboxylic Acid | alcohol | ketone | thiol | amide | amine | analine | phenol | phosphate | sulfate |
| Serine | Amine | alcohol | ketone | thiol | amide | amine | analine | phenol | phosphate | sulfate |
| Serine | Alcohol | alcohol | ketone | thiol | amide | amine | analine | phenol | phosphate | sulfate |
| Stearic acid | Carboxylic Acid | alcohol | ketone | thiol | amide | amine | analine | phenol | phosphate | sulfate |
| Succinic Acid | Carboxylic Acid | alcohol | ketone | thiol | amide | amine | analine | phenol | phosphate | sulfate |
| Tartaric Acid | Carboxylic Acid | alcohol | ketone | thiol | amide | amine | analine | phenol | phosphate | sulfate |
| Threonine | Amine | alcohol | ketone | thiol | amide | amine | analine | phenol | phosphate | sulfate |
| Threonine | Carboxylic Acid | alcohol | ketone | thiol | amide | amine | analine | phenol | phosphate | sulfate |
| Threonine | alcohol | alcohol | ketone | thiol | amide | amine | analine | phenol | phosphate | sulfate |
| Tris | Amine | alcohol | ketone | thiol | amide | amine | analine | phenol | phosphate | sulfate |
| Tris | Alcohol | alcohol | ketone | thiol | amide | amine | analine | phenol | phosphate | sulfate |
| Tryptophan | Amine | alcohol | ketone | thiol | amide | amine | analine | phenol | phosphate | sulfate |
| Tryptophan | Carboxylic Acid | alcohol | ketone | thiol | amide | amine | analine | phenol | phosphate | sulfate |
| Tryptophan | Indole | *alcohol | pyridinium | * | *amide | nitro | *amine | *carboxilic acid | *sulfonamide | *ketone |
| Tyrosine | Amine | alcohol | ketone | thiol | amide | amine | analine | phenol | phosphate | sulfate |
| Tyrosine | Carboxylic Acid | alcohol | ketone | thiol | amide | amine | analine | phenol | phosphate | sulfate |
| Tyrosine | Alcohol | alcohol | ketone | thiol | amide | amine | analine | phenol | phosphate | sulfate |
| Urea | Ketone | alcohol | | thiol | amide | amine | analine | phenol | phosphate | sulfate |
| Urea | Amine | alcohol | ketone | thiol | amide | amine | analine | phenol | phosphate | sulfate |
| Urea | Amide | alcohol | ketone | thiol | amide | amine | analine | phenol | phosphate | sulfate |
| Valine | Amine | alcohol | ketone | thiol | amide | amine | analine | phenol | phosphate | sulfate |
| Valine | Carboxylic Acid | alcohol | ketone | thiol | amide | amine | analine | phenol | phosphate | sulfate |
| Vitamin K5 | Amine | alcohol | ketone | thiol | amide | amine | analine | phenol | phosphate | sulfate |
| Vitamin K5 | Alcohol | alcohol | ketone | thiol | amide | amine | analine | phenol | phosphate | sulfate |
| Xylitol | Alcohol | alcohol | ketone | thiol | amide | amine | analine | phenol | phosphate | sulfate |

| Co-crystal Former | Interacting Group | | | | | | | | |
|---|---|---|---|---|---|---|---|---|---|
| Saccharin | sulfone | nitrate | pyridine | | Carboxylic Acid | metals | aldehyde | ester | ether | cyano |
| Salicylic Acid | sulfone | nitrate | pyridine | | carboxilic acid | metals | aldehyde | ester | ether | cyano |
| Salicylic Acid | sulfone | nitrate | pyridine | | Carboxylic Acid | metals | aldehyde | ester | ether | cyano |
| Salicylic Acid, 4-amino | sulfone | nitrate | pyridine | | carboxilic acid | metals | aldehyde | ester | ether | cyano |
| Salicylic Acid, 4-amino | sulfone | nitrate | pyridine | carboxilic acid | metals | aldehyde | ester | ether | cyano |
| Salicylic Acid, 4-amino | sulfone | nitrate | pyridine | | carboxilic acid | metals | aldehyde | ester | ether | cyano |
| Sebacic acid | sulfone | nitrate | pyridine | | carboxilic acid | metals | aldehyde | ester | ether | cyano |
| Serine | sulfone | nitrate | pyridine | | Carboxylic Acid | metals | aldehyde | ester | ether | cyano |
| Serine | sulfone | nitrate | pyridine | | carboxilic acid | metals | aldehyde | ester | ether | cyano |
| Serine | sulfone | nitrate | pyridine | | Carboxylic Acid | metals | aldehyde | ester | ether | cyano |
| Stearic acid | sulfone | nitrate | pyridine | | carboxilic acid | metals | aldehyde | ester | ether | cyano |
| Succinic Acid | sulfone | nitrate | pyridine | | Carboxylic Acid | metals | aldehyde | ester | ether | cyano |

TABLE II-continued

| Co-crystal Former | | | | | | | | | |
|---|---|---|---|---|---|---|---|---|---|
| Tartaric Acid | sulfone | nitrate | pyridine | Carboxylic Acid | metals | aldehyde | ester | ether | cyano |
| Threonine | sulfone | nitrate | pyridine | carboxilic acid | metals | aldehyde | ester | ether | cyano |
| Threonine | sulfone | nitrate | pyridine | carboxilic acid | metals | aldehyde | ester | ether | cyano |
| Threonine | sulfone | nitrate | pyridine | Carboxylic Acid | metals | aldehyde | ester | ether | cyano |
| Tris | sulfone | nitrate | pyridine | carboxilic acid | metals | aldehyde | ester | ether | cyano |
| Tris | sulfone | nitrate | pyridine | Carboxylic Acid | metals | aldehyde | ester | ether | cyano |
| Tryptophan | sulfone | nitrate | pyridine | carboxilic acid | metals | aldehyde | ester | ether | cyano |
| Tryptophan | sulfone | nitrate | pyridine | carboxilic acid | metals | aldehyde | ester | ether | cyano |
| Tryptophan | ether | triazole | ammonium | oxime | *chlorine | | thiol | n-heterocyclic ring | thionedisulfide |
| Tyrosine | sulfone | nitrate | pyridine | carboxilic acid | metals | aldehyde | ester | ether | cyano |
| Tyrosine | sulfone | nitrate | pyridine | carboxilic acid | metals | aldehyde | ester | ether | cyano |
| Tyrosine | sulfone | nitrate | pyridine | Carboxylic Acid | metals | aldehyde | ester | ether | cyano |
| Urea | sulfone | nitrate | pyridine | Carboxylic Acid | metals | aldehyde | ester | ether | cyano |
| Urea | sulfone | nitrate | pyridine | carboxilic acid | metals | aldehyde | ester | ether | cyano |
| Urea | sulfone | nitrate | pyridine | Carboxylic Acid | metals | aldehyde | ester | ether | cyano |
| Valine | sulfone | nitrate | pyridine | carboxilic acid | metals | aldehyde | ester | ether | cyano |
| Valine | sulfone | nitrate | pyridine | carboxilic acid | metals | aldehyde | ester | ether | cyano |
| Vitamin K5 | sulfone | nitrate | pyridine | carboxilic acid | metals | aldehyde | ester | ether | cyano |
| Vitamin K5 | sulfone | nitrate | pyridine | Carboxylic Acid | metals | aldehyde | ester | ether | cyano |
| Xylitol | sulfone | nitrate | pyridine | Carboxylic Acid | metals | aldehyde | ester | ether | cyano |

| Co-crystal Former | Interacting Group | | | | | | |
|---|---|---|---|---|---|---|---|
| Saccharin | | furan | bromine | chlorine | s-heterocyclic | pyridine | cyano | n-heterocyclic |
| Salicylic Acid | | furan | bromine | chlorine | s-heterocyclic | pyridine | cyano | n-heterocyclic |
| Salicylic Acid | | furan | bromine | chlorine | s-heterocyclic | pyridine | cyano | n-heterocyclic |
| Salicylic Acid, 4-amino | | furan | bromine | chlorine | s-heterocyclic | pyridine | cyano | n-heterocyclic |
| Salicylic Acid, 4-amino | furan | bromine | chlorine | s-heterocyclic | pyridine | cyano | n-heterocyclic | ketone |
| Salicylic Acid, 4-amino | | furan | bromine | chlorine | s-heterocyclic | pyridine | cyano | n-heterocyclic |
| Sebacic acid | | furan | bromine | chlorine | s-heterocyclic | pyridine | cyano | n-heterocyclic |
| Serine | | furan | bromine | chlorine | s-heterocyclic | pyridine | cyano | n-heterocyclic |
| Serine | | furan | bromine | chlorine | s-heterocyclic | pyridine | cyano | n-heterocyclic |
| Serine | | furan | bromine | chlorine | s-heterocyclic | pyridine | cyano | n-heterocyclic |
| Stearic acid | | furan | bromine | chlorine | s-heterocyclic | pyridine | cyano | n-heterocyclic |
| Succinic Acid | | furan | bromine | chlorine | s-heterocyclic | pyridine | cyano | n-heterocyclic |
| Tartaric Acid | | furan | bromine | chlorine | s-heterocyclic | pyridine | cyano | n-heterocyclic |
| Threonine | | furan | bromine | chlorine | s-heterocyclic | pyridine | cyano | n-heterocyclic |
| Threonine | | furan | bromine | chlorine | s-heterocyclic | pyridine | cyano | n-heterocyclic |
| Threonine | | furan | bromine | chlorine | s-heterocyclic | pyridine | cyano | n-heterocyclic |
| Tris | | furan | bromine | chlorine | s-heterocyclic | pyridine | cyano | n-heterocyclic |
| Tris | | furan | bromine | chlorine | s-heterocyclic | pyridine | cyano | n-heterocyclic |
| Tryptophan | | furan | bromine | chlorine | s-heterocyclic | pyridine | cyano | n-heterocyclic |
| Tryptophan | | furan | bromine | chlorine | s-heterocyclic | pyridine | cyano | n-heterocyclic |
| Tryptophan | pyrrolidindione | iodine | hydrazone | thiocyanate | *bromine | | hydroxamic acid | cyano |
| Tyrosine | | furan | bromine | chlorine | s-heterocyclic | pyridine | cyano | n-heterocyclic |
| Tyrosine | | furan | bromine | chlorine | s-heterocyclic | pyridine | cyano | n-heterocyclic |
| Tyrosine | | furan | bromine | chlorine | s-heterocyclic | pyridine | cyano | n-heterocyclic |
| Urea | | furan | bromine | chlorine | s-heterocyclic | pyridine | cyano | n-heterocyclic |
| Urea | | furan | bromine | chlorine | s-heterocyclic | pyridine | cyano | n-heterocyclic |
| Urea | | furan | bromine | chlorine | s-heterocyclic | pyridine | cyano | n-heterocyclic |
| Valine | | furan | bromine | chlorine | s-heterocyclic | pyridine | cyano | n-heterocyclic |
| Valine | | furan | bromine | chlorine | s-heterocyclic | pyridine | cyano | n-heterocyclic |
| Vitamin K5 | | furan | bromine | chlorine | s-heterocyclic | pyridine | cyano | n-heterocyclic |
| Vitamin K5 | | furan | bromine | chlorine | s-heterocyclic | pyridine | cyano | n-heterocyclic |
| Xylitol | | furan | bromine | chlorine | s-heterocyclic | pyridine | cyano | n-heterocyclic |

| Co-crystal Former | Interacting Group | | | | | | |
|---|---|---|---|---|---|---|---|
| Saccharin | ketone | phosphate ester | | fluorine | carbamate | imidazole | BF4 |
| Salicylic Acid | ketone | phosphate ester | | fluorine | carbamate | imidazole | BF4 |
| Salicylic Acid | ketone | phosphate ester | | fluorine | carbamate | imidazole | BF4 |
| Salicylic Acid, 4-amino | ketone | phosphate ester | | fluorine | carbamate | imidazole | BF4 |
| Salicylic Acid, 4-amino | phosphate ester | | fluorine | carbamate | imidazole | BF4 | |
| Salicylic Acid, 4-amino | ketone | phosphate ester | | fluorine | carbamate | imidazole | BF4 |
| Sebacic acid | ketone | phosphate ester | | fluorine | carbamate | imidazole | BF4 |
| Serine | ketone | phosphate ester | | fluorine | carbamate | imidazole | BF4 |
| Serine | ketone | phosphate ester | | fluorine | carbamate | imidazole | BF4 |
| Serine | ketone | phosphate ester | | fluorine | carbamate | imidazole | BF4 |
| Stearic acid | ketone | phosphate ester | | fluorine | carbamate | imidazole | BF4 |
| Succinic Acid | ketone | phosphate ester | | fluorine | carbamate | imidazole | BF4 |
| Tartaric Acid | ketone | phosphate ester | | fluorine | carbamate | imidazole | BF4 |
| Threonine | ketone | phosphate ester | | fluorine | carbamate | imidazole | BF4 |
| Threonine | ketone | phosphate ester | | fluorine | carbamate | imidazole | BF4 |
| Threonine | ketone | phosphate ester | | fluorine | carbamate | imidazole | BF4 |
| Tris | ketone | phosphate ester | | fluorine | carbamate | imidazole | BF4 |
| Tris | ketone | phosphate ester | | fluorine | carbamate | imidazole | BF4 |
| Tryptophan | ketone | phosphate ester | | fluorine | carbamate | imidazole | BF4 |
| Tryptophan | ketone | phosphate ester | | fluorine | carbamate | imidazole | BF4 |

TABLE II-continued

| | | | | | | | | |
|---|---|---|---|---|---|---|---|---|
| Tryptophan | carboxamide | *sulfonic acid | *phosphoric acid | N-oxide | ester | ether | fluorine | acetate thione |
| Tyrosine | ketone | phosphate ester | | fluorine | carbamate | imidazole | BF4 | |
| Tyrosine | ketone | phosphate ester | | fluorine | carbamate | imidazole | BF4 | |
| Tyrosine | ketone | phosphate ester | | fluorine | carbamate | imidazole | BF4 | |
| Urea | ketone | phosphate ester | | fluorine | carbamate | imidazole | BF4 | |
| Urea | ketone | phosphate ester | | fluorine | carbamate | imidazole | BF4 | |
| Urea | ketone | phosphate ester | | fluorine | carbamate | imidazole | BF4 | |
| Valine | ketone | phosphate ester | | fluorine | carbamate | imidazole | BF4 | |
| Valine | ketone | phosphate ester | | fluorine | carbamate | imidazole | BF4 | |
| Vitamin K5 | ketone | phosphate ester | | fluorine | carbamate | imidazole | BF4 | |
| Vitamin K5 | ketone | phosphate ester | | fluorine | carbamate | imidazole | BF4 | |
| Xylitol | ketone | phosphate ester | | fluorine | carbamate | imidazole | BF4 | |

| Co-crystal Former | Interacting Group | | | | |
|---|---|---|---|---|---|
| Saccharin | N—SO2 | thiourea | iodine | | |
| Salicylic Acid | N—SO2 | thiourea | iodine | | |
| Salicylic Acid | N—SO2 | thiourea | iodine | epoxide | |
| Salicylic Acid, 4-amino | N—SO2 | thiourea | iodine | | |
| Salicylic Acid, 4-amino | | | | | |
| Salicylic Acid, 4-amino | N—SO2 | thiourea | iodine | | |
| Sebacic acid | N—SO2 | thiourea | iodine | | |
| Serine | N—SO2 | thiourea | iodine | | |
| Serine | N—SO2 | thiourea | iodine | | |
| Serine | N—SO2 | thiourea | iodine | epoxide | |
| Stearic acid | N—SO2 | thiourea | iodine | | |
| Succinic Acid | N—SO2 | thiourea | iodine | | |
| Tartaric Acid | N—SO2 | thiourea | iodine | | |
| Threonine | N—SO2 | thiourea | iodine | | |
| Threonine | N—SO2 | thiourea | iodine | | |
| Threonine | N—SO2 | thiourea | iodine | epoxide | |
| Tris | N—SO2 | thiourea | iodine | | |
| Tris | N—SO2 | thiourea | iodine | epoxide | |
| Tryptophan | N—SO2 | thiourea | iodine | | |
| Tryptophan | N—SO2 | thiourea | iodine | | |
| Tryptophan | dithiadiazocyclopentadienyl | | | | |
| Tyrosine | N—SO2 | thiourea | iodine | | |
| Tyrosine | N—SO2 | thiourea | iodine | | |
| Tyrosine | N—SO2 | thiourea | iodine | epoxide | |
| Urea | N—SO2 | thiourea | iodine | | |
| Urea | N—SO2 | thiourea | iodine | | |
| Urea | N—SO2 | thiourea | iodine | epoxide | peroxide |
| Valine | N—SO2 | thiourea | iodine | | |
| Valine | N—SO2 | thiourea | iodine | | |
| Vitamin K5 | N—SO2 | thiourea | iodine | | |
| Vitamin K5 | N—SO2 | thiourea | iodine | epoxide | |
| Xylitol | N—SO2 | thiourea | iodine | epoxide | |

TABLE III

| Functional Group | Functional Group Structure | Interacting Group | | | | | |
|---|---|---|---|---|---|---|---|
| pyridine | 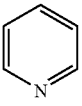 | *alcohol | pyridinium | *amide | nitro | *amine | *carboxylic acid | *sulfonamide |
| imidazole | 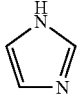 | imidazole | chlorine | acetamide | carboxylate | thione | nitro | cyanamide |
| Hydroxamic acid | 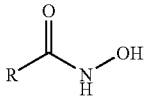 | hydroxamic acid | alcohol | phoshinic ester | alkane | pyridine | amide | sulfonamide |
| peroxide | R—O—OH | ester | peroxide | amide | ether | alkane | N-heterocycle | aromatic |
| epoxide |  | alkane | bromine | alcohol | ester | epoxide | amide | alkene |

TABLE III-continued

| Functional Group | Structure | | | | | | | |
|---|---|---|---|---|---|---|---|---|
| thioester | R-C(=S)-O-R (aromatic) | thioester | alkane | sulfamide | hydroxy | bromine | iodine | |
| thioketone | R-C(=S)-R (alkane) | thioketone | ketone | SULFAMIDE | AMINE | thiol | sulfoxide | |

| Functional Group | | | | Interacting Group | | | | | |
|---|---|---|---|---|---|---|---|---|---|
| pyridine | *ketone | ether | triazole | alkane | ammonium | oxime | *chlorine | alkyne | thiol | n-heterocyclic ring | thionedisulfide |
| imidazole | ketone | cyano | carboxylic acid | alcohol | alkane | thiol | amine | phosphinic acid hemihydrate | chlorine | sulfonyl | sulfoxide |
| Hydroxamic acid | carboxylate | phosphine | amine | aromatic | | | | | | | |
| peroxide | alcohol | pyrimidinedione | analine | thiazole | peroxy acid | ketone | carboxylic acid | azide | phosphire oxide | sulfonamide | analine |
| epoxide | hydrazone | aromatic | thioether | ketone | aldehyde | chlorine | carboxylic acid | alkyne | | ammonium | fluorine |
| thioester | amine | cyano | thioketone | amide | alkene | chlorine sulfone | nitro iodine | | | | |
| thioketone | oxo | chlorine | bromine | AROMATIC | | | | AZOXY | potassium | epoxide | n-oxide |
| pyridine | pyrrolidindione | iodine | hydrazone | thiocyanate | *bromine | aromatic | hydroxamic acid | cyano | carboxamide | *sulfonic acid | *phosphoric acid | N-oxide |
| imidazole | amide | fluorine | sulfonate ester | | | | | | | | |
| Hydroxamic acid | | | | | | | | | | | |
| peroxide | | | | | | | | | | | |
| epoxide | nitro | amine | cyano | | | | | | | | |
| thioester | | | | | | | | | | | |
| thioketone | cyano | iron | cobalt | amine | sulfate | | | | | | |
| pyridine | ester | ether | fluorine | acetate | thione | dithiadiazocyclopentadienyl | | | | | |
| imidazole | | | | | | | | | | | |
| Hydroxamic acid | | | | | | | | | | | |
| peroxide | | | | | | | | | | | |
| epoxide | | | | | | | | | | | |
| thioester | | | | | | | | | | | |
| thioketone | | | | | | | | | | | |

| Functional Group | Functional Group Structure | | | Interacting Group | | | |
|---|---|---|---|---|---|---|---|
| nitrate ester | —O—NO₂ | aromatic | amide | alkane | chlorine | nitrate ester | bromine | alcohol |
| Thiophosphate ester-O | —O—P(=S)(O⁻)(OH) | amine | imidazole | cyclic amide | | | | |
| Phosphate ester | —O—P(=O)(O⁻)(OH) | aromatic | alcohol | phosphate ester | aromatic N-ring | pyridine | analine | amine |
| Ketone | R-C(=O)-R | alcohol | ketone | thiol | amide | amine | analine | phenol |

TABLE III-continued

| Aldehyde |  | alcohol | ketone | thiol | amide | amine | analine | phenol |
|---|---|---|---|---|---|---|---|---|
| Thiol | R—SH | carboxylic acid | sodium | aldehyde | ketone | aromatic-N | cadmium | alkane |
| Alcohol | R—OH | alcohol | ketone | thiol | amide | amine | analine | phenol |

| Functional Group | Interacting Group | | | | | | | | |
|---|---|---|---|---|---|---|---|---|---|
| nitrate ester | ether | acetate | | | | | | | |
| Thiophosphate ester-O | | | | | | | | | |
| Phosphate ester | sodium | potassium | lithium | carboxylic acid | amide | alkane | | | |
| Ketone | phosphate | sulfate | sulfone | nitrate | pyridine | aromatic | carboxilic acid | metals | aldehyde | ester | ether |
| Aldehyde | phosphate | sulfate | sulfone | nitrate | pyridine | aromatic | carboxilic acid | metals | aldehyde | ester | ether |
| Thiol | arsenic | chlorine | alcohol | potassium | Ru | aromatic | Rb | Sb | | |
| Alcohol | phosphate | sulfate | sulfone | nitrate | pyridine | aromatic | carboxilic acid | metals | aldehyde | ester | ether |
| nitrate ester | | | | | | | | | |
| Thiophosphate ester-O | | | | | | | | | |
| Phosphate ester | | | | | | | | | |
| Ketone | cyano | | furan | bromine | chlorine | s-heterocyclic | pyridine | cyano | n-heterocyclic | ketone | phosphate ester |
| Aldehyde | cyano | | furan | bromine | chlorine | s-heterocyclic | pyridine | cyano | n-heterocyclic | ketone | phosphate ester |
| Thiol | | | | | | | | | |
| Alcohol | cyano | | furan | bromine | chlorine | s-heterocyclic | pyridine | cyano | n-heterocyclic | ketone | phosphate ester |
| nitrate ester | | | | | | | | | |
| Thiophosphate ester-O | | | | | | | | | |
| Phosphate ester | | | | | | | | | |
| Ketone | fluorine | carbamate | imidazole | BF4 | alkane | aromatic | N—SO2 | thiourea | iodine | |
| Aldehyde | fluorine | carbamate | imidazole | BF4 | alkane | aromatic | N—SO2 | thiourea | iodine | epoxide |
| Thiol | | | | | | | | | | |
| Alcohol | fluorine | carbamate | imidazole | BF4 | alkane | aromatic | N—SO2 | thiourea | iodine | epoxide |

| Functional Group | Functional Group Structure | Interacting Group | | | | | | |
|---|---|---|---|---|---|---|---|---|
| Thioether |  | aromatic-N | amide | amine | aromatic_s | Sp2 amine | sulfoxide | chlorate |
| Ether |  | aromatic-N | amide | amine | aromatic_s | Sp2 amine | sulfoxide | chlorate |
| Cyanamide | N—C≡N | cyano | amine | potassium | aromatic-N | bromine | sodium | imidazole |
| Thiocyanate | —S—C≡N | aromatic-S | ester | ether | | | | |
| sP2 amine |  | thioether | ether | metals | MoOCl4 | BF4 | bromine | chlorine |
| Amine primary | R—NH$_2$ | alcohol | ketone | thiol | amide | amine | analine | phenol |
| Amine secondary | R$_2$—NH | alcohol | ketone | thiol | amide | amine | analine | phenol |

TABLE III-continued

| Functional Group | Interacting Group | | | | | | | | | | |
|---|---|---|---|---|---|---|---|---|---|---|---|
| Thioether | Interacting chlorine | alkyne | cyano | ester | amine | nitro | nitrate | bromine | aldehyde | ketone | peroxide |
| Ether | chlorine | alkyne | cyano | ester | amine | nitro | nitrate | bromine | aldehyde | ketone | peroxide |
| Cyanamide | ether | n-heterocyclic | alcohol | cesium | Ag | | | | | | |
| Thiocyanate | | | | | | | | | | | |
| sP2 amine | | Sp2 amine | sulfate | Osmium | | | | | | | |
| Amine primary | phosphate | sulfate | sulfone | nitrate | pyridine | aromatic | carboxylic acid | metals | aldehyde | ester | ether |
| Amine secondary | phosphate | sulfate | sulfone | nitrate | pyridine | aromatic | carboxylic acid | metals | aldehyde | ester | ether |
| Thioether | epoxide | Ag | Se | heterocyclic-S | iodine | ester | ether | carboxylic acid | sulfate | sulfone | alkane | alcohol |
| Ether | epoxide | Ag | Se | heterocyclic-S | iodine | ester | ether | carboxylic acid | sulfate | sulfone | alkane | alcohol |
| Cyanamide | | | | | | | | | | | |
| Thiocyanate | | | | | | | | | | | |
| sP2 amine | | | | | | | | | | | |
| Amine primary | cyano | | furan | bromine | chlorine | s-heterocyclic | pyridine | cyano | n-heterocyclic | ketone | phosphate ester |
| Amine secondary | cyano | | furan | bromine | chlorine | s-heterocyclic | pyridine | cyano | n-heterocyclic | ketone | phosphate ester |
| Thioether | | phosphate | | | | | | | | | |
| Ether | | phosphate | cyanamide | | | | | | | | |
| Cyanamide | | | | | | | | | | | |
| Thiocyanate | | | | | | | | | | | |
| sP2 amine | | | | | | | | | | | |
| Amine primary | fluorine | carbamate | imidazole | BF4 | alkane | aromatic | N—SO2 | thiourea | iodine | | |
| Amine secondary | fluorine | carbamate | imidazole | BF4 | alkane | aromatic | N—SO2 | thiourea | iodine | | |

| Functional Group | Functional Group Structure | Interacting Group | | | | | | |
|---|---|---|---|---|---|---|---|---|
| Amine tertiary | $R_3$—N | alcohol | ketone | thiol | amide | amine | analine | phenol |
| Amide | 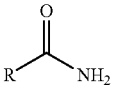 | alcohol | ketone | thiol | amide | amine | analine | phenol |
| Sulfonic acid | 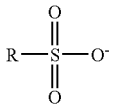 | pyridine | ketone | aldehyde | ether | ester | amide | carboxilic acid |
| Phosphinic acid | 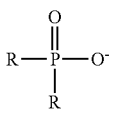 | alkane | potassium | lithium | n-heterocyclic | oxime | amide | phenol |
| Phosphonic acid | 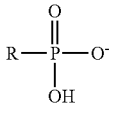 | alkane | potassium | lithium | n-heterocyclic | oxime | amide | phenol |
| Carboxylic acid | 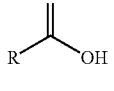 | alcohol | ketone | thiol | amide | amine | analine | phenol |

TABLE III-continued

| Sulfate ester | ![structure: -O-S(=O)(=O)-O-] | pyridine | ketone | aldehyde | ether | ester | amide | carboxylic acid |

| Functional Group | Interacting Group | | | | | | | | | |
|---|---|---|---|---|---|---|---|---|---|---|
| Amine tertiary | phosphate | sulfate | sulfone | nitrate | pyridine | aromatic | carboxylic acid | metals | aldehyde | ester | ether |
| Amide | phosphate | sulfate | sulfone | nitrate | pyridine | aromatic | carboxylic acid | metals | aldehyde | ester | ether |
| Sulfonic acid | amine | metals | thioether | | sulfate | alcohol | | | | | |
| Phosphinic acid | aromatic | amine | alcohol | | metals | | | | | | |
| Phosphonic acid | aromatic | amine | alcohol | | metals | carboxylic acid | Sp2 amine | analine | ether | phosphonic acid | aromatic-N |
| Carboxylic acid | phosphate | sulfate | sulfone | nitrate | pyridine | aromatic | carboxylic acid | metals | aldehyde | ester | ether |
| Sulfate ester | amine | metals | thioether | sulfate | alcohol | | | | | | |
| Amine tertiary | cyano | | furan | bromine | chlorine | s-heterocyclic | pyridine | cyano | n-heterocyclic | ketone | phosphate ester |
| Amide | cyano | | furan | bromine | chlorine | s-heterocyclic | pyridine | cyano | n-heterocyclic | ketone | phosphate ester |
| Sulfonic acid | | | | | | | | | | | |
| Phosphinic acid | | | | | | | | | | | |
| Phosphonic acid | ketone | aldehyde | imidazole | | | | | | | | |
| Carboxylic acid | cyano | | furan | bromine | chlorine | s-heterocyclic | pyridine | cyano | n-heterocyclic | ketone | phosphate ester |
| Sulfate ester | | | | | | | | | | | |
| Amine tertiary | fluorine | carbamate | imidazole | BF4 | alkane | aromatic | N—SO2 | thiourea | iodine | | |
| Amide | fluorine | carbamate | imidazole | BF4 | alkane | aromatic | N—SO2 | thiourea | iodine | epoxide | peroxide |
| Sulfonic acid | | | | | | | | | | | |
| Phosphinic acid | | | | | | | | | | | |
| Phosphonic acid | | | | | | | | | | | |
| Carboxylic acid | fluorine | carbamate | imidazole | BF4 | alkane | aromatic | N—SO2 | thiourea | iodine | | |
| Sulfate ester | | | | | | | | | | | |

| Functional Group | Functional Group Structure | Interacting Group | | | | | | |
|---|---|---|---|---|---|---|---|---|
| Oxime | C=N—OH | alcohol | alkane | amine | amide | ether | ester | pyridine |
| Nitrile | —C≡N | metal | ketone | phenol | alcohol | | cyano | amine |
| Diazo | $RH_2C-N=N-CH_2R$ | | | | | | | |
| Nitro | $NO_2$ | pyridine | ketone | aldehyde | ether | ester | amide | carboxylic acid |
| S-heterocyclic ring | [thiolane structure] | alcohol | thioketone | thioether | s-heterocyclic | ketone | aromatic | alkene |
| Thiophene | [thiophene structure] | chlorine | fluorine | amide | ketone | NO | SO | CO |
| N-heterocyclic ring | [pyrrolidine structure] | alcohol | thioketone | thioether | s-heterocyclic | ketone | aromatic | alkene |

TABLE III-continued

| Functional Group | Structure | | | | | | | | |
|---|---|---|---|---|---|---|---|---|---|
| O-heterocyclic ring |  | alcohol | thioketone | thioether | s-heterocyclic | ketone | aromatic | alkene | |

| Functional Group | | | | Interacting Group | | | | | |
|---|---|---|---|---|---|---|---|---|---|
| Oxime | n-aromatic | chlorate | chlorine | Sp2-N | diazo | thioketone | cyano | n-oxide | ketone | aldehyde | carboxylic acid |
| Nitrile | analine | bromine | amide | alkane | carboxylic acid | chlorine | n-heterocyclic | aromatic | potassium | aldehyde | thioether |
| Diazo | | | | | | | | | | | |
| Nitro | amine | metals | thioether | sulfate | alcohol | | | | | | |
| S-heterocyclic ring | amine | chlorine | BF4 | sulfate | ester | NO | ether | amide | iodine | carboxylic acid | sodium |
| Thiophene | | | | | | | | | | | |
| N-heterocyclic ring | amine | chlorine | BF4 | sulfate | ester | NO | ether | amide | iodine | carboxylic acid | sodium |
| O-heterocyclic ring | amine | chlorine | BF4 | sulfate | ester | NO | ether | amide | iodine | carboxylic acid | sodium |
| Oxime | bromine | aromatic | pyridine | BF4 | | | | | | | |
| Nitrile | pyridine | n-aromatic | bromine | ether | s-aromatic | thiophene | | | | | |
| Diazo | | | | | | | | | | | |
| Nitro | | | | | | | | | | | |
| S-heterocyclic ring | cyano | chloride | furan | | | | | | | | |
| Thiophene | | | | | | | | | | | |
| N-heterocyclic ring | cyano | chloride | aldehyde | | | | | | | | |
| O-heterocyclic ring | cyano | chloride | aldehyde | | | | | | | | |
| Oxime | | | | | | | | | | | |
| Nitrile | | | | | | | | | | | |
| Diazo | | | | | | | | | | | |
| Nitro | | | | | | | | | | | |
| S-heterocyclic ring | | | | | | | | | | | |
| Thiophene | | | | | | | | | | | |
| N-heterocyclic ring | | | | | | | | | | | |
| O-heterocyclic ring | | | | | | | | | | | |

| Functional Group | Functional Group Structure | | | Interacting Group | | | | |
|---|---|---|---|---|---|---|---|---|
| Pyrrole |  | chlorine | fluorine | amide | ketone | NO | SO | CO |
| Furan |  | s-heterocyclic | | | | | | |

TABLE III-continued

| Functional Group | | | | | Interacting Group | | | | | | |
|---|---|---|---|---|---|---|---|---|---|---|---|
| Pyrrole | imidazole | pryridine | n-aromatic | aldehyde | carboxylic acid | sulfate | chlorine | bromine | oxime | alcohol | phenol |
| Furan Pyrrole | ester | ether | | | | | | | | | |
| Furan Pyrrole | | | | | | | | | | | |
| Furan | | | | | | | | | | | |

Figure 18:
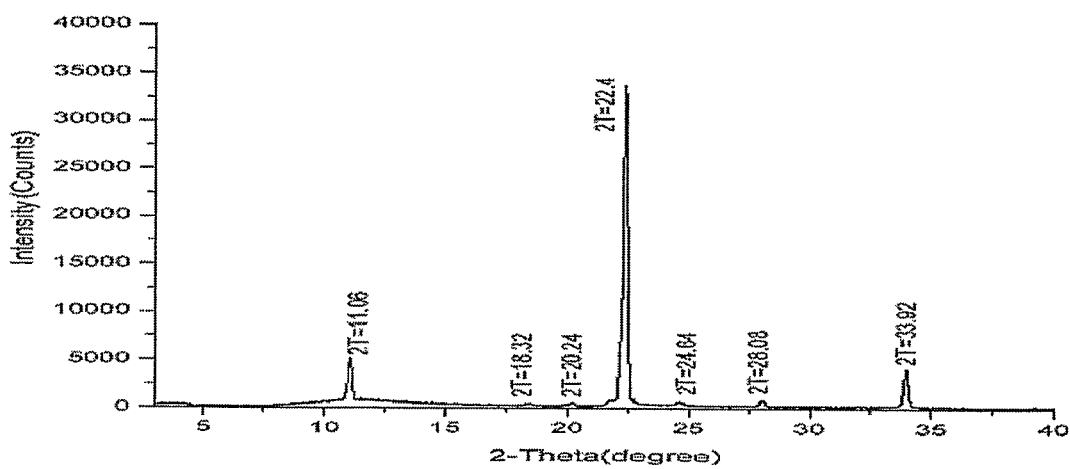
FIG. 18—PXRD diffractogram for stavudine:melamine co-crystal.

What is claimed is:

1. A pharmaceutical co-crystal comprising:
    a) a stavudine:melamine co-crystal, wherein said stavudine:melamine co-crystal is characterized by a powder X-ray diffraction pattern comprising peaks at 11.06, 22.40, and 24.64 degrees 2-theta;
    b) a stavudine:melamine co-crystal, wherein said stavudine:melamine co-crystal is characterized by a powder X-ray diffraction pattern comprising peaks at 11.06, 18.32, and 20.24 degrees 2-theta;
    c) a stavudine:melamine co-crystal, wherein said stavudine:melamine co-crystal is characterized by a powder X-ray diffraction pattern that is substantially as shown in FIG. 18;
    d) a stavudine:melamine co-crystal, wherein said stavudine:melarnine co-crystal is characterized by an IR spectrum comprising peaks at 1655, 1446, and 799 cm$^{-1}$;
    e) a stavudine:melamine co-crystal, wherein said stavudine:melamine co-crystal is characterized by an IR spectrum comprising peaks at 1542, 1268, and 1091 cm$^{-1}$;
    f) a stavudine :2-aminopyridine co-crystal, wherein said stavudine:2-aminopyridine co-crystal is characterized by an IR spectrum comprising peaks at 1698, 1433, and 1075 cm$^{-1}$;
    g) a stavudine:2-aminopyridine co-crystal, wherein said stavudine:2-aminopyridine co-crystal is characterized by an IR spectrum comprising peaks at 1666, 1221, and 974 cm$^{-1}$;
    h) a stavudine:2-aminopyridine co-crystal, wherein said stavudine:2-aminopyridine co-crystal is characterized by an IR spectrum comprising peaks at 1698, 1666, and 1629 cm$^{-1}$; or
    i) a stavudine:2-aminopyridine co-crystal, wherein said stavudine:2-aminopyridine co-crystal is characterized by IR spectrum that is substantially as shown in FIG. 20A.

2. The pharmaceutical co-crystal according to claim 1, wherein said co-crystal is a stavudine:melamine co-crystal characterized by a powder X-ray diffraction pattern comprising peaks at 11.06, 22.40, and 24.64 degrees 2-theta.

3. The pharmaceutical co-crystal according to claim 1, wherein said co-crystal is a stavudine:melamine co-crystal characterized by a powder X-ray diffraction pattern comprising peaks at 11.06, 18.32, and 20.24 degrees 2-theta.

4. The pharmaceutical co-crystal according to claim 1, wherein said co-crystal is a stavudine:melamine co-crystal characterized by a powder X-ray diffraction pattern that is substantially as shown in FIG. 18.

5. The pharmaceutical co-crystal according to claim 1, wherein said co-crystal is a stavudine:melamine co-crystal characterized by an IR spectrum comprising peaks at 1655, 1446, and 799 cm$^{-1}$.

6. The pharmaceutical co-crystal according to claim 1, wherein said co-crystal is a stavudine:melamine co-crystal characterized by an IR spectrum comprising peaks at 1542, 1268, and 1091 cm$^{-1}$.

7. The pharmaceutical co-crystal according to claim 1, wherein said co-crystal is a stavudine:2-aminopyridine co-crystal characterized by an IR spectrum comprising peaks at 1698, 1433, and 1075 cm$^{-1}$.

8. The pharmaceutical co-crystal according to claim 1, wherein said co-crystal is a stavudine:2-aminopyridine co-crystal characterized by an IR spectrum comprising peaks at 1666, 1221, and 974 cm$^{-1}$.

9. The pharmaceutical co-crystal according to claim 1, wherein said co-crystal is a stavudine:2-aminopyridine co-crystal characterized by an IR spectrum comprising peaks at 1698, 1666, and 1629 cm$^{-1}$.

10. The pharmaceutical co-crystal according to claim 1, wherein said co-crystal is a stavudine:2-aminopyridine co-crystal characterized by IR spectrum that is substantially as shown in FIG. 20A.

11. The stavudine:melamine co-crystal according to claim 1, wherein said stavudine:melamine co-crystal has a melting point at about 186-190 degrees C.

12. The stavudine:melamine co-crystal according to claim 1, wherein said stavudine:melamine co-crystal is characterized by a DSC thermogram comprising an endothermic transition at about 212 degrees C.

13. The stavudine:2-aminopyridine co-crystal according to claim 1, wherein said stavudine:2-aminopyridine co-crystal has a melting point at about 120-122 degrees C.

14. The stavudine:2-aminopyridine co-crystal according to claim 1, wherein said stavudine:2-aminopyridine co-crystal is characterized by a DSC thermogram comprising an endothermic transition at about 156 degrees C.

15. A pharmaceutical composition comprising a pharmaceutical co-crystal of claim 1.

* * * * *

UNITED STATES PATENT AND TRADEMARK OFFICE
CERTIFICATE OF CORRECTION

| | | |
|---|---|---|
| PATENT NO. | : 7,803,786 B2 | Page 1 of 1 |
| APPLICATION NO. | : 11/629807 | |
| DATED | : September 28, 2010 | |
| INVENTOR(S) | : Jennifer McMahon et al. | |

It is certified that error appears in the above-identified patent and that said Letters Patent is hereby corrected as shown below:

Column 12,
Line 25, "200 150 100" should read --200, 150, 100--.
Line 27, "200 150, 100 90" should read --200, 150, 100, 90--.

Column 38,
Line 3, "6.0 ((1995-2002" should read --6.0 (1995-2002--.

Column 62,
Row "Tryptophan",

"
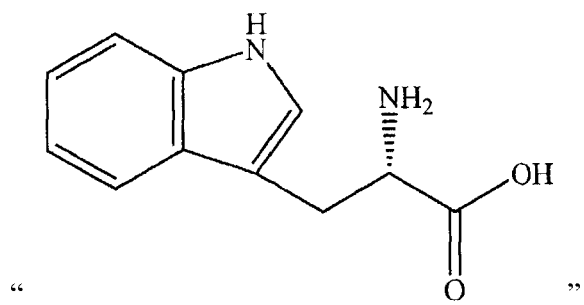
"
should read

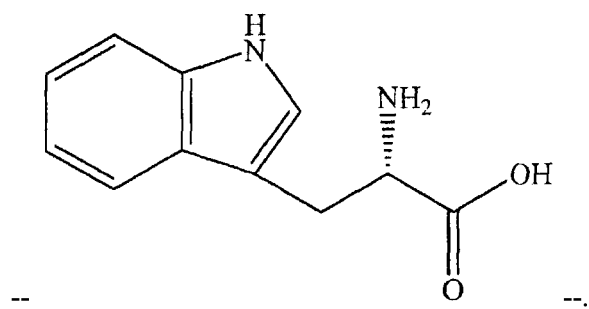

-- --.

Column 82,
Row "Quercetin", "phospphate   cyanamide" should read --phosphate   cyanamide--.

Signed and Sealed this
Eighth Day of February, 2011

David J. Kappos
*Director of the United States Patent and Trademark Office*